US011844695B2

(12) United States Patent
Rajagopal et al.

(10) Patent No.: US 11,844,695 B2
(45) Date of Patent: Dec. 19, 2023

(54) DEVICES FOR TRANSCATHETER CHORDAL IMPLANTATION AND METHODS OF IMPLANTATION

(71) Applicant: OPUS MEDICAL THERAPIES, LLC, Atlanta, GA (US)

(72) Inventors: Vivek Rajagopal, Atlanta, GA (US); Jaime Eduardo Sarabia, Mableton, GA (US); Yenchin Liao, Cary, CO (US); Alfred Raschdorf, Jr., St. James, NY (US)

(73) Assignee: Opus Medical Therapies, LLC, Atlanta, GA (US)

( * ) Notice: Subject to any disclaimer, the term of this patent is extended or adjusted under 35 U.S.C. 154(b) by 155 days.

(21) Appl. No.: 17/066,941

(22) Filed: Oct. 9, 2020

(65) Prior Publication Data
US 2021/0106422 A1 Apr. 15, 2021

Related U.S. Application Data

(60) Provisional application No. 62/914,357, filed on Oct. 11, 2019.

(51) Int. Cl.
*A61F 2/24* (2006.01)
(52) U.S. Cl.
CPC .......... *A61F 2/2457* (2013.01); *A61F 2/2466* (2013.01); *A61F 2220/0016* (2013.01);
(Continued)
(58) Field of Classification Search
CPC ................. A61F 2/2457; A61F 2/2466; A61F 2220/0016; A61F 2220/0075;
(Continued)

(56) References Cited

U.S. PATENT DOCUMENTS

| 8,790,394 B2 | 7/2014 | Miller et al. |
| 10,667,911 B2 | 6/2020 | Ketai et al. |

(Continued)

FOREIGN PATENT DOCUMENTS

| CN | 109044564 A | 12/2018 |
| EP | 2575683 B1 | 7/2019 |

(Continued)

OTHER PUBLICATIONS

International Search Report and Written Opinion in corresponding International application No. PCT/ JS2020/054983 dated Feb. 10, 2021.

(Continued)

*Primary Examiner* — Keri J Nelson
*Assistant Examiner* — Rebecca Lynee Zimmerman
(74) *Attorney, Agent, or Firm* — FisherBroyles, LLP; Rachel H. Huffstetler

(57) ABSTRACT

An endovascular medical assembly and method for restoring chordal support to a leaflet of a heart valve by implanting artificial chordae tendinea in the heart. A chord is inserted into the heart endovascularly with a leaflet grasper which pierces the leaflet and implants the chord through the leaflet. An anchor assembly is implanted into an intracardiac wall and has anchor lines extending therefrom. The chord and an anchor line are assembled by a line gathering member and the tension of the chord is adjusted and secured. The chord is, thus, secured to the anchor assembly to support the leaflet.

64 Claims, 43 Drawing Sheets

(52) U.S. Cl.
CPC ......... *A61F 2220/0075* (2013.01); *A61F 2230/0091* (2013.01)

(58) Field of Classification Search
CPC ..... A61F 2230/0091; A61F 2220/0091; A61B 17/0469; A61B 17/0482; A61B 2017/0406; A61B 2017/0409; A61B 2017/0441; A61B 2017/0464; A61B 2017/0496; A61B 2017/06052; A61B 17/0401
See application file for complete search history.

(56) References Cited

U.S. PATENT DOCUMENTS

| | | | |
|---|---|---|---|
| 10,695,178 | B2 | 6/2020 | Zentgraf et al. |
| 10,820,991 | B2 | 11/2020 | Rajagopal et al. |
| 10,820,992 | B2 | 11/2020 | Rajagopal et al. |
| 10,925,731 | B2 | 2/2021 | Bishop et al. |
| 11,103,351 | B2 | 8/2021 | Rajagopal et al. |
| 11,123,187 | B2 | 9/2021 | Rajagopal et al. |
| 2007/0118151 | A1* | 5/2007 | Davidson ........... A61B 17/0469 606/151 |
| 2014/0114404 | A1 | 4/2014 | Gammie |
| 2018/0185153 | A1* | 7/2018 | Bishop ................. A61F 2/2466 |
| 2019/0183480 | A1 | 6/2019 | Hiorth et al. |
| 2019/0216601 | A1* | 7/2019 | Purcell ................ A61F 2/2466 |
| 2020/0268373 | A1* | 8/2020 | Nobles ................ C12N 9/0083 |
| 2021/0022858 | A1 | 1/2021 | Miller et al. |

FOREIGN PATENT DOCUMENTS

| | | |
|---|---|---|
| WO | 2008101113 A1 | 8/2008 |
| WO | 2013/003228 A1 | 1/2013 |
| WO | 2018126188 A1 | 7/2018 |
| WO | 2019/145941 A1 | 8/2019 |
| WO | 2020/123719 A1 | 6/2020 |
| WO | 2020/187944 A1 | 9/2020 |
| WO | 2021/072193 A1 | 4/2021 |
| WO | 2021257278 A1 | 12/2021 |

OTHER PUBLICATIONS

Extended European Search Report issued in App. No. EP20875061.2, dated Oct. 17, 2023, 11 pages.

\* cited by examiner

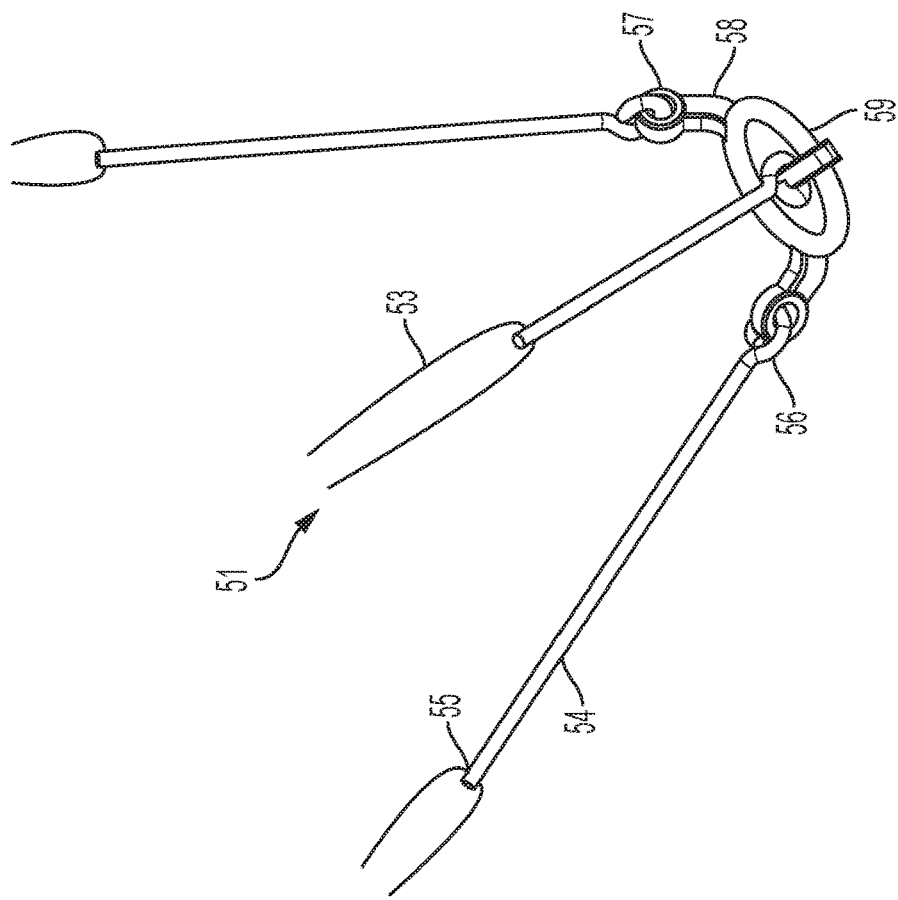
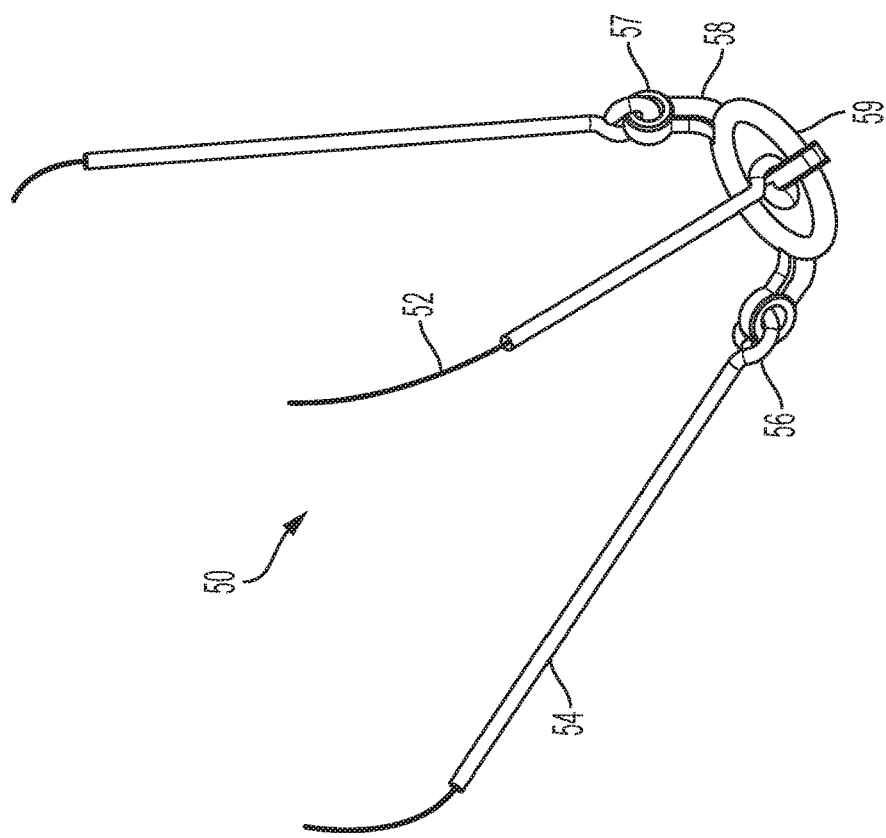

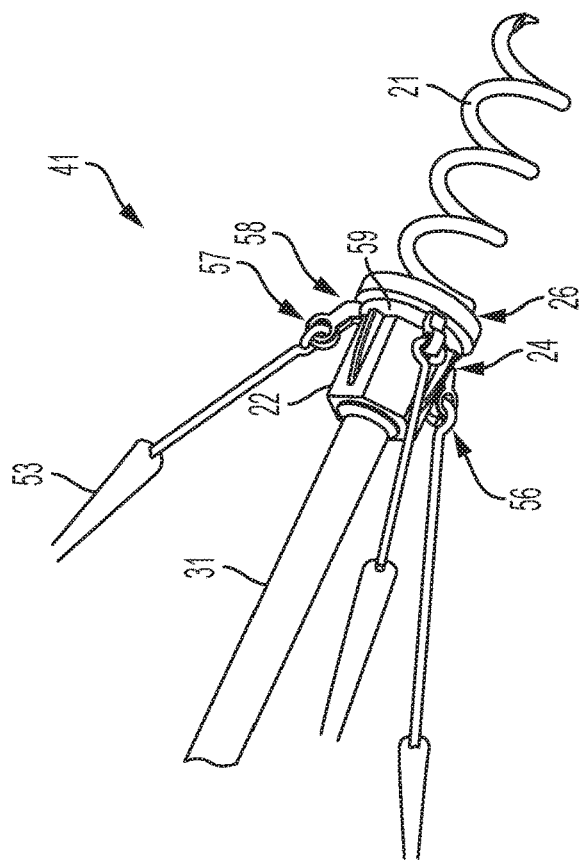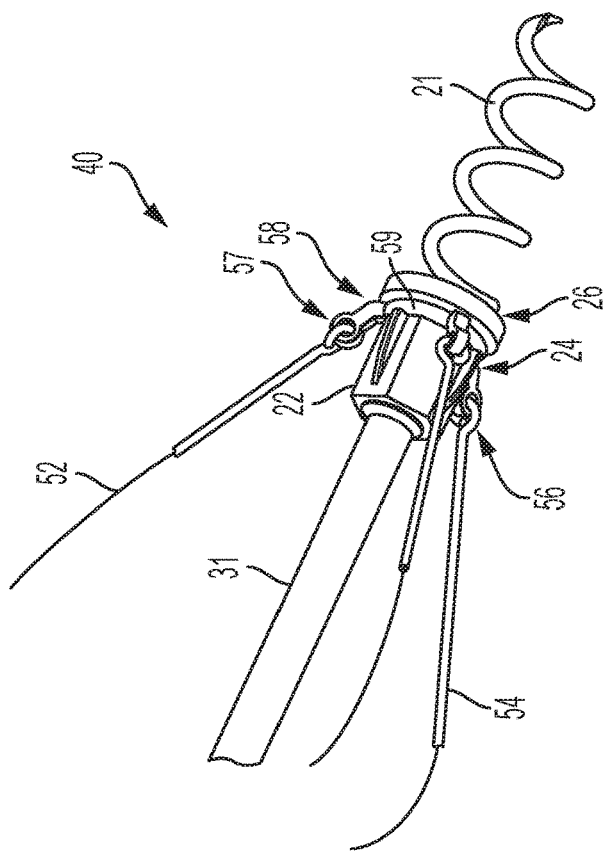

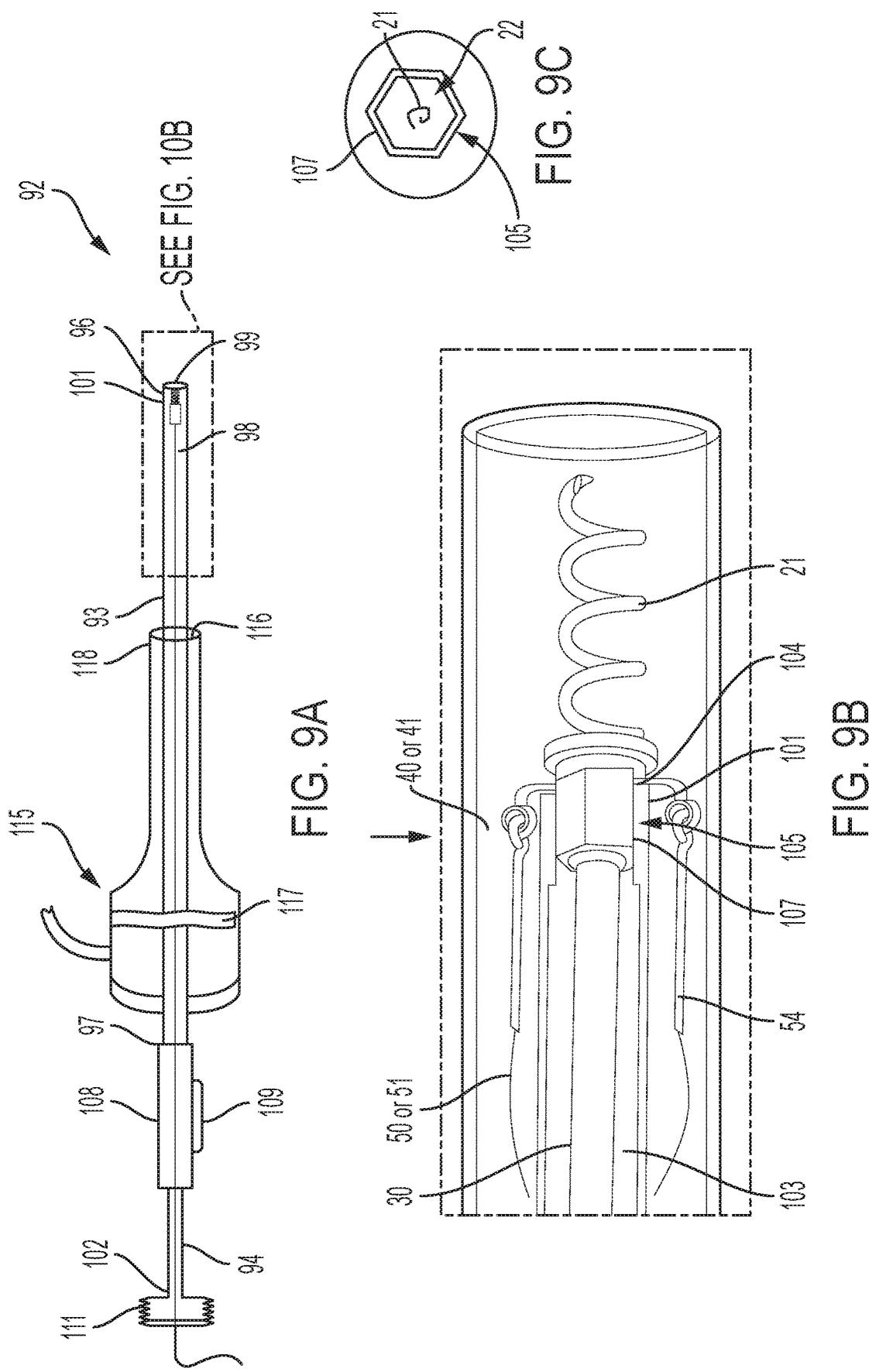

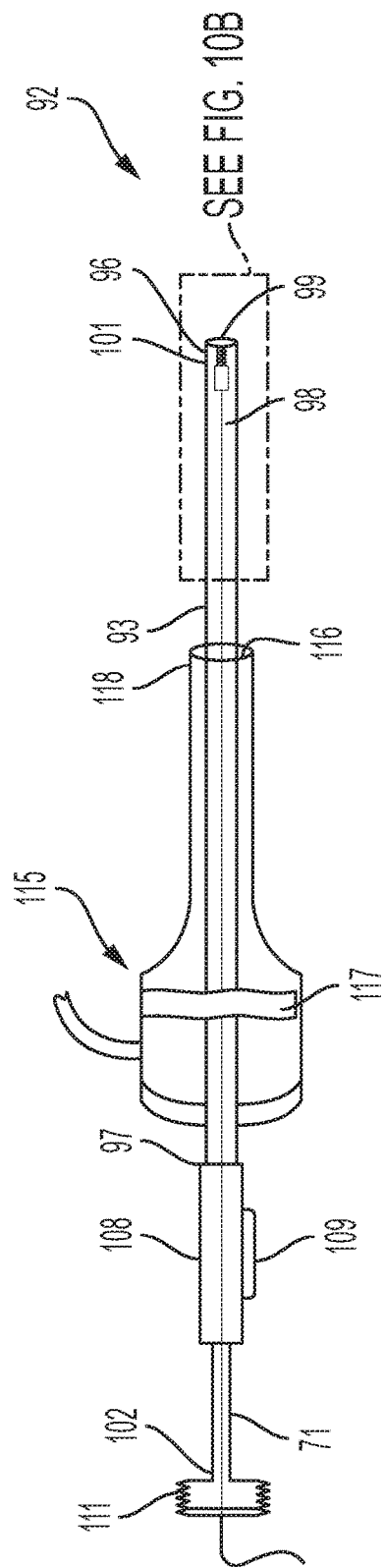
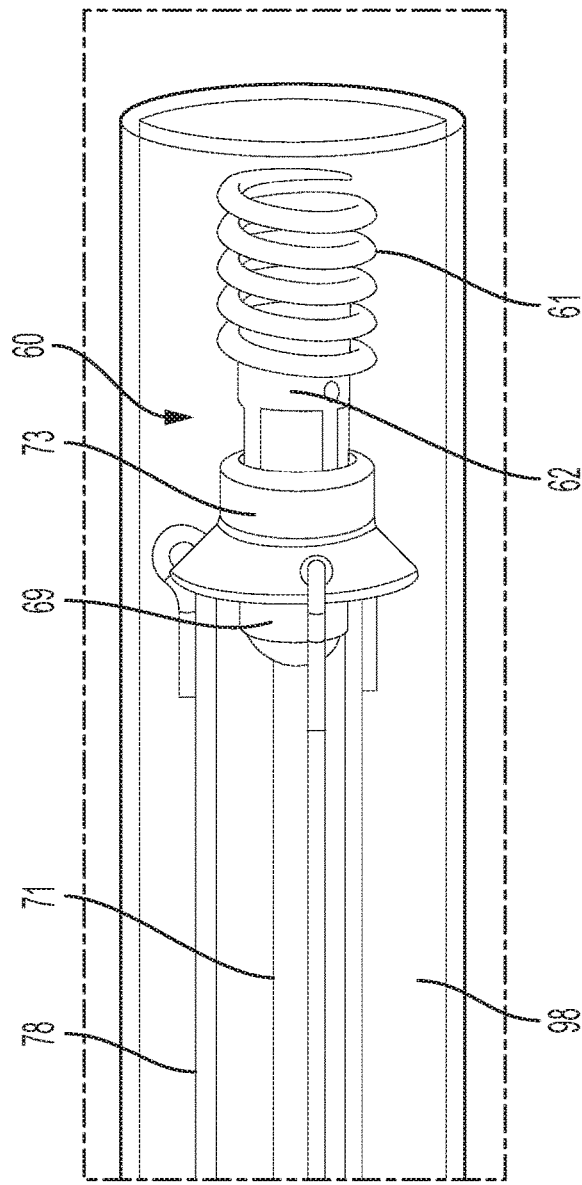
FIG. 10A
FIG. 10B

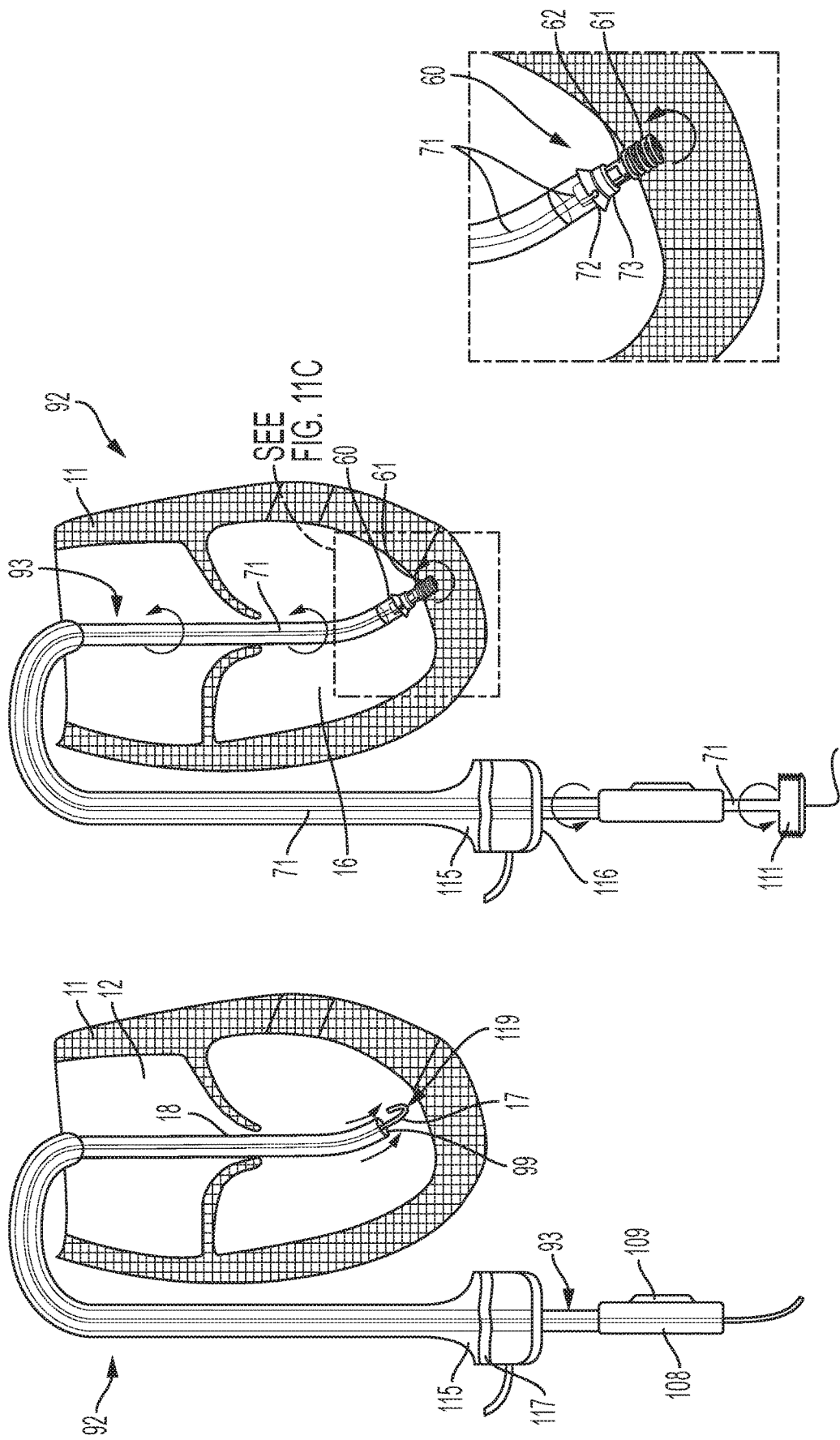

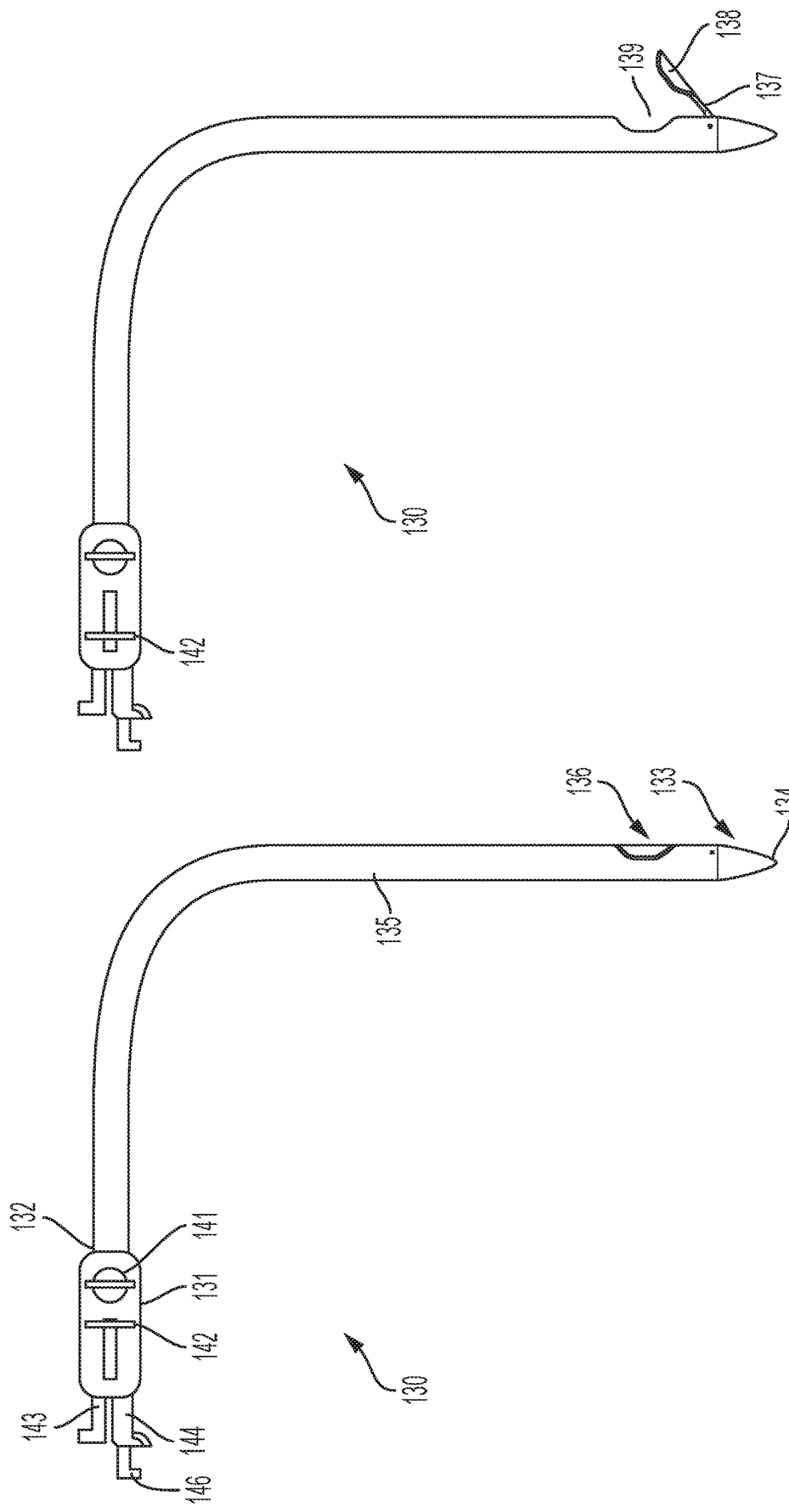

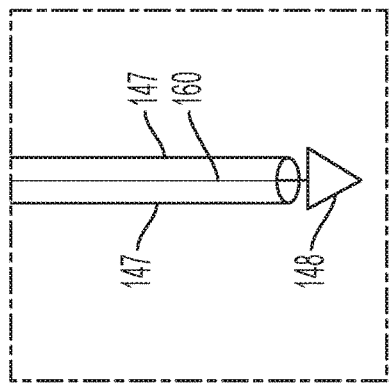
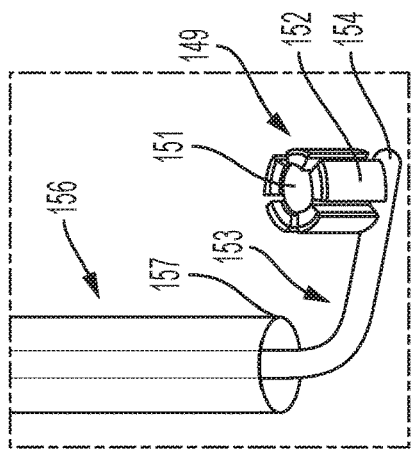
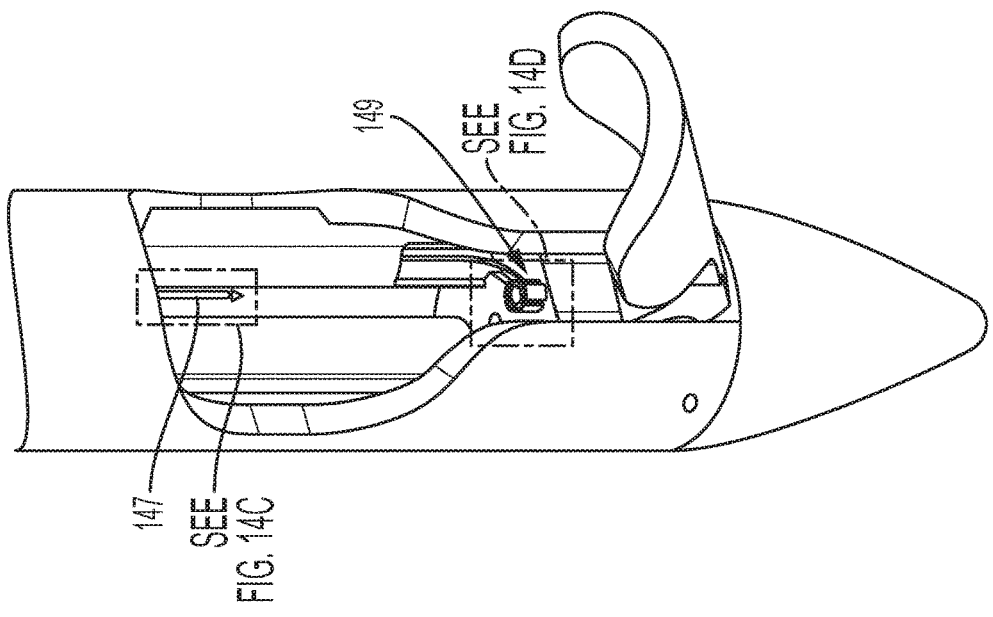
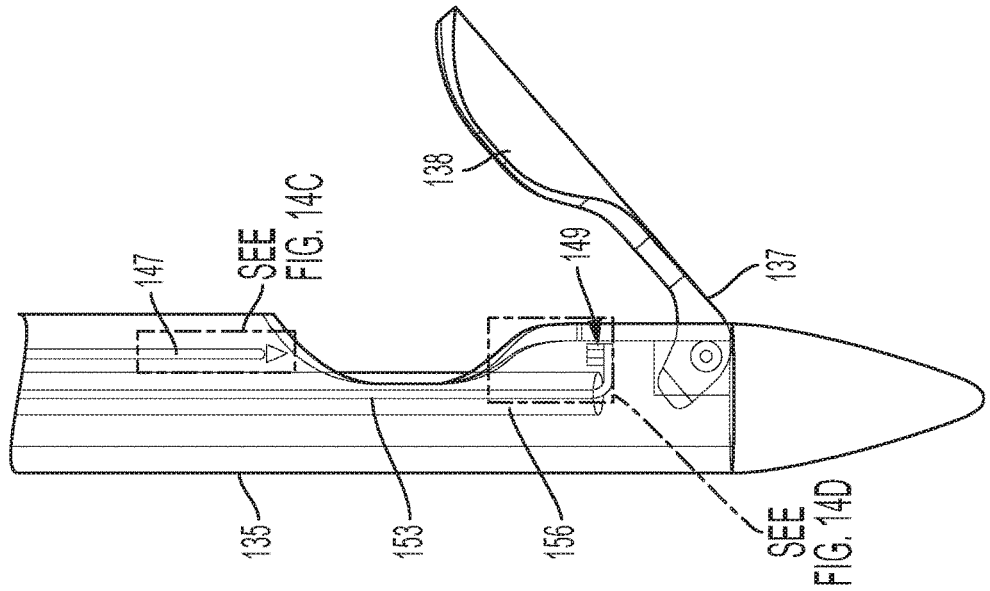

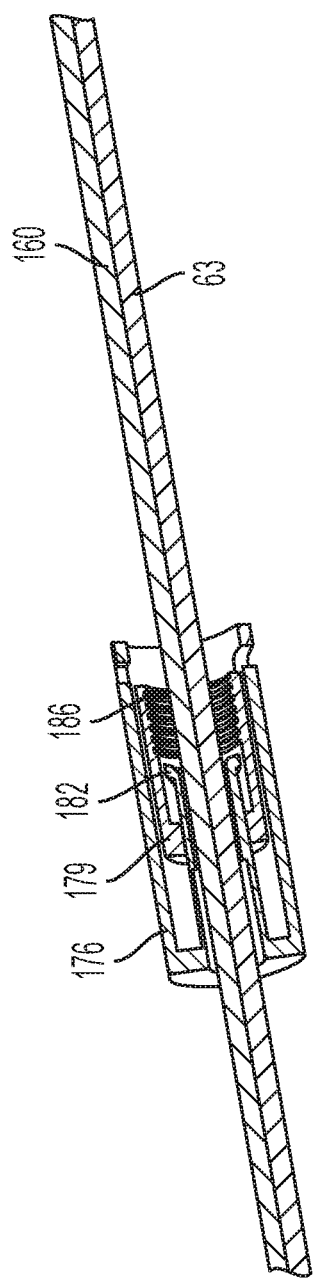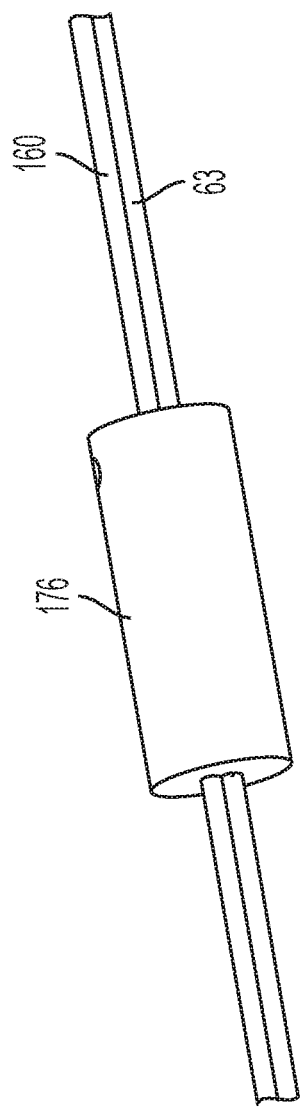
FIG. 32A
FIG. 32B

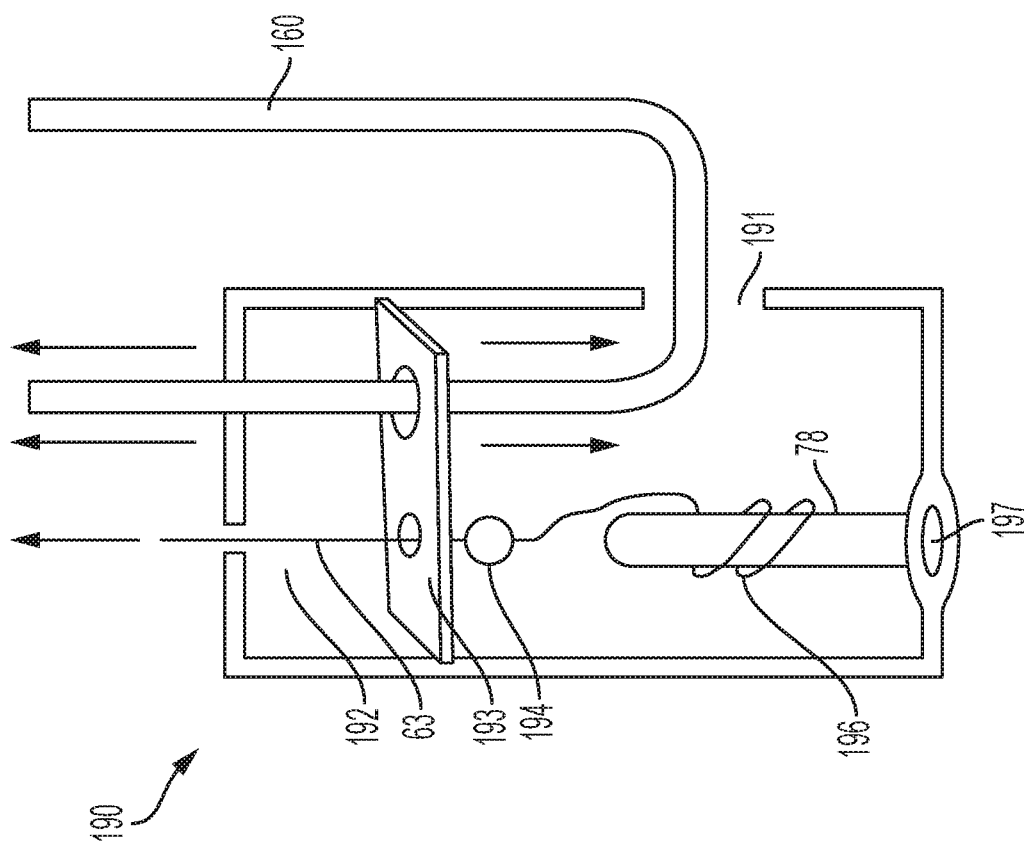
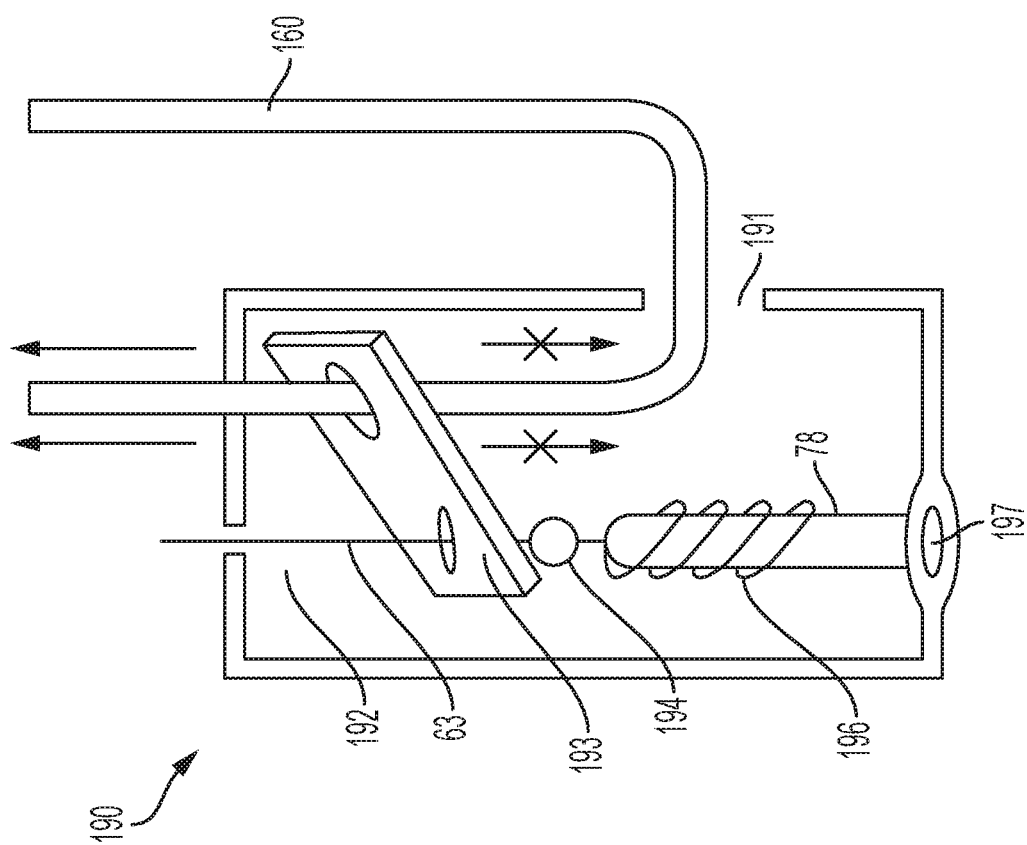

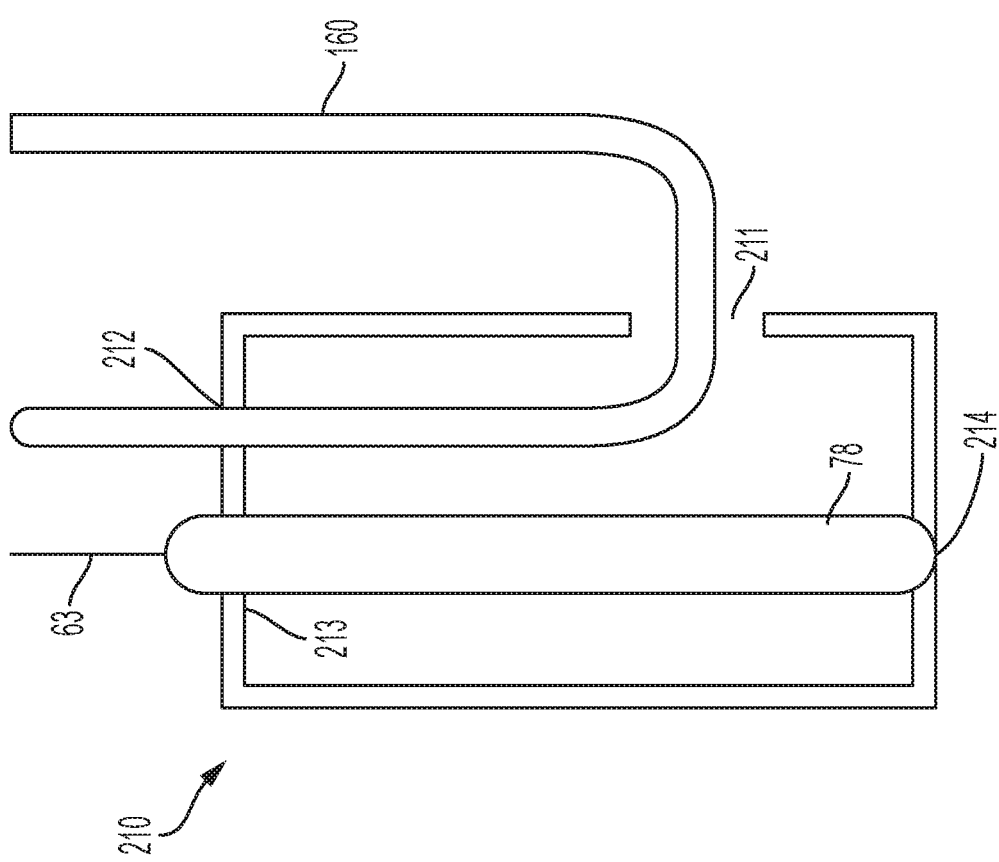

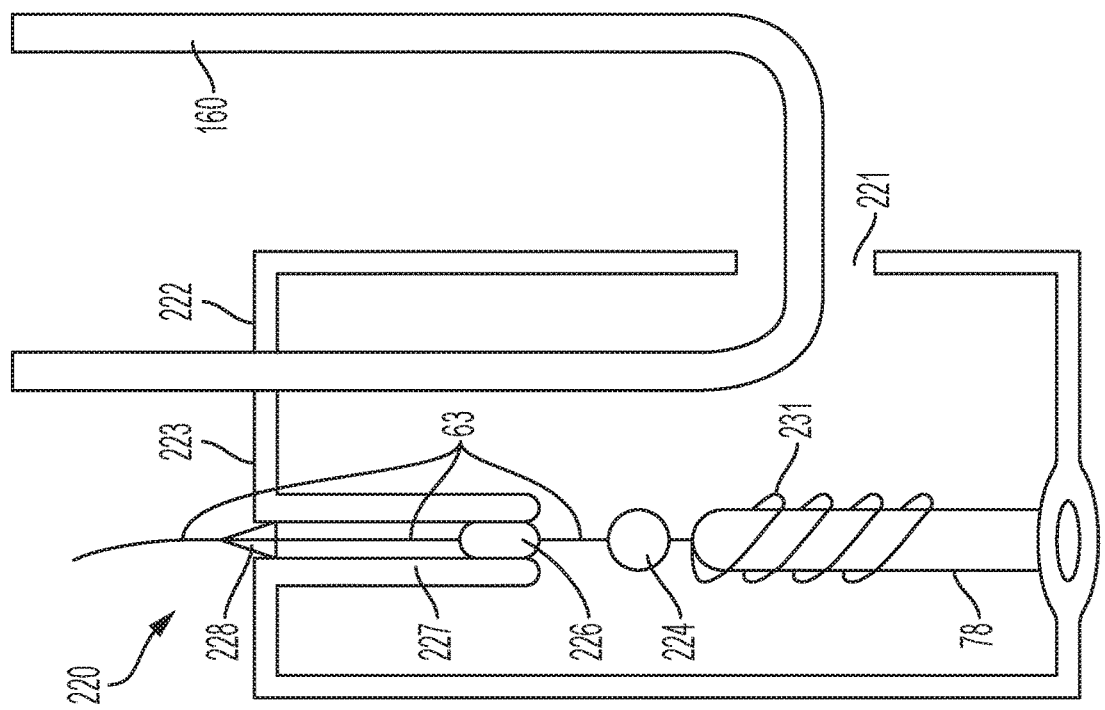
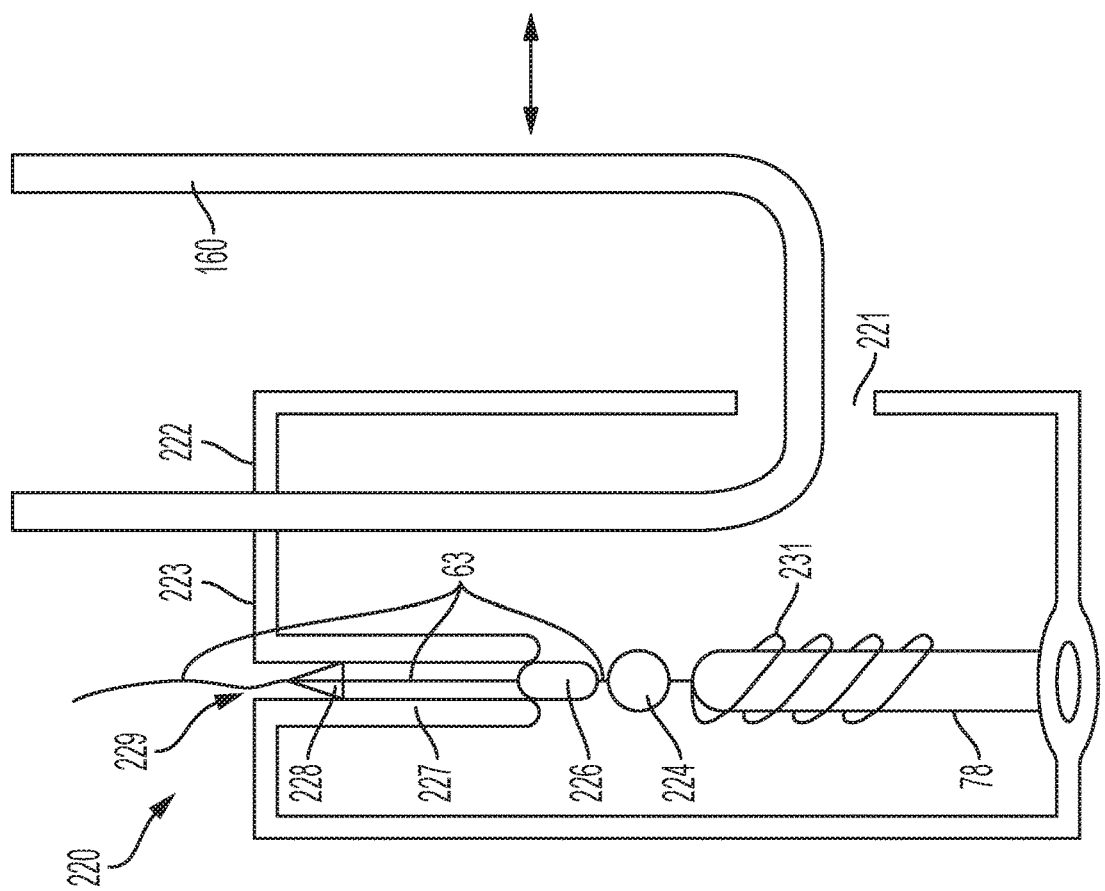
FIG. 39A
FIG. 39B

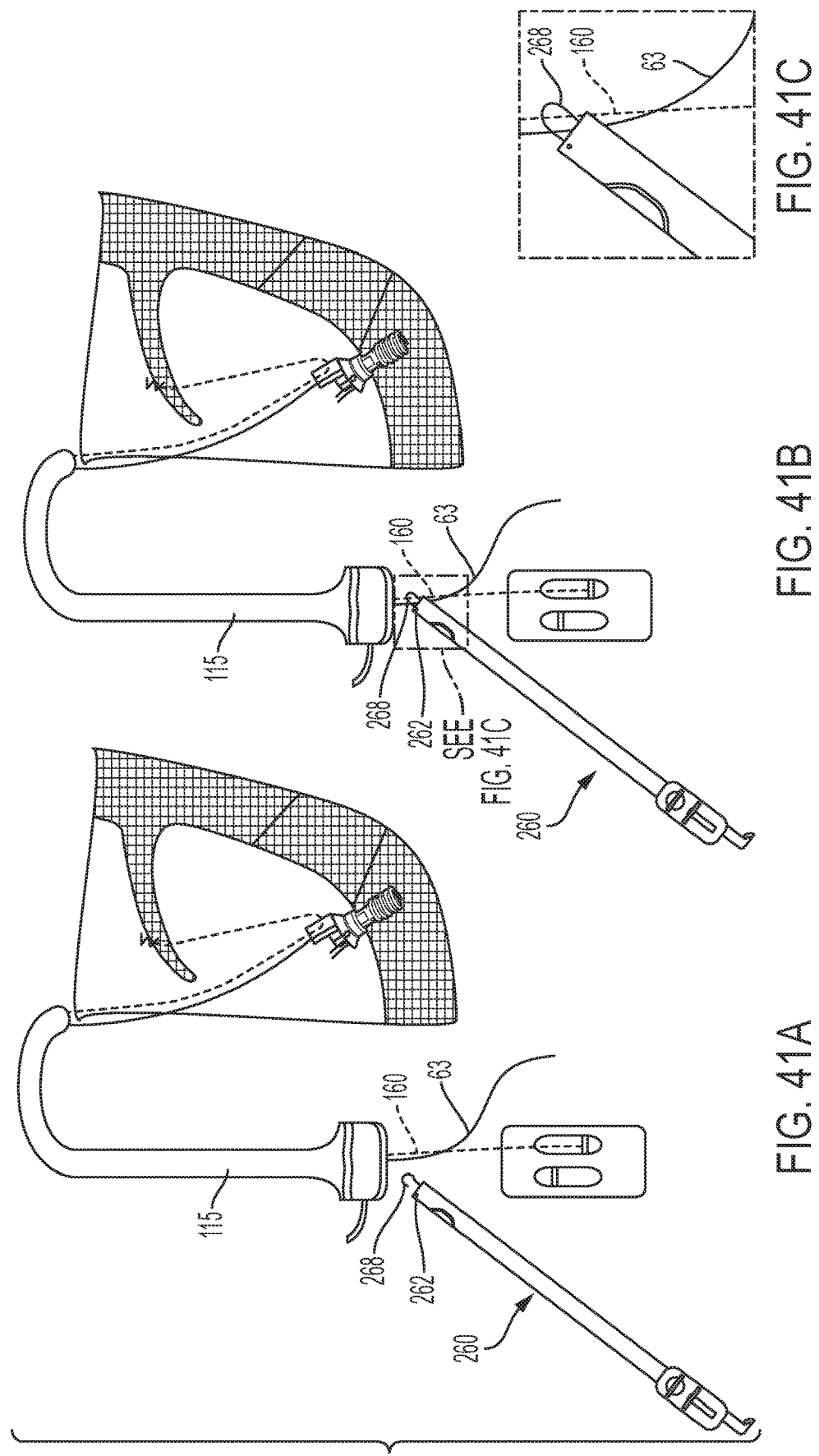

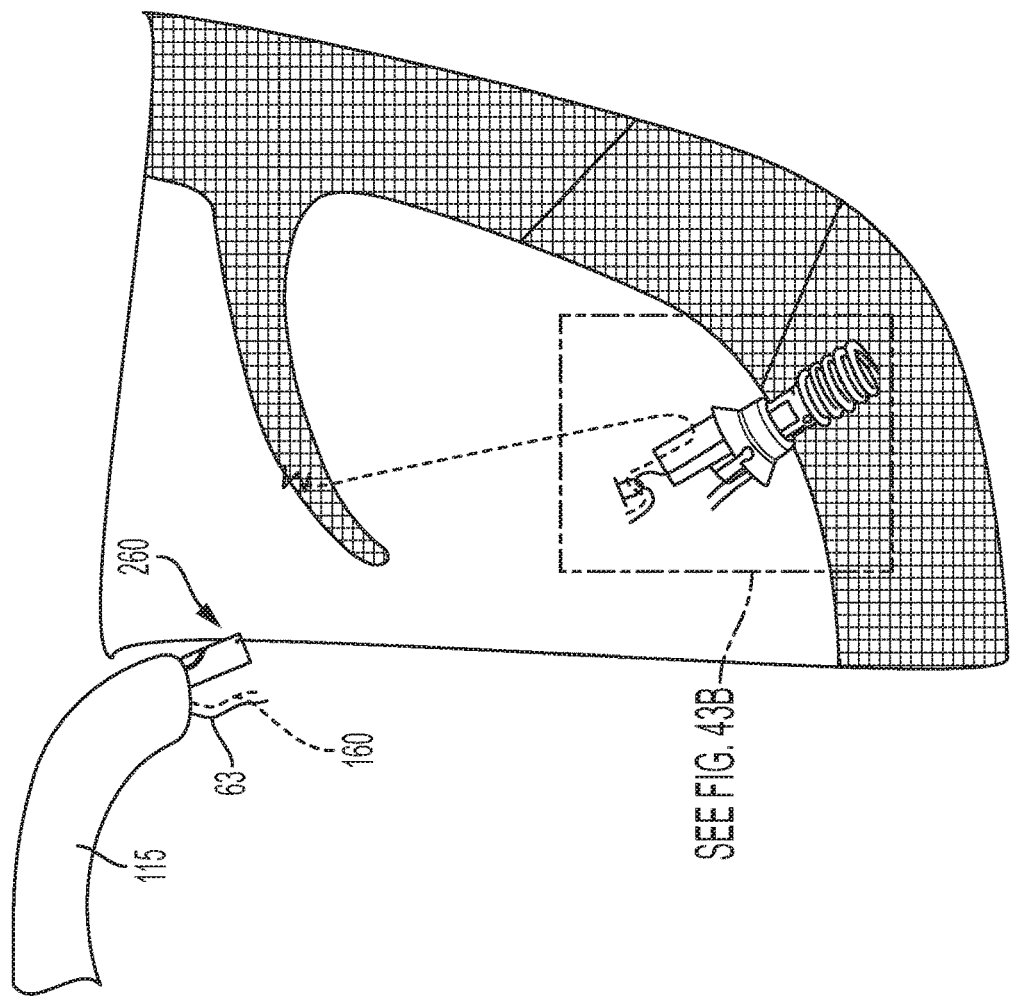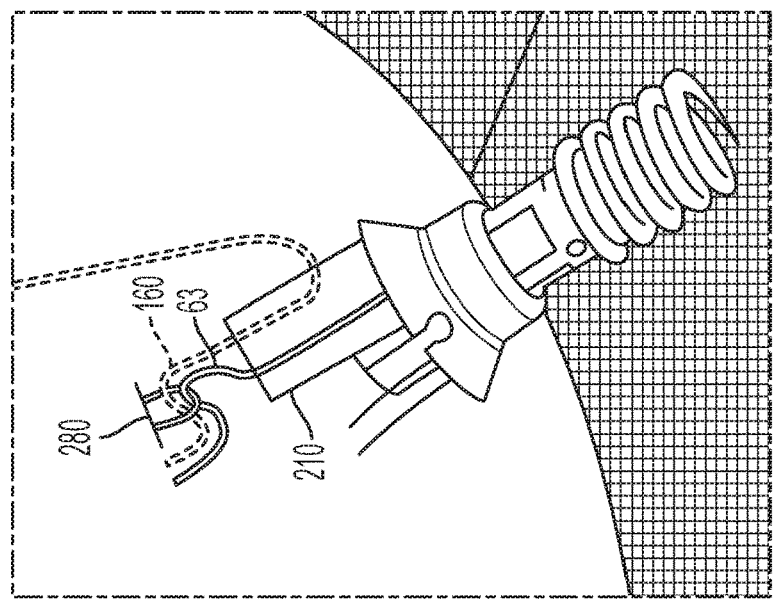
FIG. 43A
FIG. 43B

DEVICES FOR TRANSCATHETER CHORDAL IMPLANTATION AND METHODS OF IMPLANTATION

CROSS REFERENCE TO RELATED APPLICATIONS

This application claims priority to US Provisional Patent App. No. 62/914,357 filed Oct. 11, 2019, the disclosure of which is herein incorporated by reference.

FIELD OF THE INVENTION

The present invention relates generally to a medical assembly for restoring chordal support of a heart valve by implanting artificial chordae tendinae in the heart; one or more chords attach one or both mitral leaflets to at least one anchor device, which is implanted in any wall or papillary muscle of the left ventricle. The present invention also relates to methods of implantation of components of the medical assembly. More specifically, the invention pertains to a trans-septal guide catheter, anchor delivery system, anchor device, anchor line swivel, anchor lines, leaflet grasper, chords, reversible locks, and anchor line/chord crimper, as well as methods related to such assembly for endovascularly implanting the artificial chords in the heart and attaching them to the mitral valve, thereby restoring the function of the native mitral valve.

BACKGROUND OF THE INVENTION

Mitral valve disease, primarily causing mitral regurgitation (MR), results from either a primary degeneration of the valve (e.g. myxomatous degeneration, endocarditis, rheumatic disease, congenital disease, or other causes), or from incomplete leaflet coaptation (secondary or "functional" mitral regurgitation). MR increases left atrial pressure, causing pulmonary congestion, thereby leading to signs and symptoms of congestive heart failure, namely peripheral edema, orthopnea, paroxysmal nocturnal dyspnea, and progressive dyspnea on exertion. Additionally, MR exacerbates left ventricular dysfunction, decreasing survival. Because many patients suffering MR have significant comorbidities and have high surgical risk, developing minimally invasive (i.e. transcatheter) methods to treat MR is important.

For mitral regurgitation resulting from primary degeneration of the mitral valve, surgical mitral valve repair remains the gold standard. An important component of repair is the implantation of neo chordae into the heart with fixation to one or both mitral leaflets to support native chordae that are either elongated or ruptured. Developing transcatheter approaches for neo chordae implantation is important, not only for patients with co-morbidities that render them intermediate or high risk for open heart surgery, but also for patients that are low risk for surgery who may benefit from a quicker recovery time.

The current transcatheter devices being developed have important limitations such as inability to adjust chordal length easily during implantation, difficulty in being able to implant multiple chords, inability to adjust chordal length after implantation (i.e. inability to adjust chordal length after multiple chords have been implanted), or need for surgical access. For example, both the NeoChord (NeoChord, Inc., St. Louis Park, Minnesota, USA) and Harpoon devices (Edwards LifeSciences, Irvine, CA, USA) require a lateral thoracotomy and trans-apical incision of left ventricle.

Percutaneous devices avoid this risk by being delivered via a trans-septal approach. For example, the ChordArt system (CoreMedic, Biel/Bienne, Switzerland), allows trans-septal implantation of neo-chordae. The system, however, requires the operator to select the length of the chord prior to implantation, because chordal length cannot be changed during implantation.

Unlike the ChordArt system, the Pipeline Medical (W.L. Gore and Associates, Inc., Newark, Delaware, USA) and the CardioMech (CardioMech, Trondheim, Norway) systems allow chordal adjustment during implantation. Although all three systems allow multiple chords to be implanted, the ChordArt and CardioMech systems require a separate anchor for each chord, which requires hunting for multiple anchoring sites, which can be technically challenging, and which increases the risk of anchor dislodgement. Finally, in all three systems once an individual chord is implanted and adjusted, it cannot be readjusted after the placement of another chord.

Accordingly, it remains desirable in the pertinent art to provide a system for transcatheter chordal implantation that is fully percutaneous (i.e. trans-septal), facilitates multiple chord placement with low risk of anchor dislodgement, allows chordal length adjustment during implantation, and allows chordal length adjustment even after implantation. Thus, after the implantation of multiple chords, length of any chord can be re-adjusted before final release.

SUMMARY OF THE INVENTION

Presented herein is a medical assembly that is implanted minimally invasively across the mitral valve for implantation of artificial chords to restore the function of the native mitral valve. The method disclosed herein implants the chords via trans-septal access, and the chords connect one or both mitral leaflets to at least one anchor, which is attached to any intraventricular wall and/or papillary muscle of the left ventricle. Accordingly, and beneficially, no portion of the system requires surgical thoracotomy or trans-apical access for implantation.

In one aspect, the system comprises a steerable trans-septal guide that allows delivery of an anchor delivery system into the left ventricle, with delivery of at least one anchor into any wall and/or papillary muscle of the left ventricle.

The system further comprises an anchor line swivel that allows rotational freedom of one or more anchor lines about the central access of the anchor. The anchor lines may consist of single lines attached to the end of anchor line rods of the anchor line swivel, or may consist of loops of lines running through a channel in each of the anchor line rods. The anchor line swivel may be delivered over a guidewire connected to the anchor until it docks onto the anchor, or the anchor line swivel may be pre-attached to the anchor and both are delivered as a unit to the desired intraventricular wall and/or papillary muscle of the left ventricle.

The system further comprises a leaflet grasper that advances over one of the anchor lines and grasps a mitral leaflet. Inside the leaflet grasper, a chord is contained within the central channel of the puncturing rod. "Proximal end" of the chord is defined as the portion of the chord that will abut the superior (or atrial) surface of the leaflet. The "proximal end" of the channel or puncturing rod is the portion closest to the leaflet grasper control handle, which is outside the body. Therefore, the proximal end of the chord has a preformed knot or pledget and is contained inside the proximal end of the channel within the puncturing rod. The distal end of the chord is immediately outside the distal end of the puncturing rod and is attached to a puncturing element, which abuts the distal end of puncturing rod, but is not attached to it. Once the leaflet is grasped, the puncturing rod drives the puncturing element and attached chord through the superior (or atrial) surface of leaflet into the receiving chamber in the inferior portion of the leaflet grasper. The puncturing element couples to a receiving cap within the receiving chamber, and the puncturing rod is retracted from the receiving chamber, leaving a preformed knot or pledget of the chord above the superior (or atrial) surface of the leaflet, with the rest of the chord passing through the leaflet and coupled to the receiving cap in the receiving chamber.

After coupling, the receiving cap is withdrawn by a retracting rod back up the shaft of the leaflet grasper out of the body, thereby withdrawing the puncturing element and the attached end of the chord out of the body. The proximal end of the chord is restrained on the superior (atrial) side of the grasped leaflet by a preformed knot, or by a pledget.

The system further comprises a chord release tube, integrated within the leaflet grasper, which advances over the chord out the bottom of the leaflet grasper, thereby allowing the chord to move out of a split seam that wraps around the side of the grasper arm to the bottom of the leaflet grasper. Once the chord is freed from the grasper arm, the leaflet grasper can translate freely over both the anchor line and chord, and can be retracted out of the body. The anchor line and chord remain attached to the anchor and leaflet, respectively, and are accessible outside the body.

The system further comprises chord locking tubes that consist of proximal positioning rods, and distal detachable and reversible locks. Over any anchor line and associated chord, a proximal positioning rod pushes a detachable lock over each anchor line and associated chord, which run through a central lumen of the positioning rod, until the lock meets the end of an anchor line rod of the anchor line swivel. At this point, while the positioning rod provides counterforce, the chord may be pulled through the lumen of the lock and positioning rod until appropriate tension of the leaflet is obtained. Then, the lock may be deployed by pulling a hypotube within the positioning rod, thereby engaging a collet within the lock, which clamps onto the anchor line and chord. The positioning rod may then be unscrewed from the lock and withdrawn into the left atrium, and the anchor line and chord proximal to the lock can slacken. Therefore, the rod and the anchor line or chord do not interfere with the mitral valve coaptation, and one can assess the true residual mitral regurgitation. If re-adjustment of chord tension needs to occur, the positioning rod is re-advanced and screwed into the distal lock. Pushing the internal hypotube disengages the collet within the lock, which allows free movement of the chord again. Because this entire process can be repeated with other chords, multiple chords can be attached to one or more leaflets and secured to the ends of the anchor line rods of the anchor line swivel by reversible locks, and any or all of the chords can be re-adjusted multiple times after implantation.

In another embodiment, the reversible locks are advanced by the positioning rods but are not activated by them. Instead of having one central lumen, these locks have one lumen through which the chord runs ("chord lumen"), and a second lumen through which the anchor line runs ("anchor line lumen"). The positioning rod pushes the lock over both the anchor line and chord until the lock docks onto the anchor line rod of the anchor line swivel. At this point the positioning rod disengages from the lock, and is retracted into the left atrium. Through the chord lumen, the chord can be pulled to tension the leaflet and this tension is retained within the lock ("self-locking"). To release tension, the anchor line is pulled, which brings an unlocking element attached to the anchor line into the anchor line lumen. The unlocking element pushes a plate that releases the lock and allows free movement of the chord through the chord lumen. The anchor line is allowed to translate relative to the anchor line rod by being attached to the rod with a spring internal or external to rod. When the anchor line is released and pulled back down by the spring, the unlocking element leaves the anchor line lumen, and the lock re-engages. Alternatively, a loop of anchor line goes through a channel running through the side of the rod, which allows the line to pulled by either end, thereby translating up or down relative to the rod. In this case, to unlock the chord lumen, the unlocking element attached to one side of the line is pulled into the anchor line lumen, thereby pushing a plate to release the lock. To allow the self-locking mechanism to re-engage, the line can be pulled from the other side, thereby pulling the unlocking element out of the anchor line lumen, which allows the plate to spring back to the locked position.

In another embodiment, the reversible lock is not "self-locking" but is locked/unlocked by pulling the anchor line. A "push button" element, attached to the anchor line, is pulled into the anchor line lumen, engaging the lock, and then is automatically retracted down by a spring attaching the anchor line to the anchor line rod. To unlock the lock, the push button element is retracted back again into the anchor line lumen, thereby unlocking the lock. Alternatively, a loop of anchor line goes through a channel running through the side of the rod; pulling one end of the line brings a push button element into the anchor line lumen, thereby locking the lock. Retracting the other end of the line pulls the push button element out of the anchor line lumen, and pulling the anchor line attached to the push button a second time brings the push button element back into the anchor line lumen, thereby unlocking the lock. To maintain tension on the chord during chord adjustment and unlocking/locking, the end of the chord (outside the body) is connected to a chord adjustment control of a chord tension board. Pulling or pushing the chord adjustment control increases or decreases the tension, respectively, and maintains that degree of tension until re-adjusted. To facilitate ease of locking or unlocking, the anchor line is placed in an anchor line lock/unlock control. Pulling the anchor line lock/unlock control pulls on the anchor line, locking the lock, and springing back to initial position. Pulling the anchor line lock/unlock control a second time pulls the anchor line, unlocking the lock. Alternatively, if a loop of anchor line is used to lock or unlock the lock, the push button end of the anchor line loop can be placed in an anchor line lock/unlock control, and the unlocking end of the anchor line loop can be placed in an anchor line release control.

In another embodiment, instead of deploying a reversible lock, the positioning rod deploys a chord tension regulator. The chord tension regulator has a chord lumen and an anchor line lumen. The positioning rod pushes the chord tension regulator until it docks onto the anchor line rod, and then the positioning rod is unscrewed from the chord tension regulator and retracted into the left atrium. The proximal chord is attached to a chord adjustment control of a chord tension board and pulling or pushing the chord adjustment control pulls or pushes the chord through the chord lumen of the chord tension regulator, thereby increasing or decreasing tension on the leaflet, respectively, and maintains that degree of tension until readjusted. These steps can be repeated with other implanted chords. Therefore, multiple chords can be adjusted simultaneously. To lock any particular chord in place, an anchor line/chord crimper wraps around the proximal anchor line/chord outside the body, advances over both until it reaches the chord tension regulator, then crimps the line and chord together with a metallic clip and simultaneously cuts the line and chord, thereby fully releasing them. According to any alternative, including a removeable self locking or non-self locking or chord tension regulator, a line gathering member is provided to encompass the chord and anchor line.

In another aspect, the anchor line/chord crimper is used in either of the two reversible lock embodiments. Specifically, the anchor line/chord crimper wraps around the proximal anchor line/chord outside the body, advances over both until it reaches the reversible lock, then crimps the line and chord together with a metallic clip and simultaneously cuts the line and chord, thereby fully releasing them.

Related methods of implantation are also provided. Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical assembly that is implanted minimally invasively in the heart, and be protected by the accompanying claims.

DESCRIPTION OF THE FIGURES

FIG. 4A is a perspective view of an anchor line swivel for connecting single anchor lines to the anchor;

FIG. 4B is a perspective view of an anchor line swivel for connecting loops of anchor lines to the anchor;

FIG. 5A is a perspective view of the anchor/chord assembly, comprised of the anchor line swivel for connecting single anchor lines to anchor, coupled to the anchor, for anchoring chords to a cardiac wall or papillary muscle;

FIG. 5B is a perspective view of the anchor/chord assembly, comprised of the anchor line swivel for connecting loops of anchor lines to anchor, coupled to the anchor, for anchoring chords to a cardiac wall or papillary muscle;

FIG. 9A is a side elevational view of the anchor delivery system, housing anchor assembly of FIG. 5A, according to one aspect;

FIG. 9B is a magnified side elevational view of the anchor delivery system of FIG. 9A;

FIG. 9C is a plan view of the anchor delivery system of FIG. 9A;

FIG. 10A is a side elevational view of the anchor delivery system, housing anchor assembly of FIGS. 6A-F, according to one aspect;

FIG. 10B is a magnified side elevational view of the anchor delivery system of FIG. 10A;

FIG. 11A is a perspective view of the anchor delivery system of system of FIG. 9A or 10A, in which a portion of the device is positioned in the left ventricle;

FIG. 11B is a perspective view of the anchor delivery system of FIG. 10A, in which the anchor delivery system is delivering a portion of the anchor, connected to the anchor assembly of FIGS. 6A-F, into the left ventricle;

FIG. 11C is a magnified side elevational view of the anchor, connected to anchor assembly of FIGS. 6A-F, being delivered into the left ventricle;

FIG. 13A is a side elevational view of the leaflet grasper with grasper arm closed;

FIG. 13B is a side elevational view of the leaflet grasper with the grasper arm open;

FIG. 14A is a magnified side elevational view of the distal end of the leaflet grasper when the grasper arm is open;

FIG. 14B is a perspective view of the distal end of the leaflet grasper when the grasper arm is open;

FIG. 14C is a side elevational view of the puncturing rod and puncturing element;

FIG. 14D is a side elevational view of the receiving cap and retracting rod;

FIG. 32A is a cross-sectional perspective view of the collet locking system locked and released;

FIG. 32B is an intact perspective view of the collet locking system locked and released;

FIG. 35A is a cross-sectional side elevational view of the self-locking lock in the locked position;

FIG. 35B is a cross-sectional side elevational view of the self-locking lock in the unlocked position;

FIG. 37 is a cross-sectional side elevational view the chord tension regulator;

FIG. 39A is a cross-sectional side elevational view of the locking/unlocking lock in the unlocked position;

FIG. 39B is a cross-sectional side elevational view of the locking/unlocking lock in the locked position;

FIG. 40B is a side elevational view of the anchor line/chord crimper with the grasper hook pulled in;

FIG. 41A is a cross-sectional perspective view of the anchor line/chord crimper with the grasper hook ready for anchor line/chord insertion;

FIG. 41B is a cross-sectional perspective view of the anchor line/chord crimper with the anchor line/chord inserted into the grasper hook;

FIG. 41C is an enlarged perspective from FIG. 41A;

FIG. 43A is a cross-sectional perspective view of the anchor lock secured to anchor line and chord;

FIG. 43B is a magnified cross-sectional perspective view of the anchor lock secured to the anchor line and chord;

DESCRIPTION OF THE INVENTION

Figure 1:
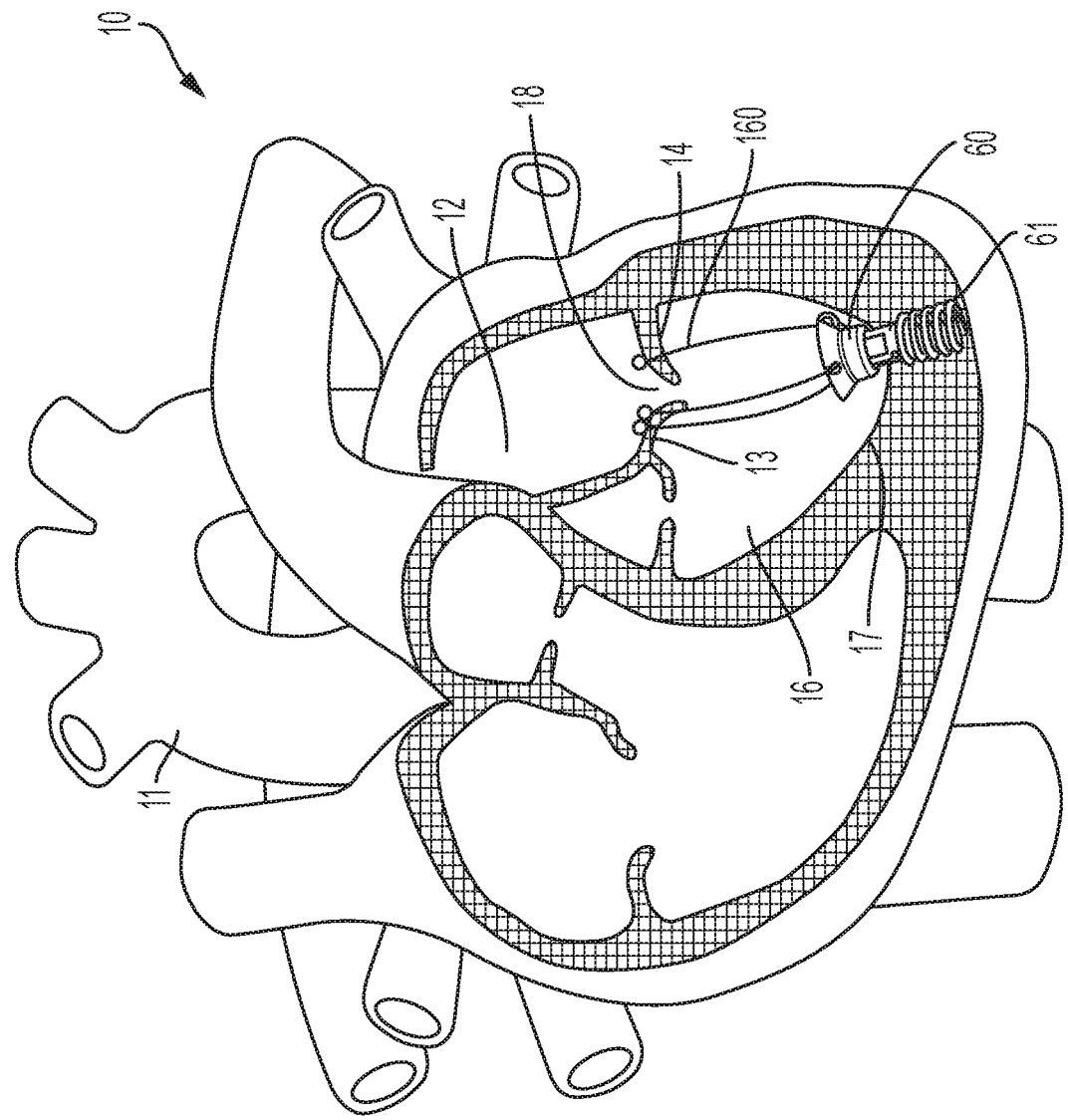
FIG. 1 is a cross-sectional perspective view of a heart showing the transcatheter chordal system of the present application positioned in the heart, according to one aspect.

The present invention is understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes are made to the aspects described, while still obtaining the beneficial results of the present invention. It will also be apparent that some of the desired benefits of the present invention is obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges is expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. For the purposes of describing and defining the present invention it is noted that the use of relative terms, such as "substantially", "generally", "approximately", and the like, are utilized herein to represent an inherent degree of uncertainty that is attributed to any quantitative comparison, value, measurement, or other representation. These terms are also utilized herein to represent the degree by which a quantitative representation may vary from a stated reference without resulting in a change in the basic function of the subject matter at issue.

Figure 2:
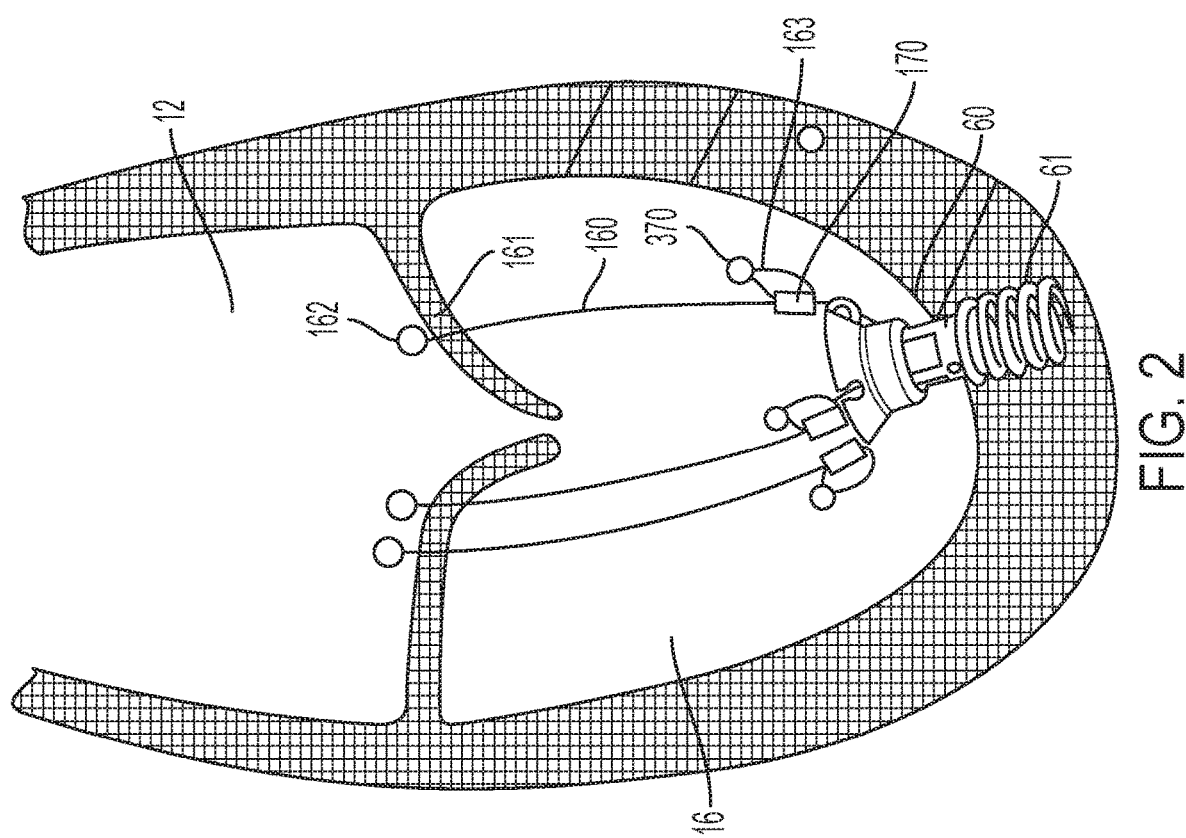
FIG. 2 is a magnified cross-sectional perspective view of a left atrium and left ventricle of a heart showing the transcatheter chordal system of the present application positioned in the heart, according to one aspect.

The disclosure herein relates to a medical assembly 10 for implanting one or more chords minimally invasively in the heart 11 to restore chordal support to either the anterior mitral leaflet 13, the posterior mitral leaflet 14, or to both. FIG. 1 illustrates the chords 160 which have been implanted to support the anterior mitral leaflet 13 and the posterior mitral leaflet 14 to prevent either leaflet from prolapsing from the left ventricle 16 into the left atrium 12. The assembly comprises chords 160 which anchor the mitral leaflets to the anchor assembly 40 or 41, consisting of the anchor line swivel 50 or 51 (see FIGS. 4A and 4B), and anchor 20, which has affixed to an intracardiac wall 17. FIG. 2 is a magnified view of heart 11, showing only the left atrium 12 and the left ventricle 16. This figure further shows that each chord 160 has a proximal end 161 restrained on the atrial side of either leaflet by knot or pledget 162. The distal end 163 of the chords 160 are attached to the anchor line rods 54 of the anchor assembly 40 or 41, by reversible locks 176, 190 or 220 or chord tension regulator 210. The anchor line 52 or 53 has been crimped together to the distal end 163 of chord 160 by the anchor line/chord crimper 260 (FIG. 40A). The medical assembly 10 includes an anchor delivery system 92, leaflet grasper 130, reversible locks [176, 190, or 220] or chord tension regulator 210, and anchor line/chord crimper 260. The method for implanting the chord and anchoring the mitral leaflets to the intracardiac wall as herein shown and described includes, generally, the method of steps of: using the anchor delivery system 92 to deliver the anchor assembly 40 or 41 to an intracardiac wall 17; using the leaflet grasper 130 to grasp one mitral leaflet at a time to pass a chord 160 through the leaflet; delivering the reversible locks or chord tension regulator over the anchor line 52 or 53 and chord 160 until the reversible locks or chord tension regulator reaches the anchor line rod 54 or 78; tensioning the chord 160; assessment residual mitral regurgitation on echocardiography and leaving chord 160 as is, or re-adjusting tension, with the possibility of implanting one or more additional chords and re-adjusting tension of one or all of them; advancing the anchor line/chord crimper and cutter over the externalized anchor line (s) 52 or 53 and chord (s) 160 to the reversible locks or chord tension regulator; crimping the anchor line 63 and distal end(s) 163 of chord(s) 160 together and cutting both proximal to the reversible locks or chord tension regulator, thereby leaving the implanted chord (s) 160 in place to support the function of the mitral leaflets.

Anchor Assembly (Anchor and Anchor Line Swivel)

Figure 3B:
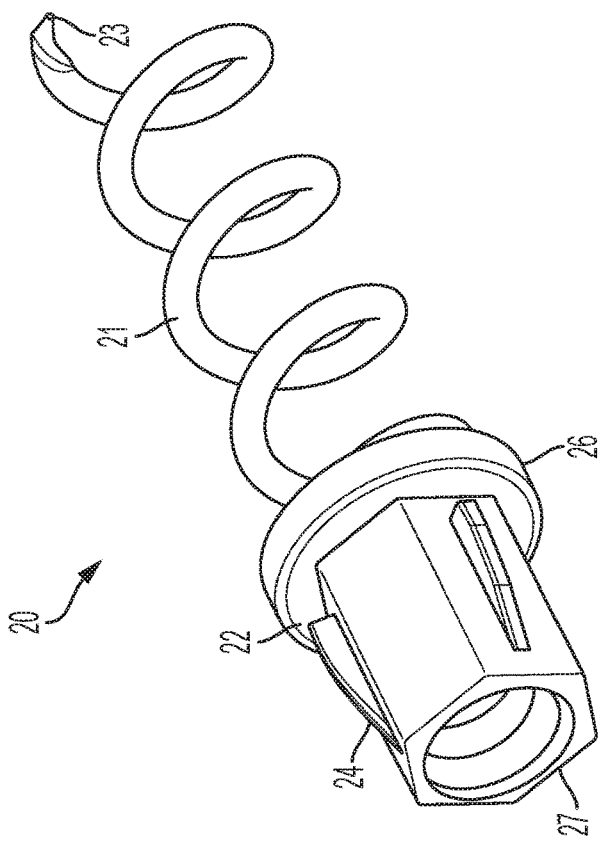
FIG. 3B is a perspective view of an anchor for anchoring chords to a cardiac wall or papillary muscle.
Figure 3A:
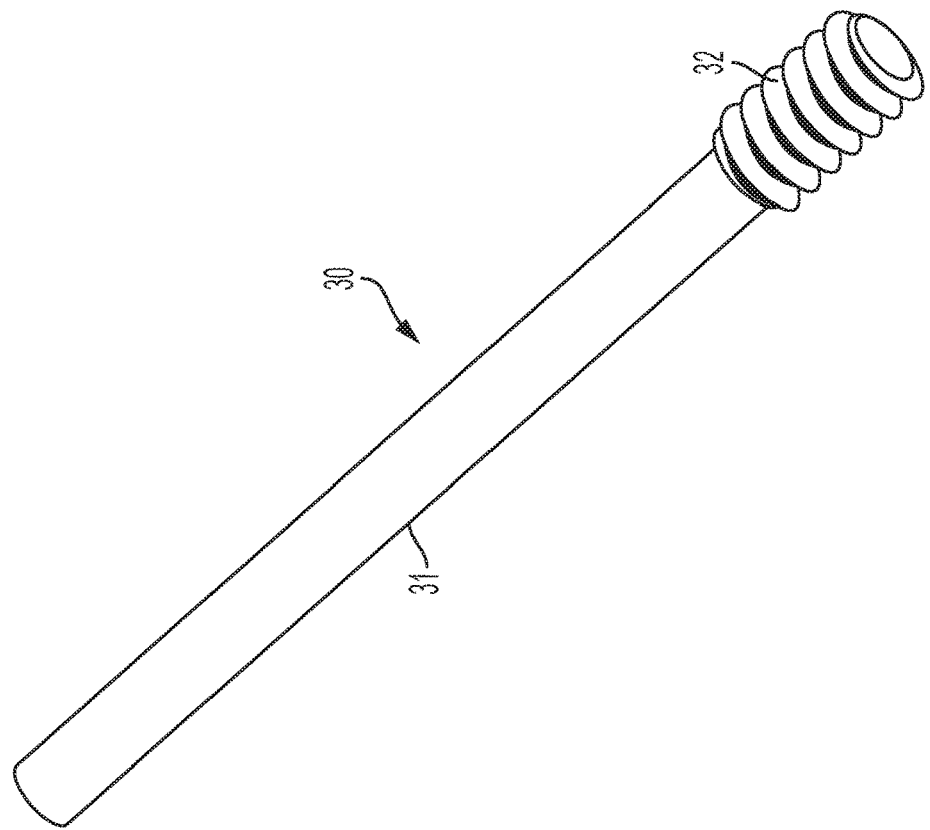
FIG. 3A is a perspective view of the delivery cable of the anchor for anchoring chords to a cardiac wall or papillary muscle.

The components of anchor assembly 40 or 41 shown in FIGS. 3-5 include an anchor 20, which consists of an anchor in the form of an anchor screw 21 as shown and an anchor cap 22, and an anchor line swivel 50 or 51, which is either pre-attached to anchor 20 or delivered over delivery cable 30, which maintains control of anchor assembly 40 or 41 during placement. In one aspect, the anchor screw is coupled to and extends from the distal end 26 of the anchor cap 22. At the proximal end 27 of anchor cap 22, the flexible wire 31 of the delivery cable 30 is removably connected by its distal end 32 to the proximal end 27 of the anchor cap 22. The flexible wire 31 is constructed of, but not limited to, stainless steel, nitinol, or other metal alloys, with or without hydrophilic coatings, or with or with a polymer coating as a polytetrafluoroethylene (PTFE). The distal threaded end 32 is sized and configured to selectively engage complementary threads formed in a cavity defined in the proximal end 27 of the anchor cap 22. In use, the distal threaded portion 32 has been pre-attached into the proximal end 27, coupling the anchor cap 22 to the distal end of the flexible wire 31. As described later, once the anchor assembly 40 or 41 has been implanted, the distal threaded end 32 is unscrewed from the proximal end 27 of the anchor 20, detaching the flexible wire 31 from the anchor assembly 40 or 41.

Attached to the end of the anchor assembly 40 or 41, the anchor screw 21, as shown, is sized and configured as a helical screw to affix to an intracardiac wall. Optionally, however, the anchor screw 21 may be differentially sized (longer or shorter depending on the cardiac wall to which it attaches) and configured as an inclined plane (such as an Archimedes-type screw), nail-like head, or as any other type of screw that would be known to those skilled in the art, and can be "right handed" or "left handed". In one aspect, the screw is composed of any know metal alloy, including, but not limited to, nitinol, titanium, or cobalt-chromium. In another aspect, the metal alloy of the anchor screw 21 may be coated with biological tissue, such as bovine, ovine, porcine, or equine pericardium, or with any combination of anti-inflammatory drugs that might promote healing and limit inflammation. A tip 23 of the anchor screw 21 optionally is constructed of and/or coated with the same or different materials as the anchor screw 21, and may be fashioned as a blunt or sharp tip. In a further aspect (not shown), rather than the anchor screw 21, a fixation mechanism composed of, but not limited to, nitinol, stainless steel, cobalt-chromium, or titanium alloys, the in the shape of barbs, hooks, prongs, and like is positioned at the distal end 26 of anchor cap 22 to securely attached the anchor assembly 40 or 41 to intracardiac wall 17.

In use, the anchor 20 is secured to the intracardiac wall by rotating the anchor screw 21 until tip 23 is at the desired depth in the cardiac wall. The depth to which the anchor screw 21 is screwed in is adjustable according to the location within the heart. For example, the anchor screw 21 may be implanted more deploy into the interventricular septum, for greater fixation, as opposed to the ventricular free wall (i.e. epicardial wall), where a shallower implantation is safer. By reversing the rotation of anchor screw 21, the anchor 20 is removed safely from the cardiac wall, either to be repositioned, or removed entirely.

The anchor 20, via anchor cap 22, is configured to accept an anchor line swivel 50 or 51, which is either pre-attached before anchor delivery, or may be delivered separately over delivery cable 30 after anchor delivery. To allow this, the anchor cap 22 comprises at least one locking arm 24. The locking arm 24 is sized and configured for releasably securing a portion of the anchor line swivel 50 or 51 (described below) to the anchor cap 22. The at least one locking arm 24 moves between a first locked position, in which the locking arm 24 extends a first distance away from the body of the anchor cap 22, and a second unlocked position in which the locking arm 24 extends a second distance away from the anchor cap 22 that is less than the first distance. The anchor cap 22 comprises at least one biasing member (not shown), such as a spring, configured to urge each locking arm 24 to the first locked position. As shown, a plurality of locking arms 24 are provided and are spaced equally around the circumference of the anchor cap 22, though it is contemplated that the locking arms 24 need not be equally spaced.

Over these locking arms 24 the anchor line swivel 50 or 51 is configured to attach to the anchor cap 22, either pre-attached before delivery of anchor to the interventricular wall (preferred embodiment), or delivered separately after anchor is delivered over flexible wire 31 of delivery cable 30.

As shown in FIG. 4A or 4B, in one aspect, the anchor line swivel 50 or 51 comprises a docking ring 59 coupled to or formed monolithically to one or more docking ring arms 58. As shown, the plurality of docking ring arms 58 are spaced equally around the circumference of the docking ring, though it is contemplated that the docking ring arms 58 need not be spaced equally. Each docking ring arm 58 has a terminal eyelet 57 that is configured to operate with an anchor rod hook 56 defined by the end of each anchor line rod 54 as shown, and the anchor rod hook 56 is either coupled to or formed monolithically with the distal end of each anchor line rod 54.

In another aspect the anchor rod hook 56 and eyelet 57 are sized and configured so that the anchor rod hook 56 is inserted into the eyelet 57 to securely, rotatably couple the distal end of an anchor line rod 54 to a respective proximal end of each docking ring arm 58 of the docking ring 59. In use, each anchor rod hook 56 rotates about the circumference of the eyelet 57. As shown in FIGS. 4A and 4B, the proximal end of either anchor line rod is coupled to an anchor line, which may be a single anchor line 52 with or without connection to the anchor line rod by an external or internal spring (not shown), or may be a loop of anchor line 53 running through a side channel 55 of the anchor line rod 54. Each anchor line can consist of, but not be limited to, expanded polytetrafluoroethylene (ePTFE) or ultra-high-molecular-weight polyethylene (UHMWPE or UHMW).

FIGS. 5A and 5B show the final configuration of anchor assembly 40 or 41. The anchor assembly is either formed prior to anchor delivery (pre-attached) or created after anchor 20 delivery. In either case, the anchor line swivel 50 or 51 is advanced over flexible 31 of delivery cable 30 (during manufacturing if pre-attached), and the docking ring 59 of the anchor line swivel 50 or 51 depresses the at least one locking arm 24 of the anchor cap 22 to the second unlocked position. With the locking arm 24 in the second position, the anchor line swivel 50 or 51 advances over the locking arm 24 on the anchor cap 22 until the docking ring 59 abuts and/or is adjacent to a distal end 26 of the anchor cap 22. At this point, the biasing member of the anchor cap 22 urges the at least one locking arm 24 to the first locked position, thereby releasably coupling the docking ring 59, and the rest of the anchor line swivel 50 or 51, to the anchor 20.

In one aspect, when coupled to anchor 20, the anchor line swivel 50 or 51 rotates about a longitudinal axis of the anchor a full 360 degrees. Optionally, in another respect, the anchor line swivel 50 or 51 may be constrained to lesser degrees of rotation by interaction of a portion of the anchor line swivel 50 or 51 with the at least one locking arm 24.

Halo Anchor Assembly

According to another aspect of the disclosure, as shown in FIGS. 6A-F, an anchor assembly 60, is illustrated. The halo anchor assembly can have the anchor line swivel pre-attached to the anchor, or attached after anchor is delivered. The halo anchor assembly 60 includes an anchor shaft 66 and an anchor screw 61. As shown, the anchor screw 61 has a helical configuration and extends distally from an anchor screw base 62. The anchor screw base 62 defines at least one, or a plurality as shown, of anchor flanges 63 and recessed areas 64 therebetween. The anchor shaft 66 includes at least one or, as shown, a plurality of locking members 67 shown in FIG. 6B. Locking members 67 are biased, such as by a spring (not shown), radially outwardly from the anchor shaft 66. A delivery cable in the form of an anchor connector 69 and anchor rod 71 cooperate with the anchor shaft 66 to rotate the anchor screw 61. The anchor connector 69 defines at least one or, as shown, a plurality of apertures 68 configured for receipt of the anchor flanges 63. Accordingly, the anchor connector 69 and connector rod 71 are matingly connected to the anchor shaft 66, thereby urging the locking members 67 inward. The cooperating of the apertures 68 and flanges 63 integrate the anchor connector 69 the anchor screw base 62. Rotation of the connector rod 71 thereby rotates the anchor screw 61 for interventricular or epicardial implantation into the an intracardiac wall.

Figure 6A:
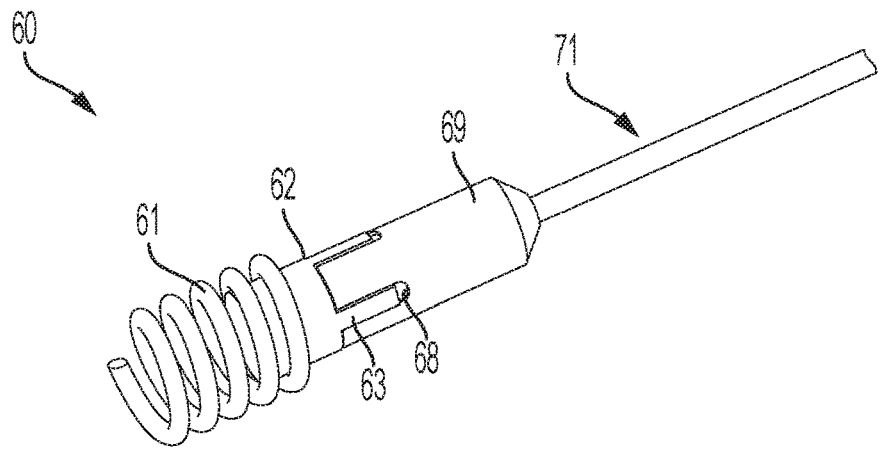
FIGS. 6A-6F are perspective views of an anchor according to another aspect having an anchor screw and anchor cap configured for receipt of connecting ring and a tethering system illustrated in sequential steps.
Figure 6B:
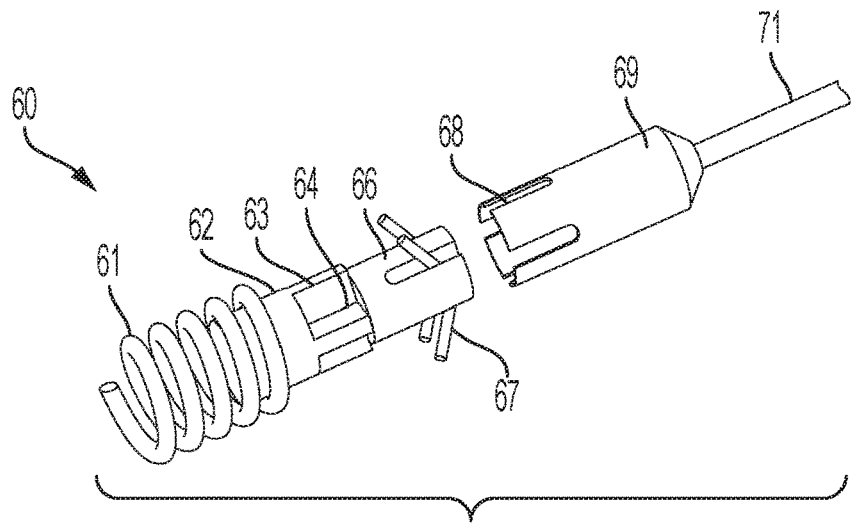
Figure 6C:
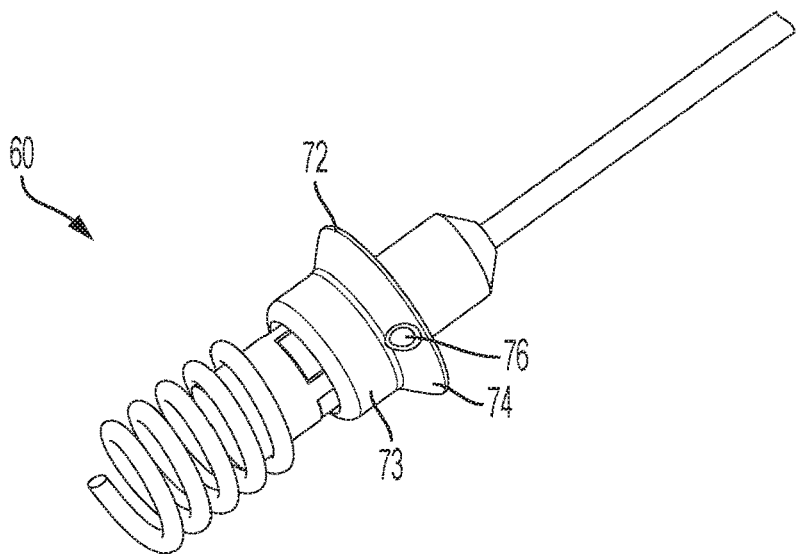
Figure 6D:
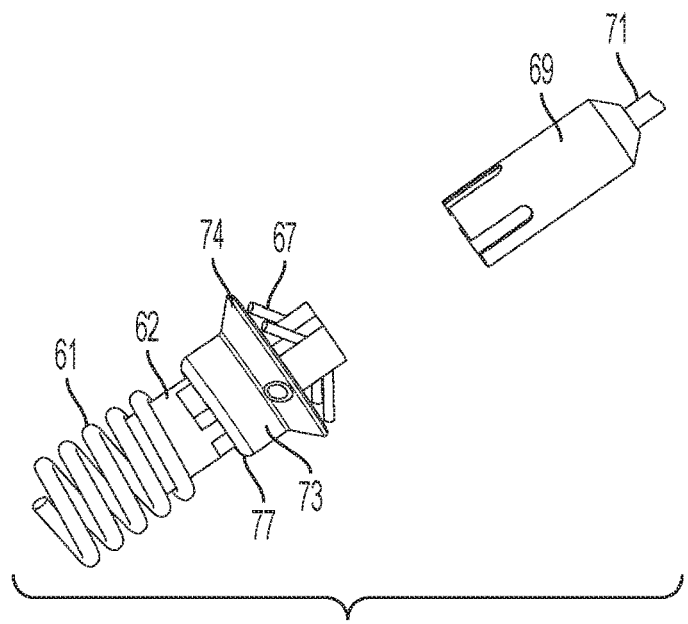
Figure 6E:
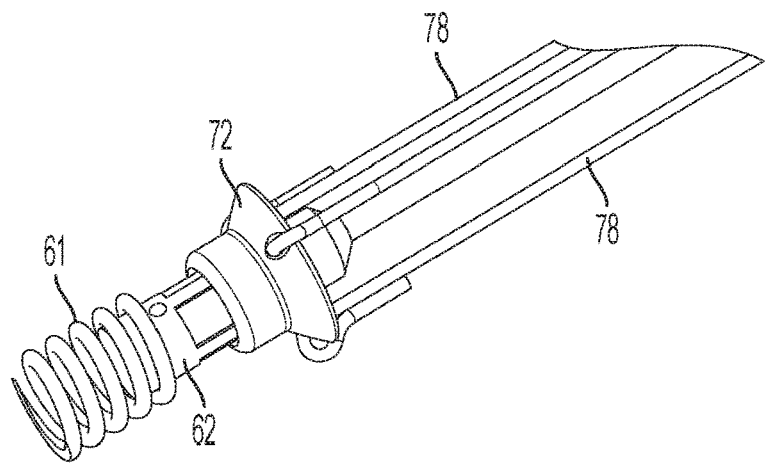
Figure 6F:
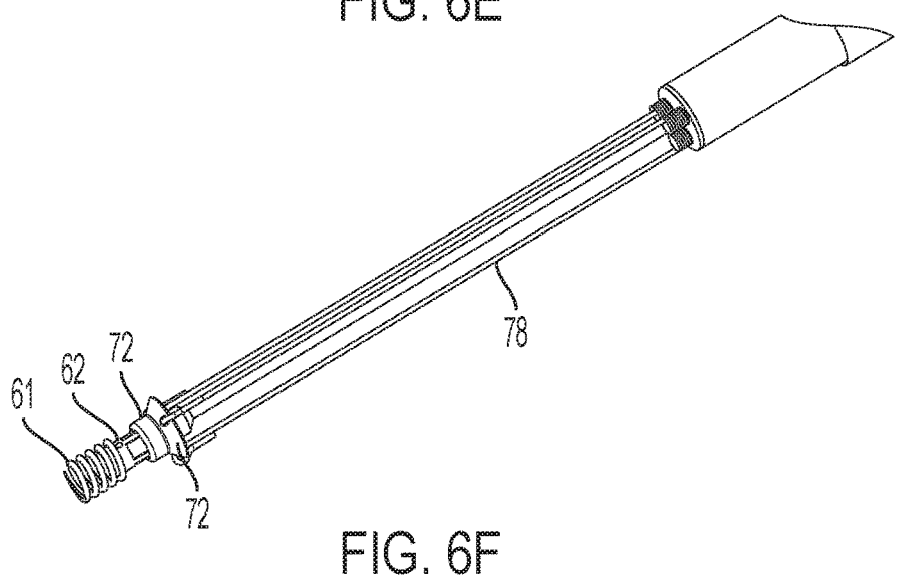

It is the preferred embodiment that the tether ring 72 has been pre-attached to the anchor screw 61. If not, then after the anchor screw 62 has been implanted, a docking ring 72 is applied over the connector rod 71 and anchor connector 69 and abuts the proximal end of the anchor screw 61. The docking ring 72 includes a generally cylindrical first distal portion 73 and a second proximal portion 74 having a diameter greater than the first portion 73. The second portion 74 defines at least one or, as shown, a plurality of apertures 76 configured for receipt of anchor line rods 78 as shown in FIGS. 6E and 6F. As in shown in FIG. 6D, the anchor connector 69 and anchor connector rod 71 are removed. The locking members 67 are urged radially outward so as to engage the second portion 74 of the docking ring 72 to lock the docking ring 72 on the anchor screw base 62. The anchor line rods 78 are attached to either a single anchor line (not shown) via an internal or external spring (not shown), or to a loop of anchor line (not shown) via a side channel in the anchor line rods 78.

Figure 7:
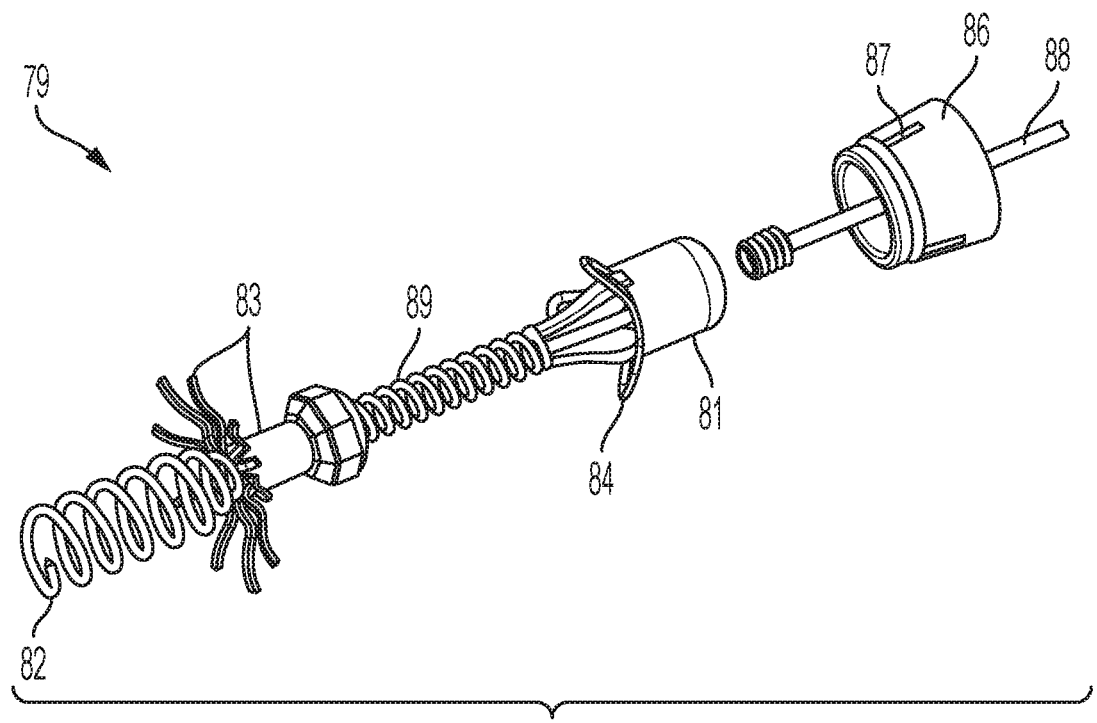
FIG. 7 is an exploded view of an anchor having an anchor screw and anchor cap configured for receipt of connecting ring and a tethering system according to another aspect of the invention.
Figure 8:
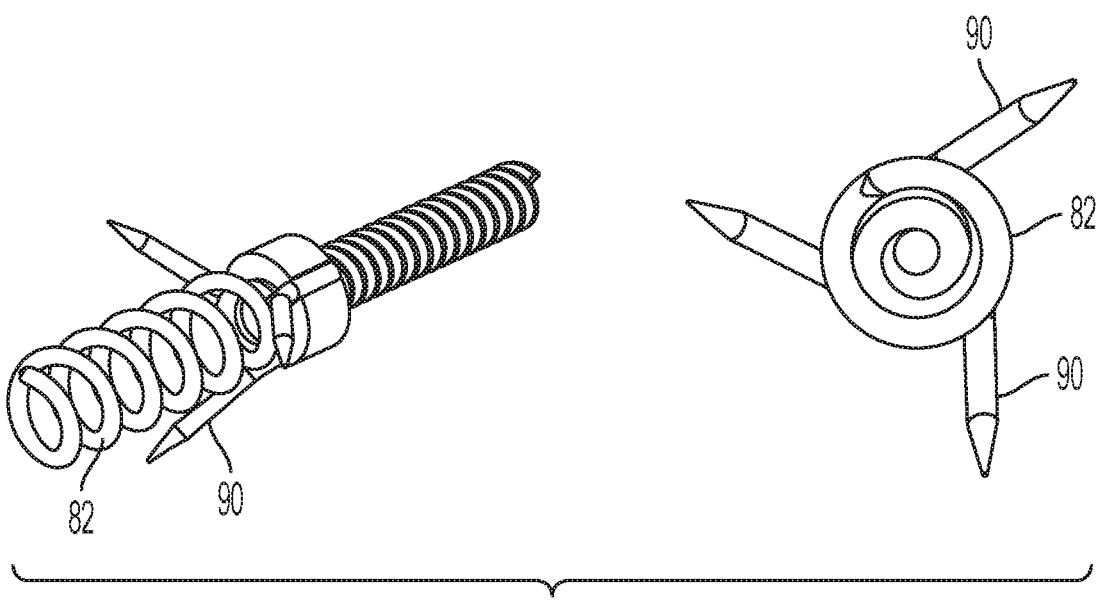
FIG. 8 is a perspective view and plan view of the anchor of FIG. 7 with stabilizers according to another aspect of the invention.

Another aspect of the halo anchor assembly is shown in FIGS. 7 and 8. The anchor assembly 79 additionally includes a flex connector 89 extending between anchor shaft 81 and the anchor base 83. This permits anchor assembly 79 and chord to remain axially aligned with the mitral valve leaflets (such as, parallel to the interventricular septum), particularly when the anchor screw 82 is implanted in an intracardiac wall this is not directly perpendicular to the mitral valve annular plane. As shown, the flex connector 89 is a coiled configuration, but other configurations are envisioned. Flex connector 89 may be formed of a suitable material such as a metal or metal alloy.

The anchor assembly 79 shown in these drawings also includes stabilizers 90 to stabilize the anchor and limit or prevent movement, such as rotational movement, from tension transferred from the tethers and to provide traction to limit or prevent the anchor screw 82 from inadvertently rotating so as to uncouple from the tissue in which is was implanted. At least one stabilizer 90 may be provided. As shown in FIG. 7, eight stabilizers 90 are illustrated and FIG. 8 illustrates three. As shown in FIG. 7, the stabilizers 90 extend radially outward from the longitudinal axis of the anchor. The stabilizers 90 are configured to have a non-linear configuration. Other configurations are envisioned. The stabilizers 90 shown in FIG. 8 also extend radially outwardly from the anchor longitudinal axis and extend at an acute angle, for example 45 degrees, along the horizontal axis. The angle is generally facing the opposite direction of the anchor screw 82. The stabilizers are generally linear, but other configurations are envisioned. When inserted into any intracardiac wall, for example, the stabilizers 90 urge against perhaps into the tissue in a direction opposition the anchor screw 82 implantation to prevent unintentional withdrawal of the anchor screw 82.

Anchor Delivery System

Referring to FIGS. 9A-C, the anchor delivery system 92 for positioning and deploying the anchor cap 22 of anchor assembly 40 or 41 is illustrated. The anchor delivery system 92 comprises an anchor delivery guide 93 and an anchor delivery rod 94. In this aspect, the anchor delivery guide 93 has a distal end 96, an opposed proximal end 97 and an inner guide lumen 98, extending between the anchor delivery guide tip 99 and the opposed proximal end 97, and is configured so that at least a portion of the anchor delivery rod 94 along with the anchor assembly 40 or 41 extends therethrough. In another aspect, at least a portion of the anchor delivery guide 93 is flexible so that a tip 99 at the distal end of anchor delivery guide 93 is positioned at or adjacent to an intracardiac wall anchoring site 17.

The anchor delivery rod 94 is configured to securely attach anchor screw 21 to the anchoring site 17. The anchor delivery rod 94 has a distal end 101, an opposed proximal end 102 and an inner rod lumen 103 extending therebetween, the inner rod lumen 103 sized and configured so that at least a portion of the delivery cable 30 is inserted therethrough. In another aspect, at least a portion of the anchor delivery rod 94 is flexible so that a rod tip 104 at the distal end of the anchor delivery rod 94 is positioned at or adjacent to the intracardiac wall anchoring site 17.

As shown in FIG. 9B, a bore or socket 105 is defined in the anchor rod tip 104 of the anchor delivery rod 94. The socket is sized and configured to matingly engage the anchor cap 22 which includes a mating member such as an outer surface configuration which, as shown, is a hexagon. Other mating members or outer surface configurations may be employed. That is, at least a portion of the anchor cap is positioned in the socket 105 so that walls 107 of the socket engage the anchor cap. Thus, for example, when the anchor cap 22 is positioned in and engages the socket 105, rotation of the anchor delivery rod 94 rotates the anchor cap 22. Accordingly, the socket engages the anchor cap 22, and the anchor screw 21 extends distally from the anchor delivery rod 94 illustrated in 9B.

Now referring to FIGS. 10A-B, same anchor delivery system 92 is being used to deploy the anchor screw 61 of the halo anchor assembly 60, and it is contemplated that same anchor delivery system can be used to deploy the anchor screw 82 of the halo anchor assembly with flex connector 79, at the desired implantation site. As described above, at least a portion of the anchor delivery guide 93 is flexible so that a tip 99 at the distal end of anchor delivery guide 93 is positioned at or adjacent to an intracardiac wall anchoring site 17.

The anchor connector rod 71, coupled to the anchor connector 69, is configured to rotate anchor shaft 66 (not shown), which rotates the anchor screw base 62 and the attached anchor screw 61.

The anchor delivery system 92 further comprises a guide handle 108 with a deflection knob 109 coupled to the anchor delivery guide 93. The guide handle and the deflection knob are configured and used to help guide the tip 99 of the anchor delivery guide to the intracardiac wall anchoring site 17. As shown in FIG. 9A, the anchor delivery system 92 includes a rod handle 111 coupled to the anchor delivery rod 54. In FIG. 10A, rod handle 111 is coupled to anchor connector rod 71. In use, described more fully below, rotation of the rod handle 111 correspondingly rotates the rod tip 104, and the anchor cap 22 when the anchor cap 22 is received in the socket 105. In another aspect, rotation for the rod handle 111 correspondingly rotates the anchor connector rod 71 and affixed anchor connector 69, thereby rotating the anchor shaft base 62 and attached anchor screw 61.

The anchor delivery system 92 includes a trans-septal sheath 115 reversibly coupled to anchor delivery guide 93. The sheath 115 is in in fluid communication with anchor delivery guide 93 so that fluids, such as heparinized saline and the like, surround the anchor delivery guide through the sheath. A central sheath channel 116 is defined by the sheath 115 that is in communication with the anchor delivery guide 93 so that the anchor delivery rod 94 or anchor connector rod 71, and other system components, run through the central sheath channel 116. In another aspect, the trans-septal sheath 115 has a trans-septal sheath deflector knob 117 which deflects the sheath tip 118 when rotated.

The anchor delivery system 92 includes a J-wire 119 as shown in FIG. 11A that is guidable by the user to the anchoring site 17. The J-wire is, for example and without limitation, a 0.025" or 0.0035" J-wire. Of course, J-wires having other diameters are contemplated. As in any over-the-wire system, the J-wire is introduced first via sheath 115 into the left atrium 12 and, directed by any known intracardiac catheters, advanced to the left ventricle 16 to the anchoring site 17. By providing a pathway for anchor delivery guide 93 to track over to its final target, a J-wire increases the efficiency and safety of this step.

The Method of Implanting the Anchor Assembly

To install the anchor assembly 60 (anchor assembly 40, 41 not shown) to anchoring site 17, as shown in FIG. 11A, access is obtained to the femoral vein (not shown) using standard techniques, and a trans-septal crossing system (not shown) is used to traverse the interatrial septum into the left atrium 12. Over a wire in the left atrium 12, the trans-septal sheath 115 is advanced into the left atrium 12; the trans-septal sheath deflector knob 117 is rotated until the trans-septal sheath tip 118 is pointing to the mitral valve orifice 18. The J-wire 119, serving as a guidewire, is advanced to the anchor site 17, and the anchor delivery system 92 is guided by the user over the J-wire 119 to anchoring site 17.

As shown in FIG. 11A, the anchor delivery guide tip 99 is deflected by deflection knob 109 of guide handle 108 so that the distal end 96 of the anchor delivery guide 93 is positioned at or adjacent the anchoring site 17. The anchor connector rod 71 and anchor assembly 60 (anchor delivery rod 94 if anchor assembly 40 or 41 used) are initially positioned within the inner guide lumen 98 of the anchor delivery guide 93, but as shown in FIG. 11B when the anchor connector rod 71 has been advanced distally through the inner guide lumen 98, the docking ring 72, anchor screw base 62 and anchor screw 61 at or adjacent to the anchoring site 17.

With the anchor screw 61 of anchor assembly 60 positioned adjacent to the anchoring site 17, the rotating hand 111 of the anchor connector rod 71 is rotated to cause the corresponding rotation of the anchor screw base 62 as illustrated in FIG. 11B-C. For example, the rotating handle 111 is rotated in a first direction to cause corresponding rotation of the anchor screw base 62. The anchor screw 61 coupled the anchor screw base 62 also rotates and screws into the anchoring site 17, until the distal end portion 73 of the docking ring 72 is adjacent to the anchoring site 17. Note that in this position, the anchor screw 61 may or may not extend through this portion of the heart wall, but hemostatic membranes prevent bleeding from the anchoring site 17.

Figure 12B:
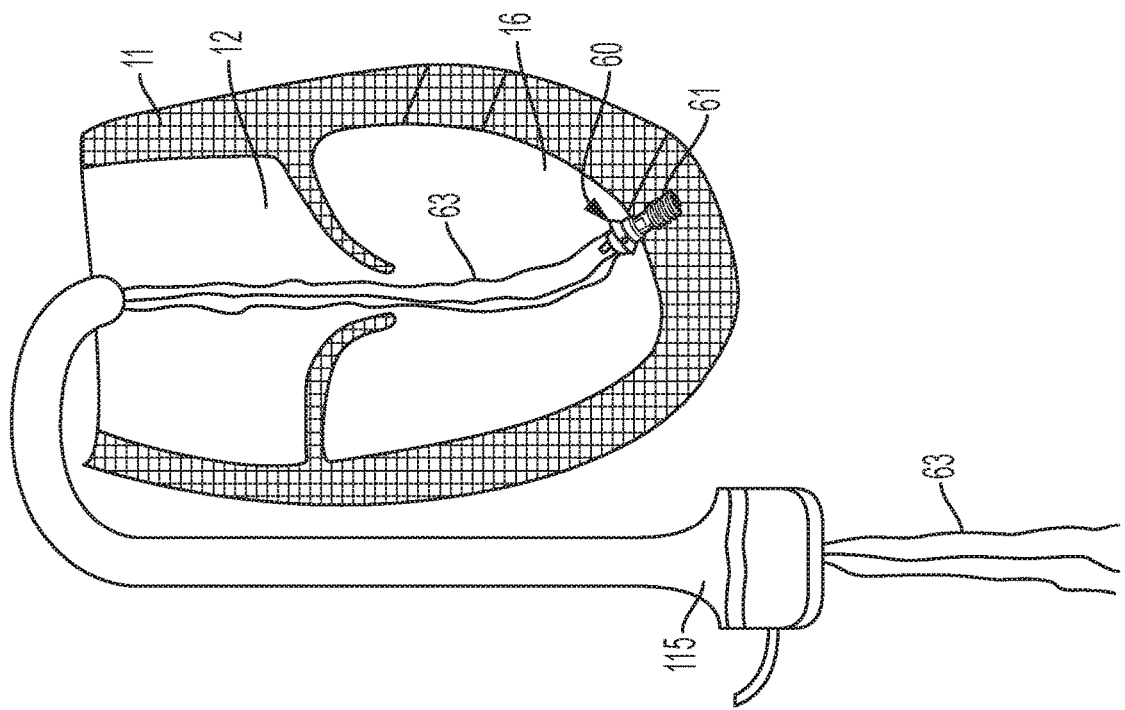
FIG. 12B is a perspective view of the anchor lines, connected to the anchor assembly of FIGS. 6A-F, positioned in the left ventricle.
Figure 12A:
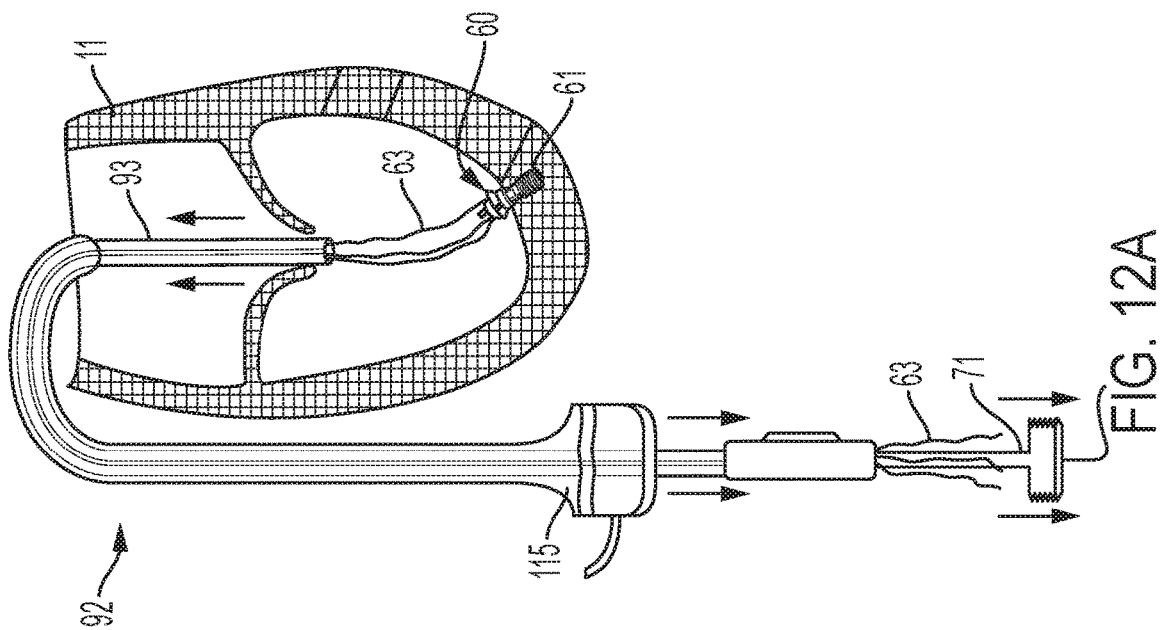
FIG. 12A is a perspective view of the anchor delivery system of FIG. 10A in which the anchor delivery system is exposing a portion of the anchor lines, connected via the anchor line swivel to the anchor assembly of FIGS. 6A-F, which is affixed to the left ventricle.

Upon placement of the anchor assembly 60 in the desired position, the anchor connector rod 71 and the anchor delivery guide 93 of the anchor delivery system 92 are retracted from the heart 11 as illustrated in FIG. 12A. As such, in FIG. 12B, the anchor lines 63 of anchor assembly 60, coupled to the anchor line rods 78 of docking ring 72 (which is coupled to anchor screw base 62), are secured by the anchor screw 61 within the left ventricle 16.

As shown in FIG. 12B, after placement of the anchor assembly 60, the at least one anchor line extends from the anchor assembly 60 through the mitral annulus 18 into the left atrium 12 into the trans-septal sheath 115 and externalized outside the body.

The Leaflet Grasper

Referring to FIGS. 13A-B, the system also comprises a leaflet grasper 130. The leaflet grasper 130 consists of a control handle 131, grasper shaft 135, and grasper arm 136. The leaflet grasper 10 may be formed of any flexible material such as, composed of one or more metal or metal alloys and/or one or more plastics.

In one aspect the grasper arm 136 consists of a grasping plate 138 and articulating arm 137, and can be in the closed configuration (FIG. 13A) or the open configuration (FIG. 13B). The grasper arm 136 is located at the distal end 133 of the grasper shaft 135, and the tip of the distal end 133 ends in nosecone 134.

In another aspect, the control handle 131, fused to the proximal end 132 of the grasper shaft 135 has a trajectory knob 141, which controls the medial/lateral trajectory of the distal end 133 of grasper shaft 135, grasper control 142, which opens and closes the grasper arm 136, puncturing rod handle 143, which drives the puncturing rod 147 and attached chord 160 through the grasped leaflet, retraction handle 146 which pulls the retraction rod and captured chord 160 out of the control handle 131 of the leaflet grasper 130, and a chord release handle 144, which advances the chord release tube 156 out of the nosecone 134, allowing the chord to move out of the split seam of the grasper arm, thereby freeing the chord from the grasper arm.

Now referring to FIGS. 14A-D, the grasper shaft 135 contains puncturing rod 147, which houses the chord 160, which is fused to puncturing element 148, which rests outside, but is not connected to, puncturing rod 147. After puncturing rod 147 has pushed puncturing element 148 and attached chord 160 through the leaflet (after leaflet has been captured by grasping plate 138 of grasping arm 136), puncturing element 148 enters the lumen 151 of receiving cap 149, which captures puncturing element 148. Pulling retraction handle 146 (FIGS. 13A-B) pulls on retracting rod 153 thereby retracting receiving cap 149, which is attached to distal end 154 of retracting rod 153. Therefore, receiving cap 149, attached to chord 160 via puncturing element 148, can be withdrawn through distal end 157 of chord release tube 156, until it exits the grasper shaft 135 via the proximal end of the control handle 131 (FIGS. 13A-B).

The Chords

Figure 15B:
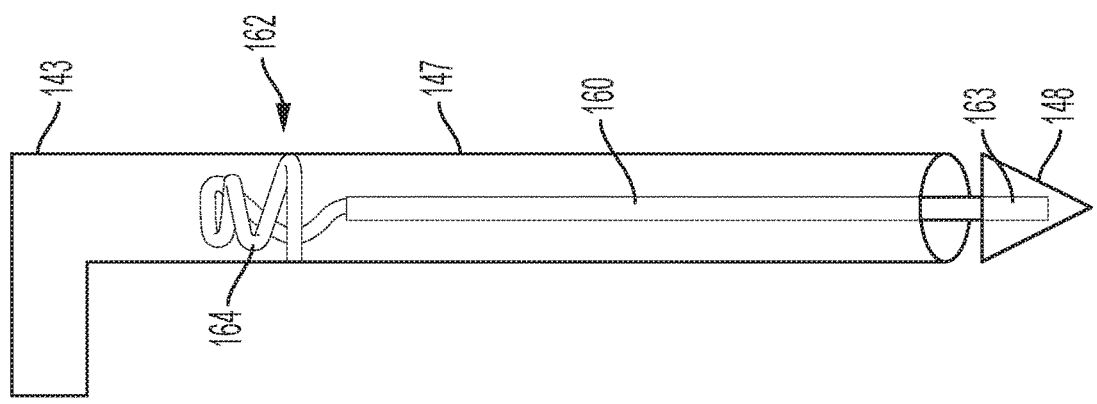
FIG. 15B is a magnified side elevational view of the puncturing rod and puncturing element housing a chord attached to a knot.
Figure 15A:
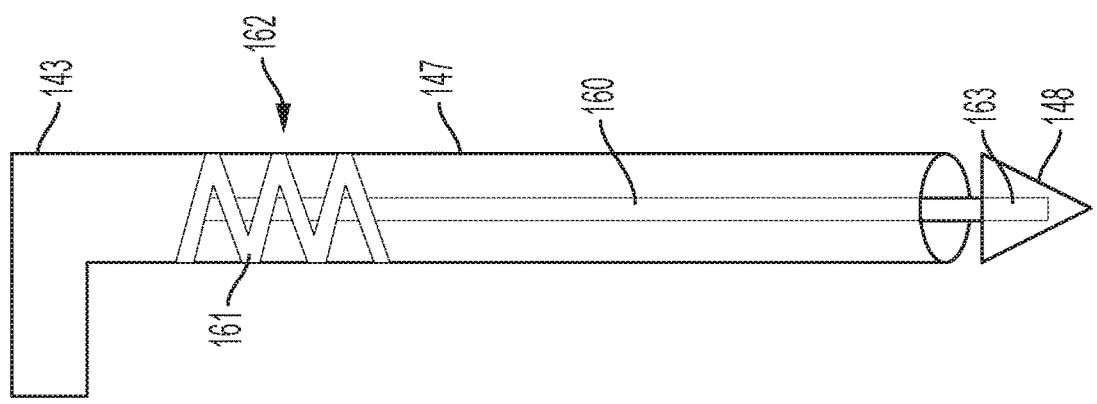
FIG. 15A is a magnified side elevational view of the puncturing rod and puncturing element housing a chord attached to a pledget.

Referring to FIGS. 15A-B, each chord 160 is housed inside the puncturing rod 147 before deployment. The proximal chord 162 rests in the proximal portion of the puncturing rod 147 close to the puncturing rod handle 143 and is attached to either a pledget 161 or a bulky knot 164. The knot 164 may consist of one or more knots of any configuration and be composed of, but not limited to, expanded polytetrafluoroethylene (ePTFE), polyethylene terephthalate (PET), ultra-high-molecular-weight polyethylene, nylon, or nitinol wire. The pledget 161 may be of any dimension or polygonal shape and may be composed of any combination of PTFE, ePTFE, PET, or biological membranes such as, but not limited to, bovine or porcine pericardial tissue. The body of the chord 160 may be composed of any combination of PTFE, ePTFE, PET, nylon, ultra-high-molecular-weight polyethylene or nitinol wire. The end of the chord is fused to a puncturing element 148 that may be composed of any metallic alloy.

The Method of Grasping the Leaflet and Chord Implantation

Advancing the Leaflet Grasper to the Leaflet

Figure 16B:
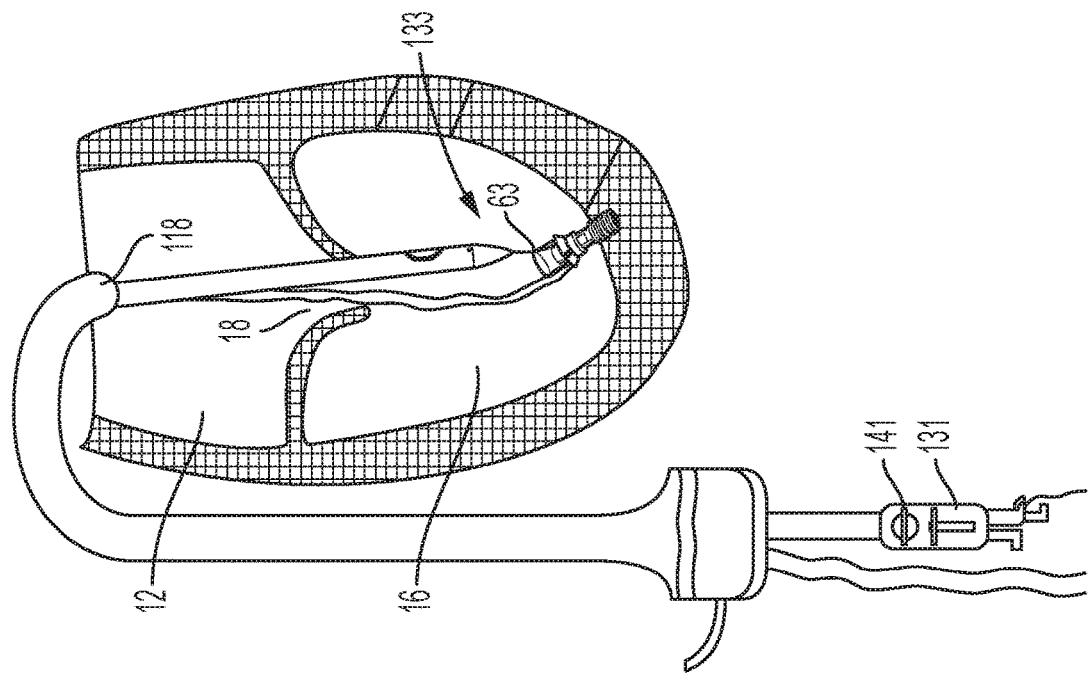
FIG. 16B is a perspective view of the leaflet grasper of FIG. 13A advancing over anchor line across the mitral valve.
Figure 16A:
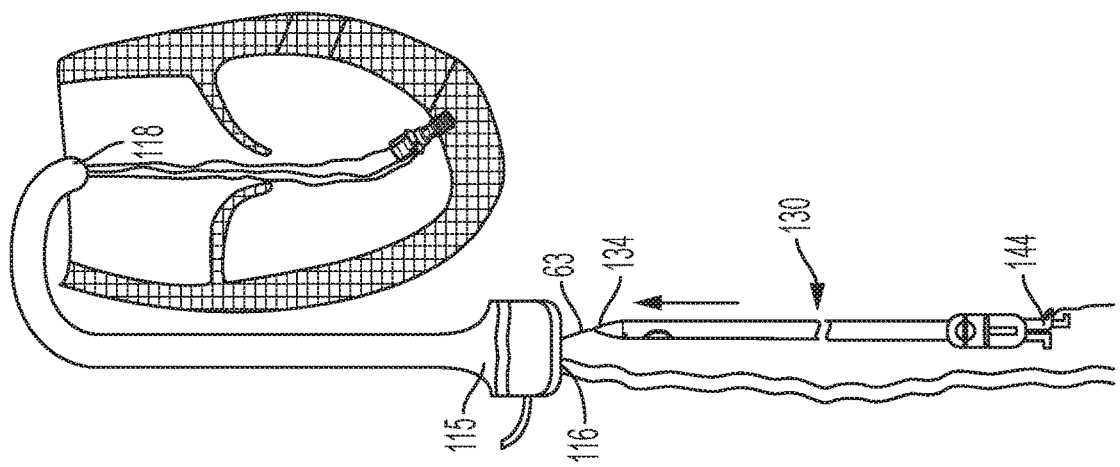
FIG. 16A is a perspective view of the leaflet grasper of FIG. 13A advancing over an anchor line into the transeptal sheath.
Figure 17B:
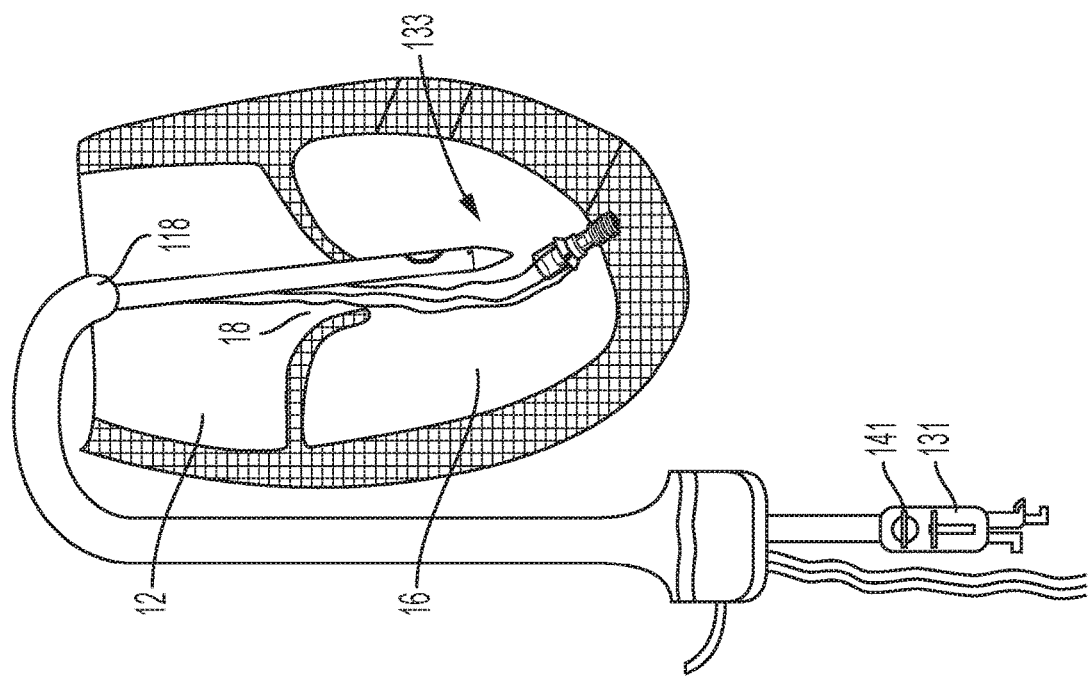
FIG. 17B is a perspective view of the leaflet grasper of FIG. 13A advancing separately from the anchor lines across the mitral valve.
Figure 17A:
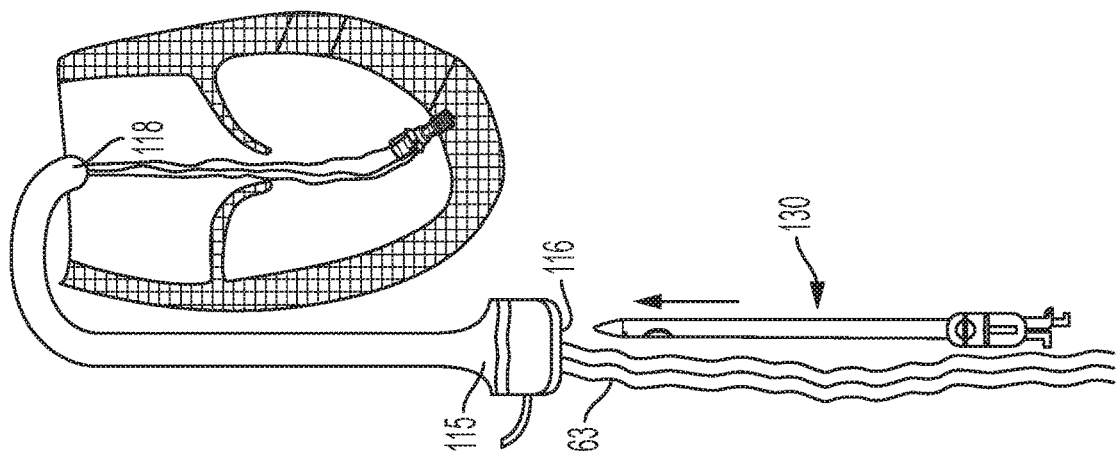
FIG. 17A is a perspective view of the leaflet grasper of FIG. 13A advancing separately from the anchor lines into the transeptal sheath.

Referring to FIG. 16A, anchor line 63 is advanced through nosecone 134 of leaflet grasper 130, through chord release tube 156, until anchor line 63 exits leaflet grasper through the end of chord release handle 144. Then leaflet grasper 130 is introduced into lumen 116 of trans-septal sheath 115 and advanced until it exits end 118 of trans-septal sheath 115. The length of leaflet grasper 130 is shown as abbreviated in FIG. 16A by use of sinusoidal lines. Now referring to FIG. 16B, after exiting end 118 of trans-septal sheath 115, trajectory knob 141, located on the control handle 131, is rotated until the end 133 of leaflet grasper 130 flexes in the left atrium 12 so that the end 133 can be perpendicular to the mitral valve orifice 18, and then be able to advance into the left ventricle 16. Referring to FIG. 17A, the leaflet grasper 130 can be advanced through lumen 116 of trans-septal sheath 115 and exit end 118 of trans-septal sheath 115 without having to advance over anchor line 63.

Referring to 17B, after exiting end 118 of trans-septal sheath 115, trajectory knob 141, located on the control handle 131, is rotated until the end 133 of leaflet grasper 130 flexes in the left atrium 12 so that the end 133 can be perpendicular to the mitral valve orifice 18, and then be able to advance into the left ventricle 16.

Grasping the Leaflet

Figure 18C:
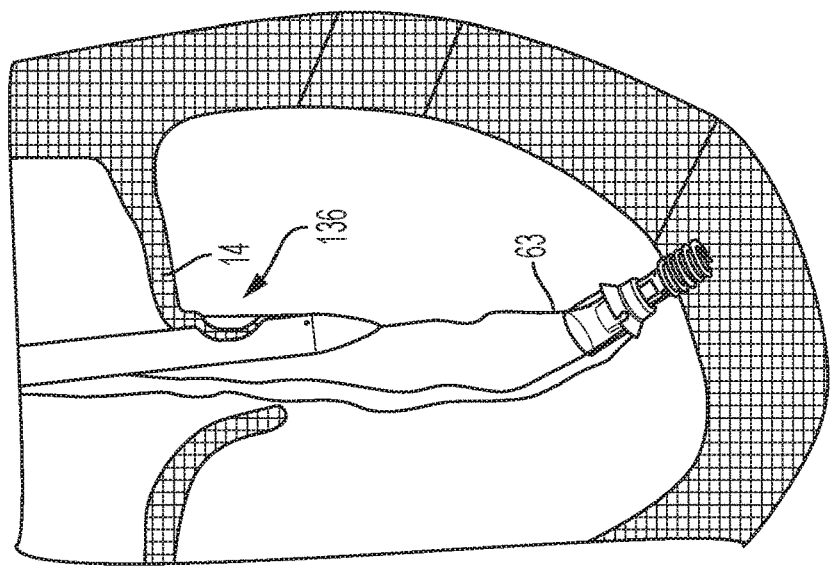
FIG. 18C is a magnified perspective view of the leaflet grasper going over an anchor line, with the leaflet grasper arm fully closed on the grasped leaflet.
Figure 18B:
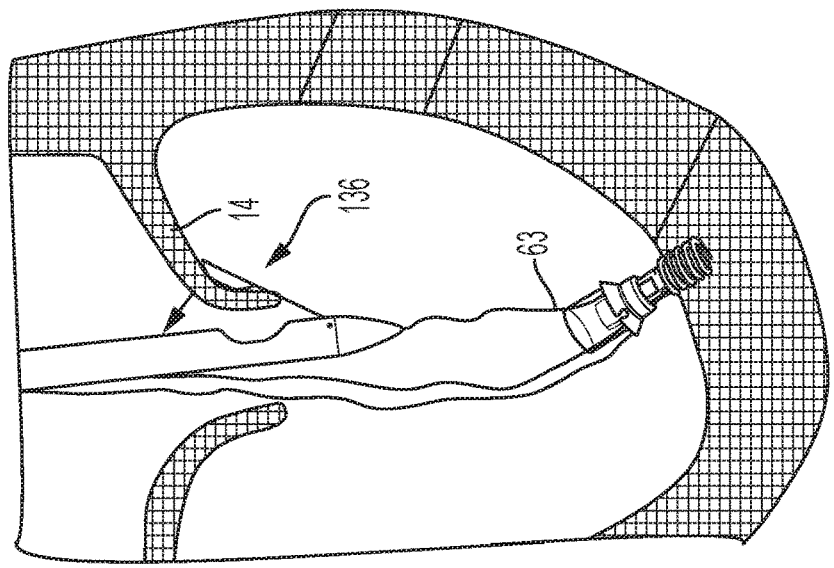
FIG. 18B is a magnified perspective view of the leaflet grasper going over an anchor line, with the leaflet grasper arm closing on a leaflet.
Figure 18A:
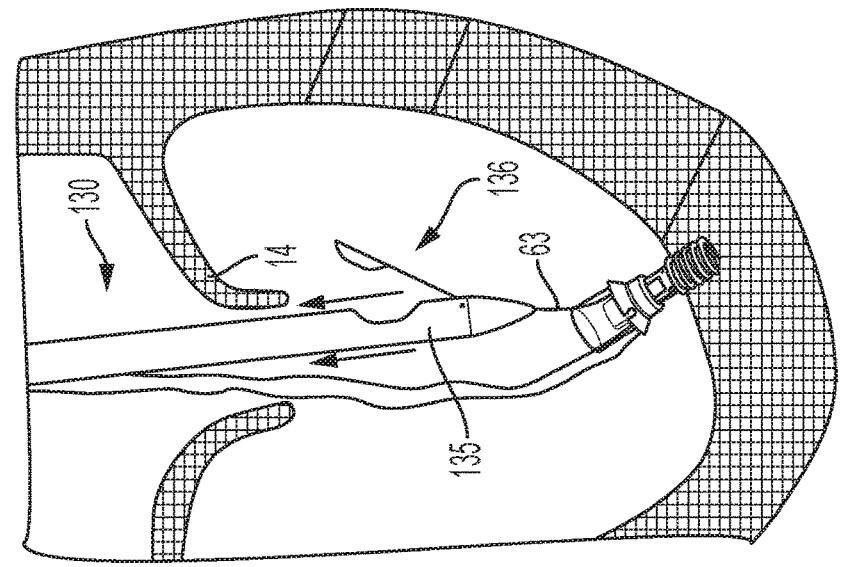
FIG. 18A is a magnified perspective view of the leaflet grasper going over an anchor line, with the leaflet grasper arm open and being retracted to grab the leaflet.
Figure 19C:
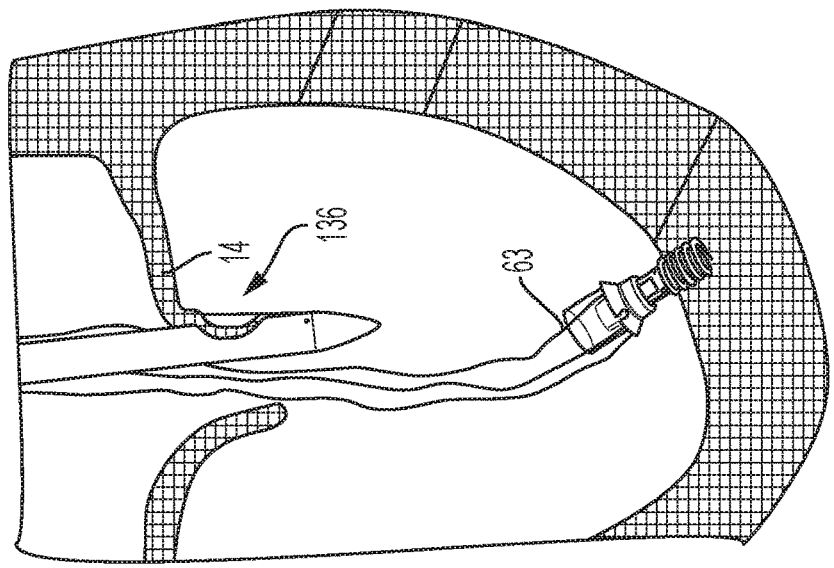
FIG. 19C is a magnified perspective view of the leaflet grasper advancing freely (not over an anchor line), with the leaflet grasper arm fully closed on the grasped leaflet.
Figure 19B:
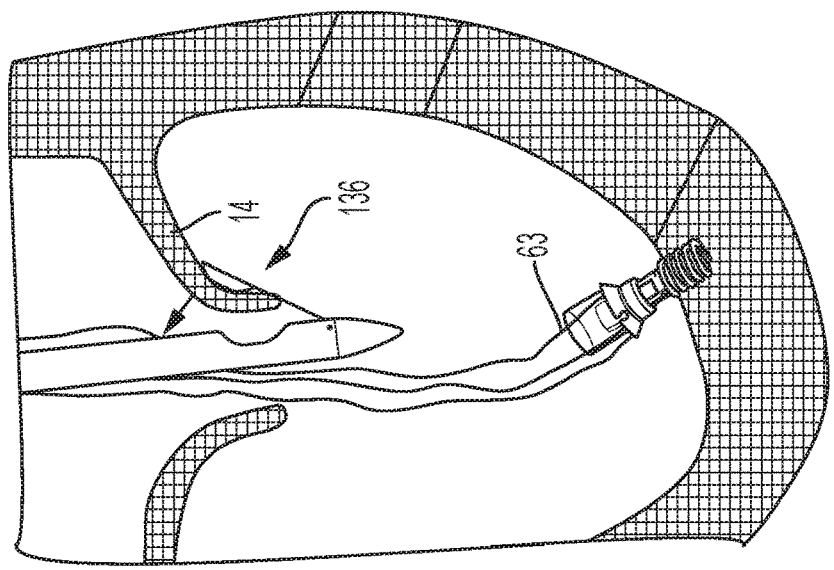
FIG. 19B is a magnified perspective view of the leaflet grasper advancing freely (not over an anchor line), with the leaflet grasper arm closing on a leaflet.
Figure 19A:
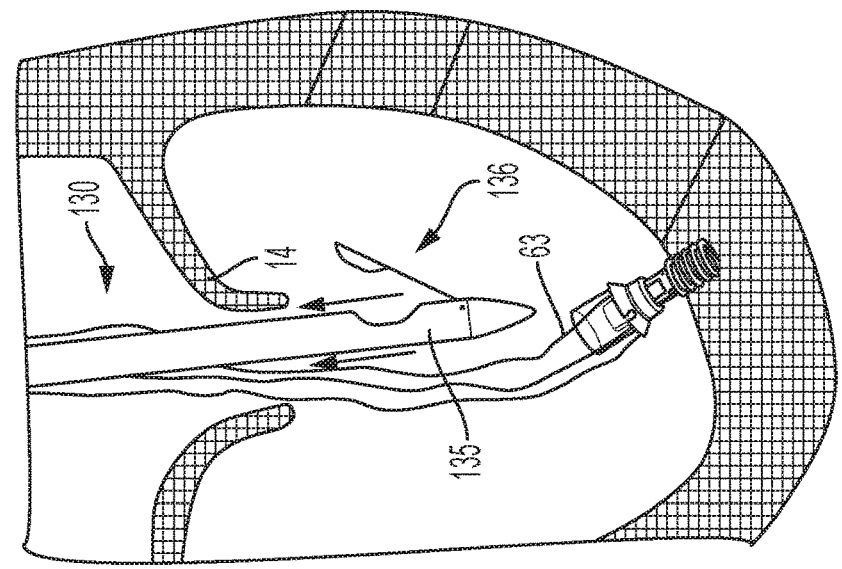
FIG. 19A is a magnified perspective view of the leaflet grasper advancing freely (not over an anchor line), with the leaflet grasper arm open and being retracted to grab the leaflet.

Now referring to FIGS. 18A-C, first the grasper arm 136 is opened by the grasper control 142 (FIG. 13B). Next the grasper shaft 135 of the leaflet grasper 130 is retracted until either the mitral leaflet (in FIGS. 18A-C, it is posterior mitral leaflet 14) is captured by the grasper arm 136. Once the leaflet is securely in the grasper arm 136, the grasper control 142 is used to close the grasper arm 136 so that the leaflet is trapped between the grasper arm 136 and the grasper shaft 135. In the FIGS. 19A-C, the process for grasping the leaflets is the same except the leaflet grasper, as in FIGS. 17A-B, does not have anchor line running through it.

Chord Implantation

For FIGS. 20-27, the leaflet grasper 135 is shown with anchor line 63 entering nosecone 134 and running through chord release tube 156, but the same sequence of events can occur with the leaflet grasper 135 not having anchor line 63 run through it.

Figure 20B:
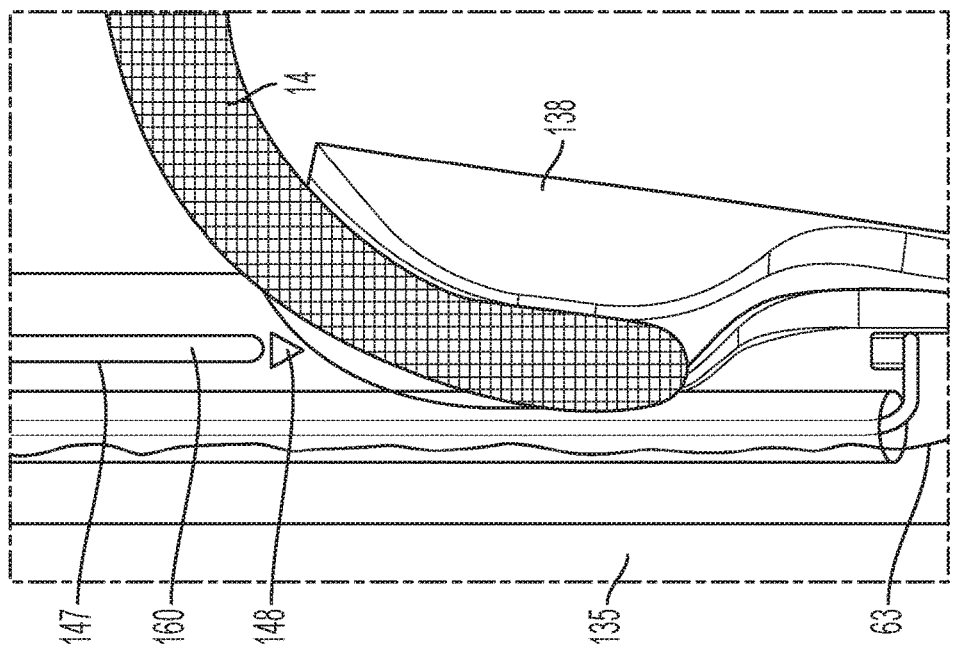
FIG. 20B is a highly magnified side elevational view of the leaflet grasper with its grasper arm fully closed on the grasped leaflet.
Figure 20A:
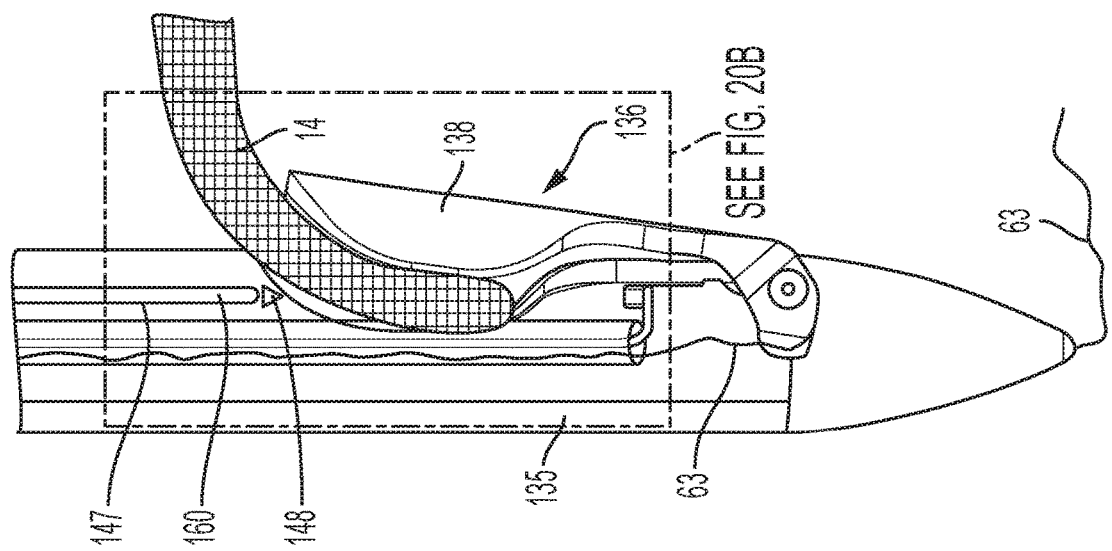
FIG. 20A is a magnified side elevational view of the leaflet grasper with its grasper arm fully closed on the grasped leaflet.
Figure 21C:
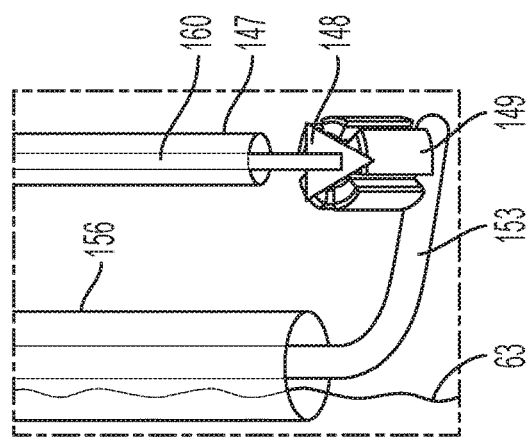
FIG. 21C is a highly magnified side elevational view of the puncturing rod and element coupling with the receiving cap and attached retracting rod.
Figure 21B:
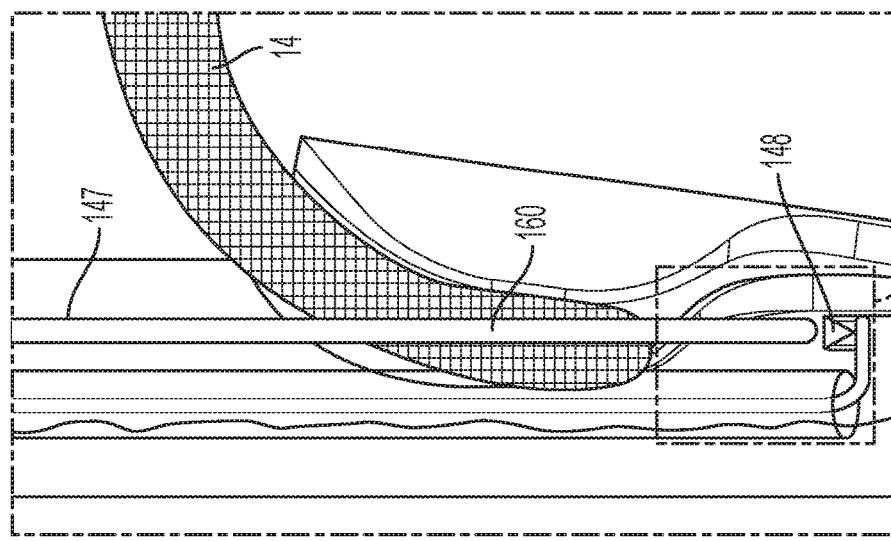
FIG. 21B is a highly magnified side elevational view of the leaflet grasper after leaflet has ben grasped and punctured by puncturing rod and element.
Figure 21A:
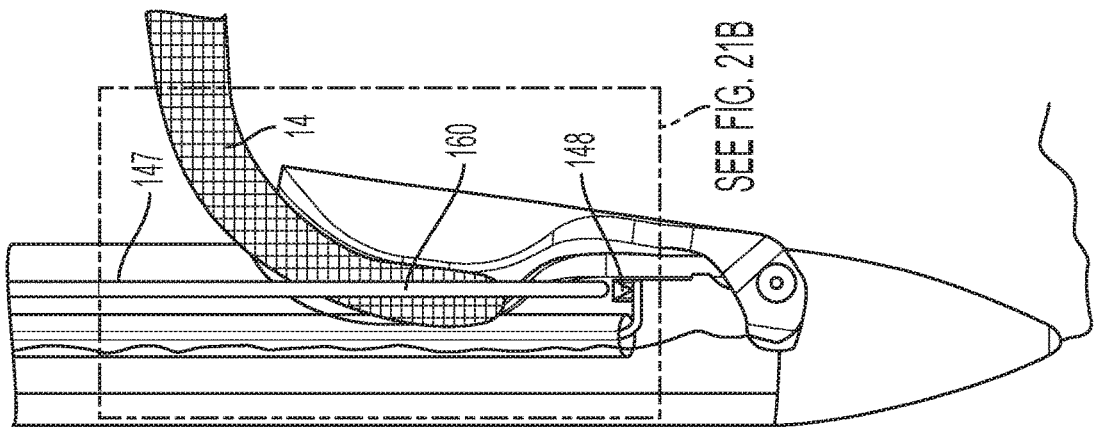
FIG. 21A is a magnified side elevational view of the leaflet grasper after leaflet has been grasped and punctured by puncturing rod and element
Figure 22B:
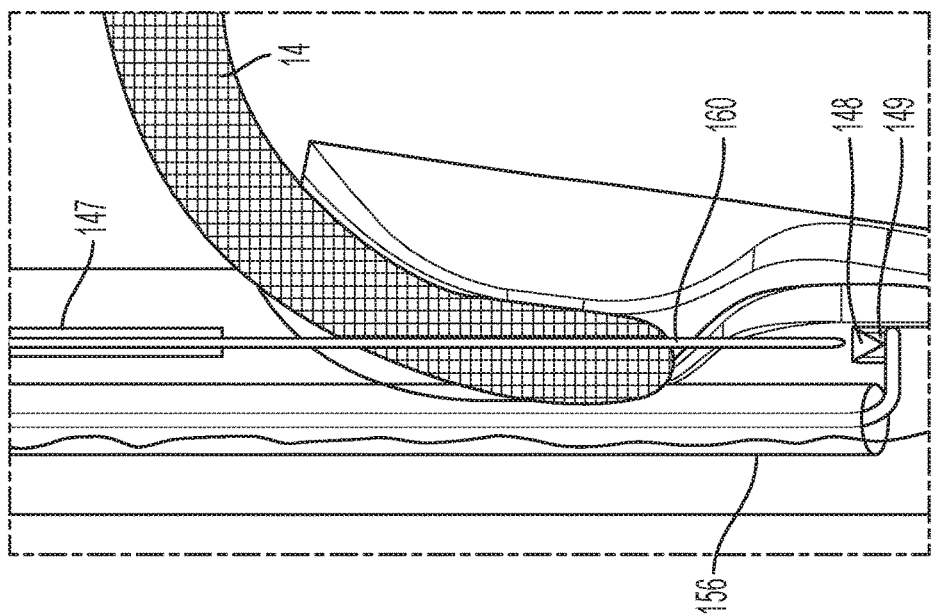
FIG. 22B is a highly magnified side elevational view of the leaflet grasper after chord has passed through leaflet and with the puncturing rod retracted above the leaflet.
Figure 22A:
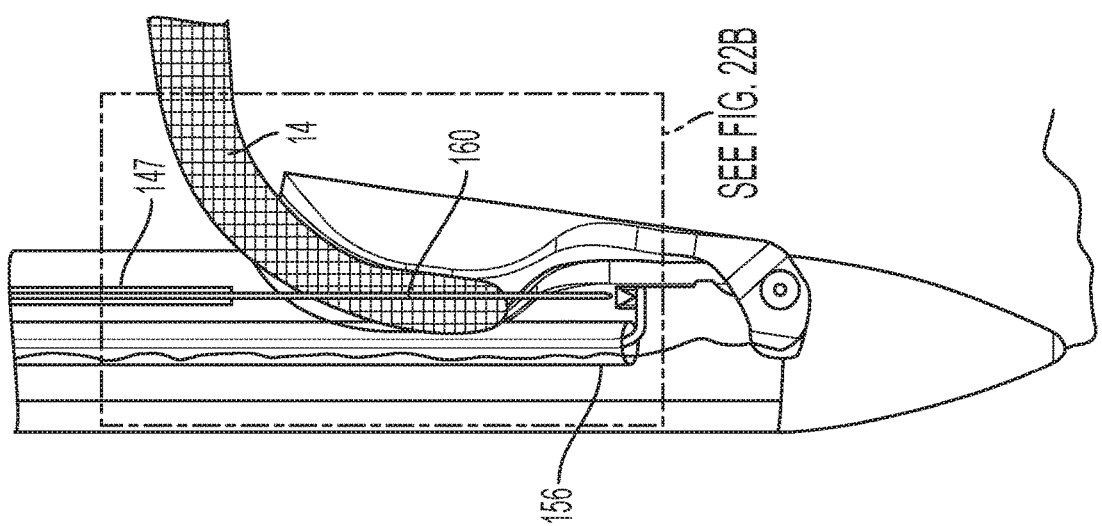
FIG. 22A is a magnified side elevational view of the leaflet grasper after chord has passed through leaflet and with the puncturing rod retracted above the leaflet.
Figure 23:
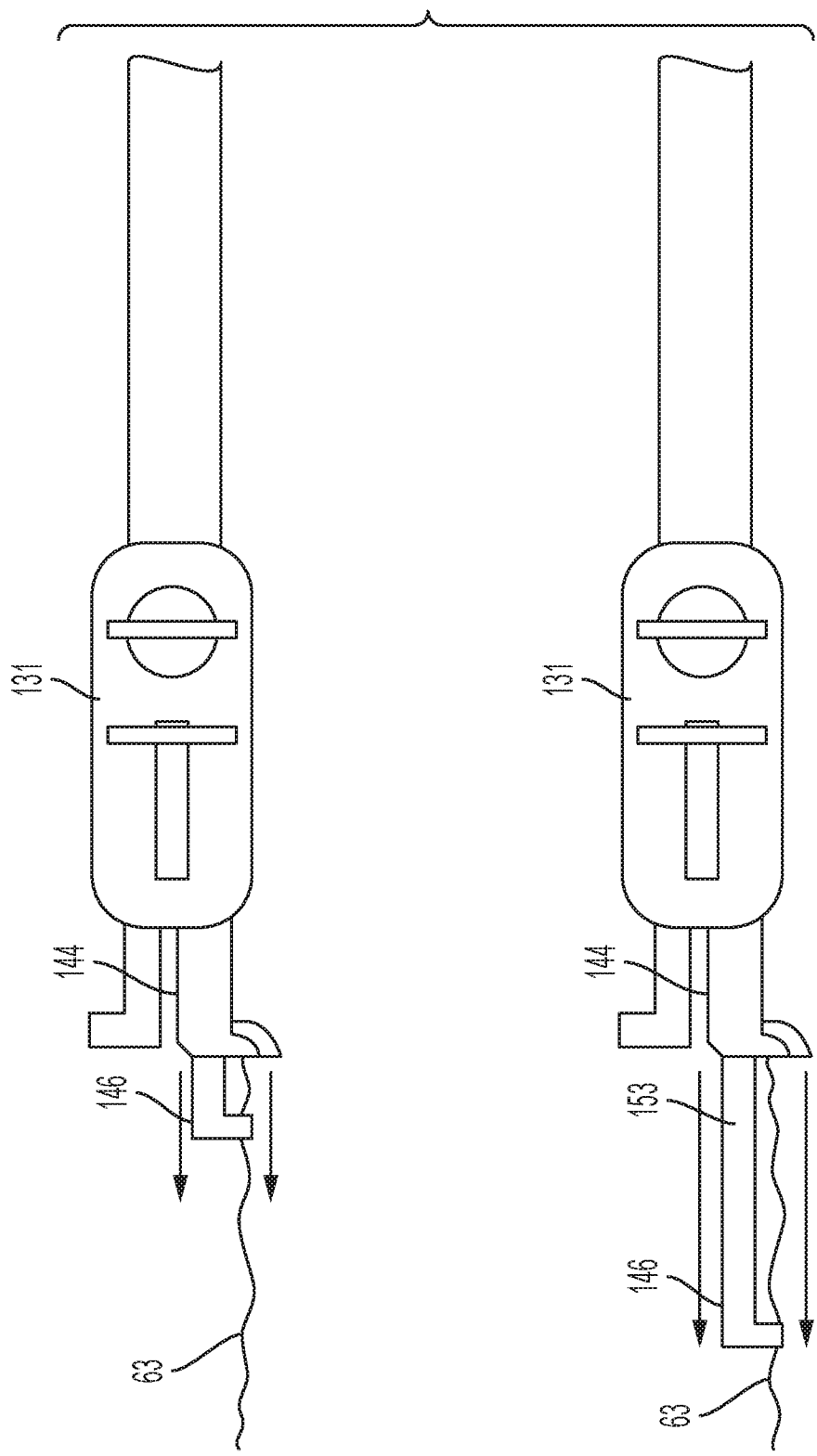
FIG. 23 is a side elevational view of the handle of the leaflet grasper.
Figure 24B:
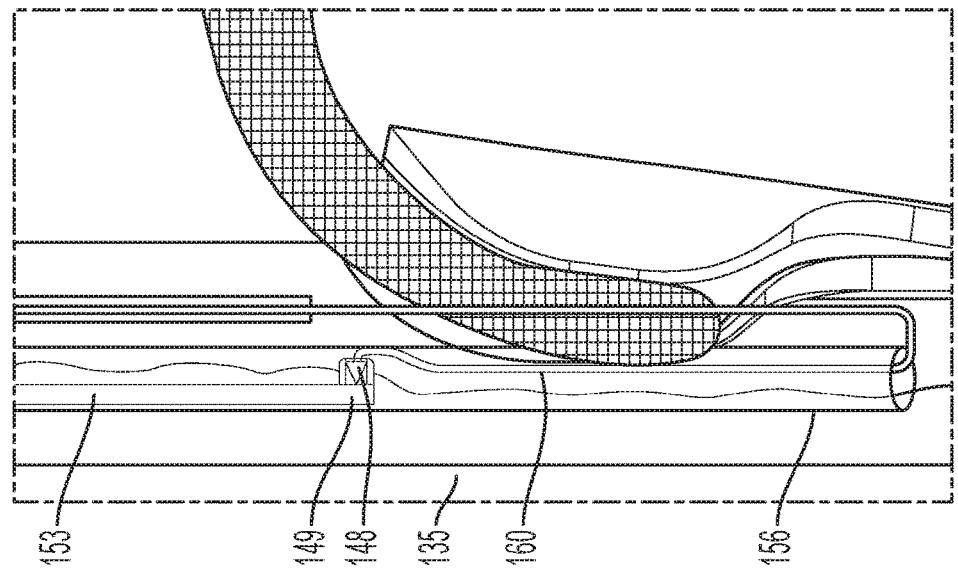
FIG. 24B is a highly magnified side elevational view of the leaflet grasper after the puncturing element has been attached to the receiving cap, and the retracting rod has pulled the captured element and chord up the shaft.
Figure 24A:
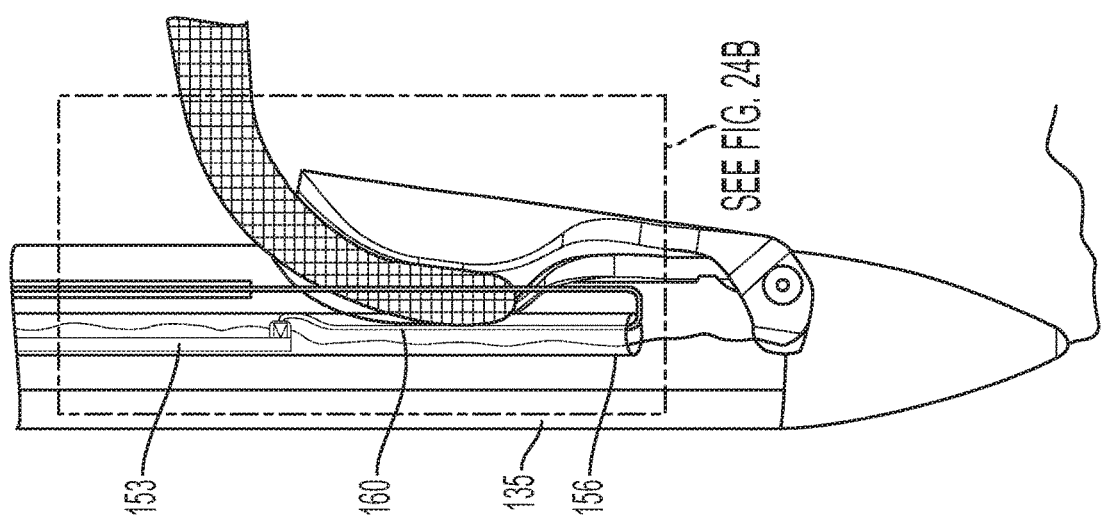
FIG. 24A is a magnified side elevational view of the leaflet grasper after the puncturing element has been attached to the receiving cap, and the retracting rod has pulled the captured element and chord up the shaft.
Figure 25:
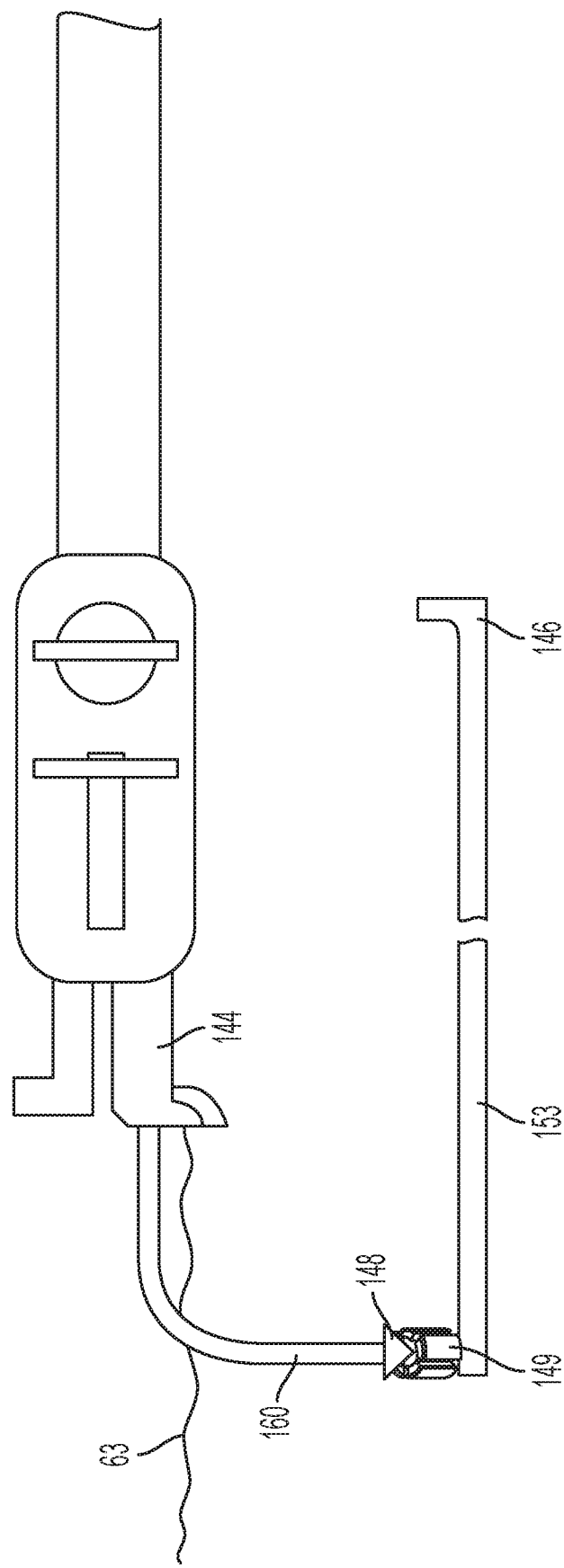
FIG. 25 is a side elevational view of the captured chord being pulled out of the handle of the leaflet grasper.
Figure 26B:
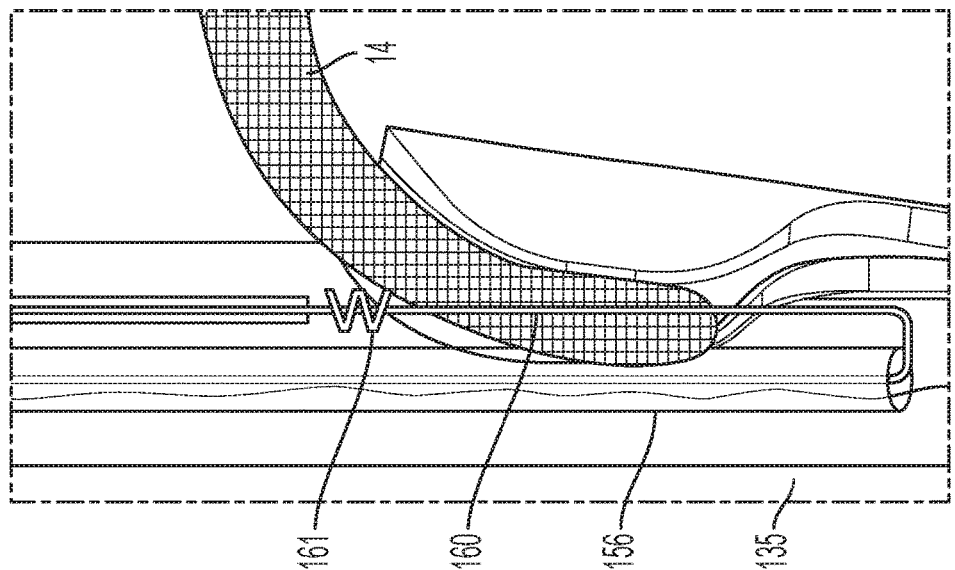
FIG. 26B is a highly magnified side elevational view with the end of the chord (pledget pictured) pulled against the atrial side of the leaflet;'
Figure 26A:
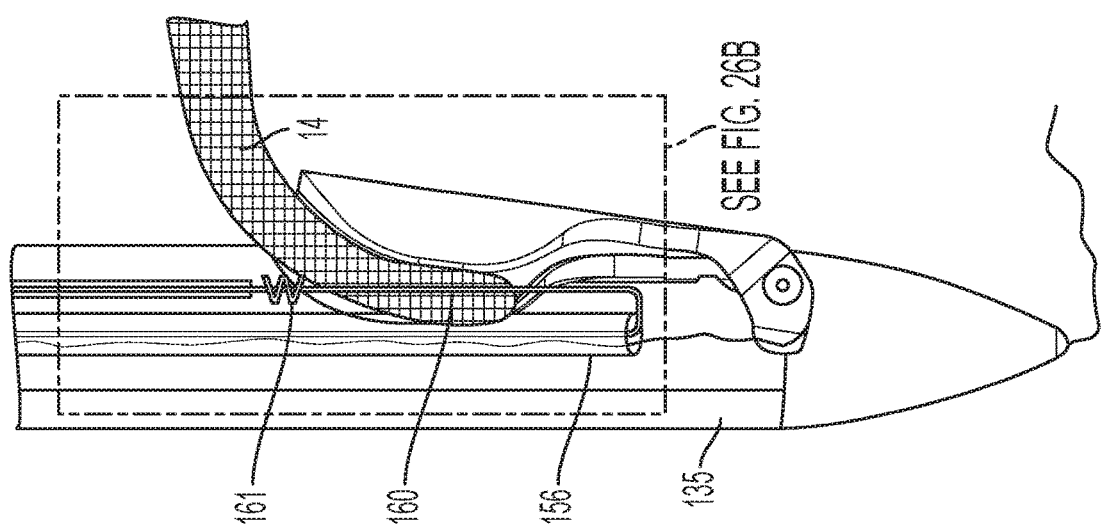
FIG. 26A is a magnified side elevational view with the end of the chord (pledget pictured) pulled against the atrial side of the leaflet.

Now referring to FIGS. 20A-B, the leaflet (for purposes of illustration leaflet 14, although leaflet 13 can be similarly grasped) has been grasped by the grasper plate 138 of the grasper arm 136. Within the grasper shaft 135, the puncturing rod 147, containing chord 160, rests above puncturing element 148, which is connected to chord 160. Referring to FIGS. 21A-C, puncturing rod 147, containing chord 160, is pushed down by puncturing rod handle 143 (FIGS. 13A-B), thereby driving puncturing element 148 through the leaflet 14. Puncturing element 148 continues moving down until it enters receiving cap 149, which couples to puncturing element 148 and associated chord 160. Next, referring to FIGS. 22A-B, the puncturing rod 147 is retracted back up and above the leaflet 14 by retracting the puncturing rod handle 143, leaving behind leaflet chord 160, which remains through the leaflet 14, and is attached to puncturing element 148, which is coupled to receiving cap 149. Referring to FIG. 23, pulling retraction handle 146 pulls retracting rod 153 out of chord release handle 144 of control handle 131. As shown in FIGS. 24A-B, this motion is transmitted distally so that as retracting rod 153 moves up in grasper shaft 135, receiving cap 149 (attached to distal end of retracting rod 153) is pulled through the chord release tube 156, along with the puncturing element 148 (coupled to receiving cap 149) and attached chord 160. As shown in FIG. 25, the operator keeps pulling back the retraction handle 146 (connected to retracting rod 153), until the receiving cap 149 and coupled puncturing element 148 are pulled out of the chord release handle 144, thereby externalizing chord 160. Internally, as shown in FIGS. 26A-B, within grasper shaft 135, the pledget 161 (or knot 164), stops on the atrial surface of leaflet 14, with the rest of the chord 160 going through the leaflets 14, back out the chord release tube 156.

Figure 27C:
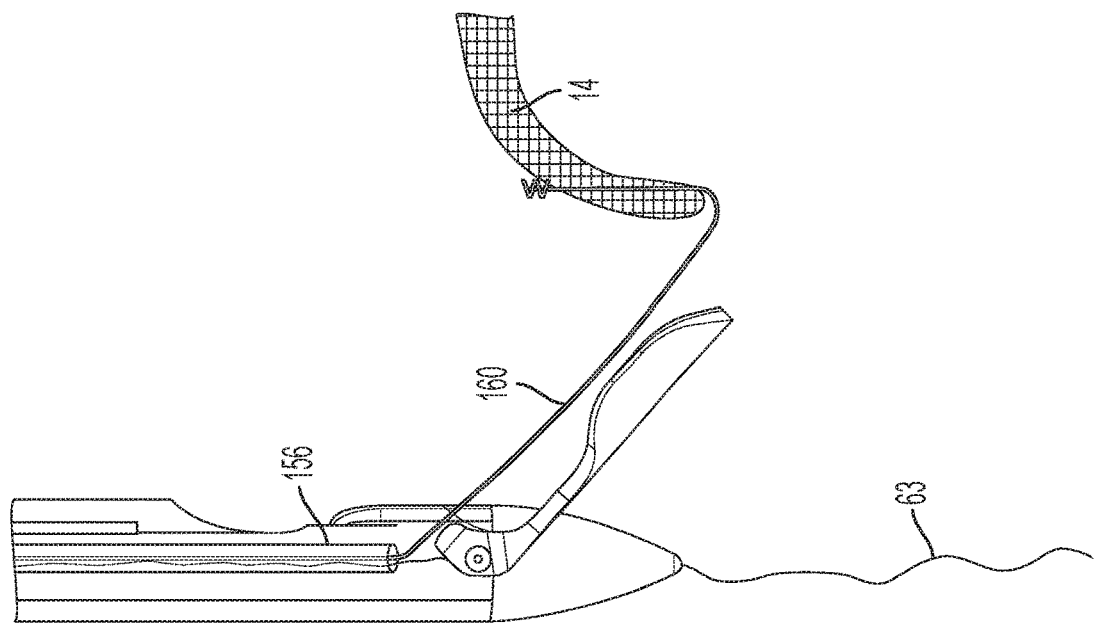
FIG. 27C is a side elevational view of the leaflet grasper free from the leaflet and being retracted up and away from the leaflet.
Figure 27B:
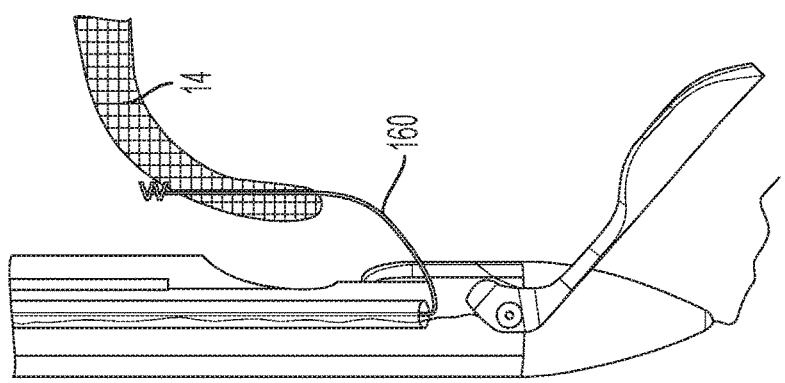
FIG. 27B is a side elevational view of the leaflet grasper free from the leaflet.
Figure 27A:
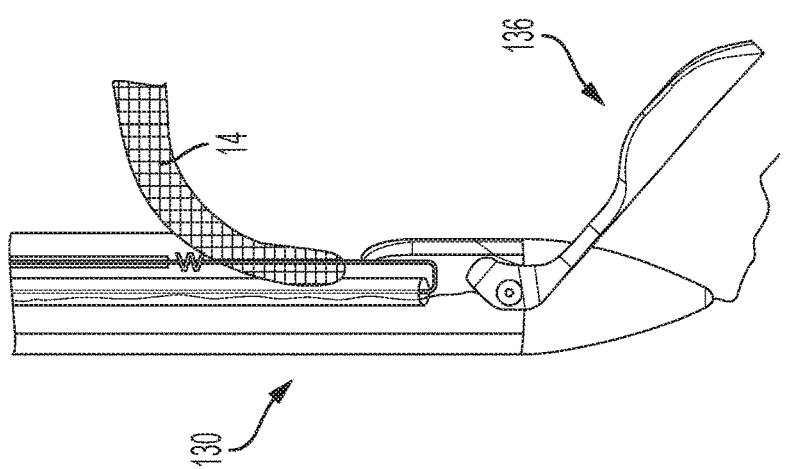
FIG. 27A is a side elevational view of the leaflet grasper arm releasing the leaflet after chord delivery.
Figure 28B:
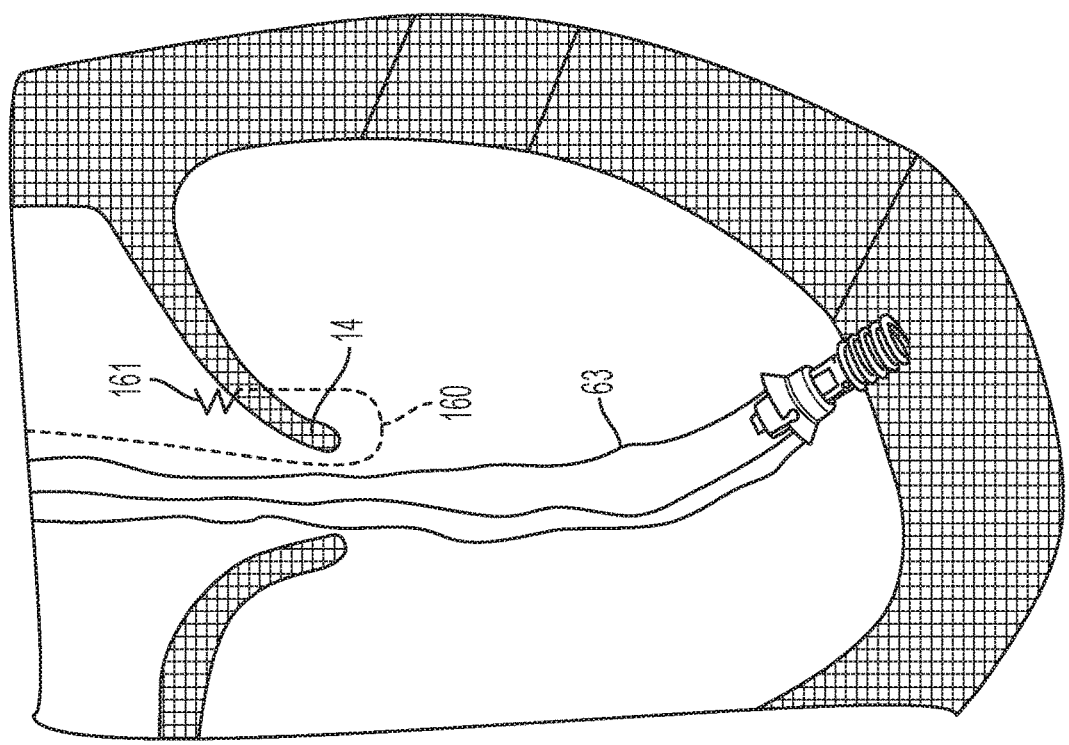
FIG. 28B is a magnified cross-sectional perspective view with the anchor and anchor lines in place, along with one chord delivered through one leaflet.
Figure 28A:
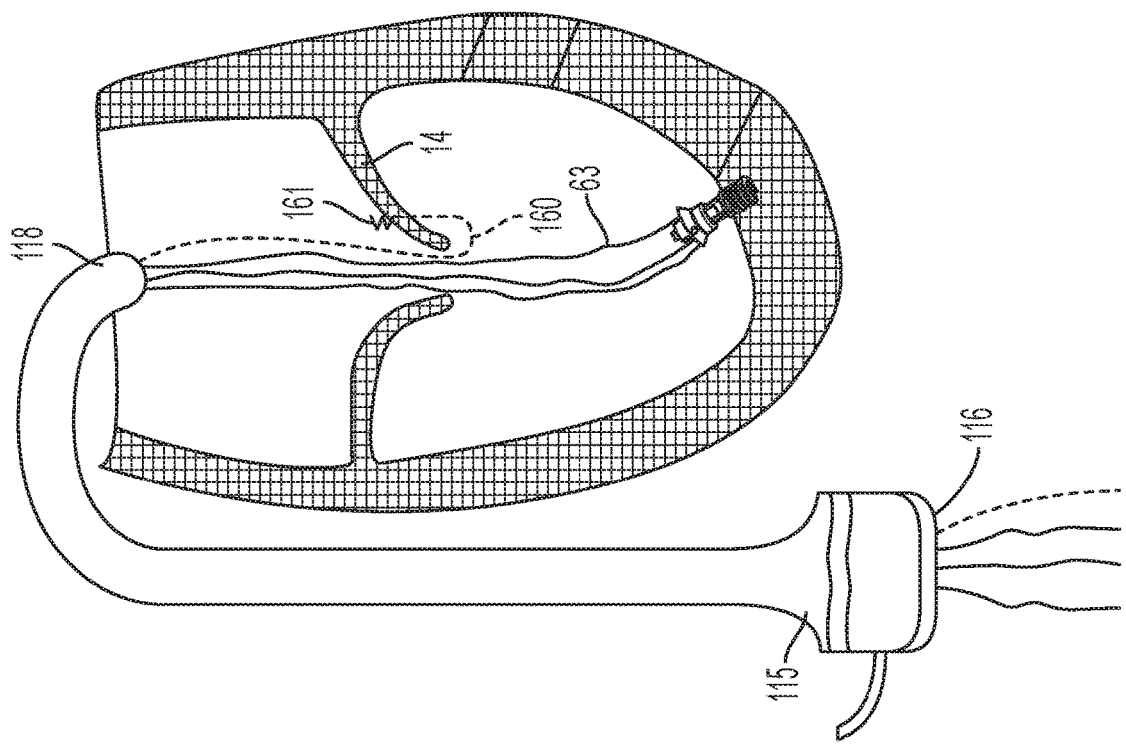
FIG. 28A is a cross-sectional perspective view with the anchor and anchor lines in place, along with one chord delivered through one leaflet.

Referring to FIGS. 27A-C, to free the leaflet grasper 130 from leaflet 14, the grasper arm 136 is inverted by action of the grasper control 142. Then, the leaflet grasper 130 can but pushed away from the leaflet 14, and as the leaflet grasper 130 is removed out of the body, the chord 160 and anchor line 63 freely translate through chord release tube 156. In the situation that the leaflet grasper 130 does not run over an anchor line 63, only the chord 160 translates through chord release tube 156. After the leaflet grasper 135 has been removed, FIGS. 28A-B show the implanted chord 160, secured to leaflet by pledget 161, running along side anchor line 63, entering distal end 118 of trans-septal guide 115, and exiting lumen 116 to outside body.

Tensioning and Locking Chords
Reversible Locks (Collet Mechanism)

Figure 29B:
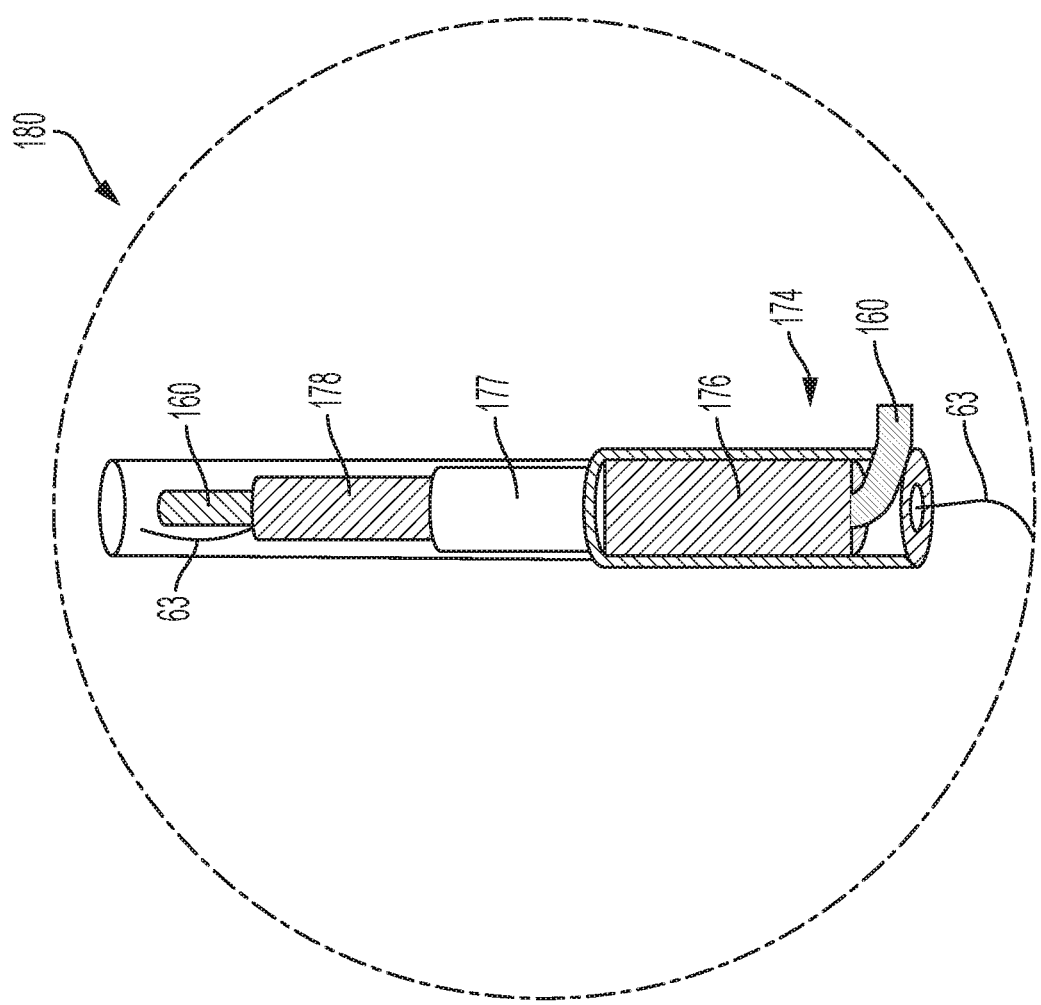
FIG. 29B is a magnified side elevational view of the collet locking system.
Figure 29A:
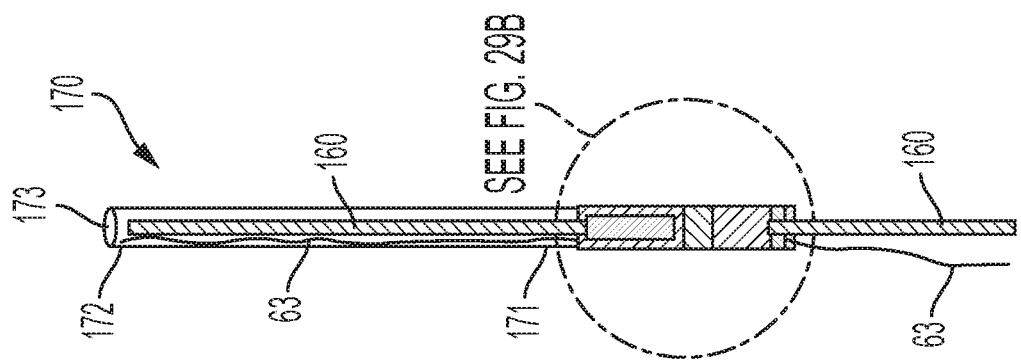
FIG. 29A is a side elevational view of the collet locking system

With reference to FIGS. 29A-B, the at least one lock positioning rod 170 has a distal end 171, a proximal end 172 and an inner rod lumen 173 sized and configured so that a portion of a chord 160 and anchor line 63 are inserted therethrough. At least a portion of the lock positioning rod 170 is flexible so that the distal end 171 may be positioned at or adjacent anchor rod line 54 or 78. The at least one lock positioning rod 170 is coupled to conduit 174. As illustrated in FIGS. 29A-B and FIGS. 30-31, each conduit 174 contains a detachable lock 176, which is configured to securely attach at least one chord 160 and anchor line 63.

Figure 30:
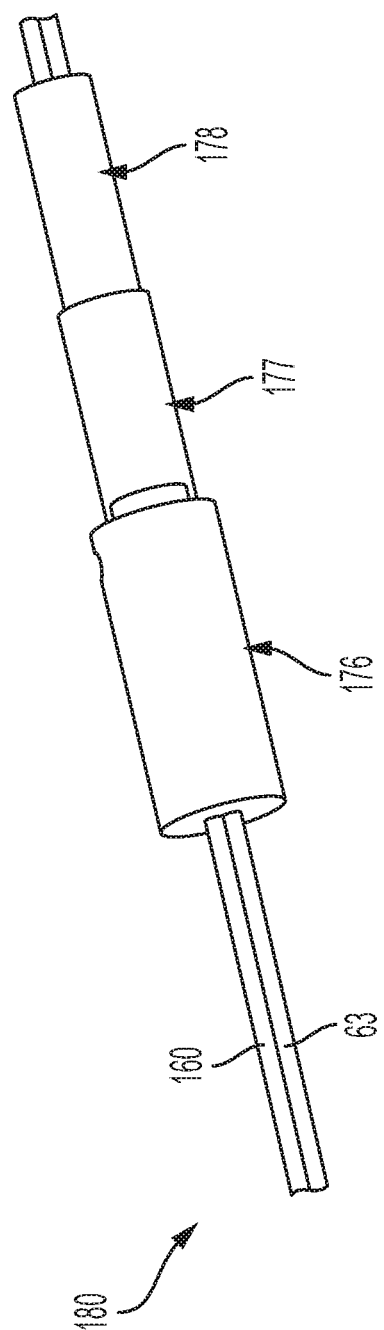
FIG. 30 is a perspective view of the collet locking system.
Figure 31A:
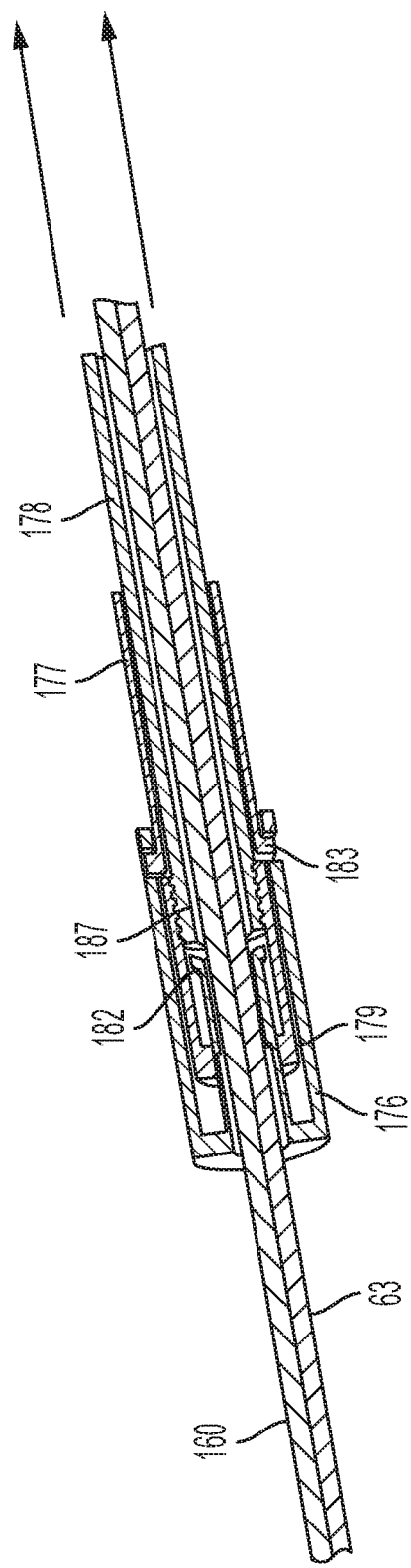
FIG. 31A is a cross-sectional perspective view of the collet locking system in the unlocked position.
Figure 31B:
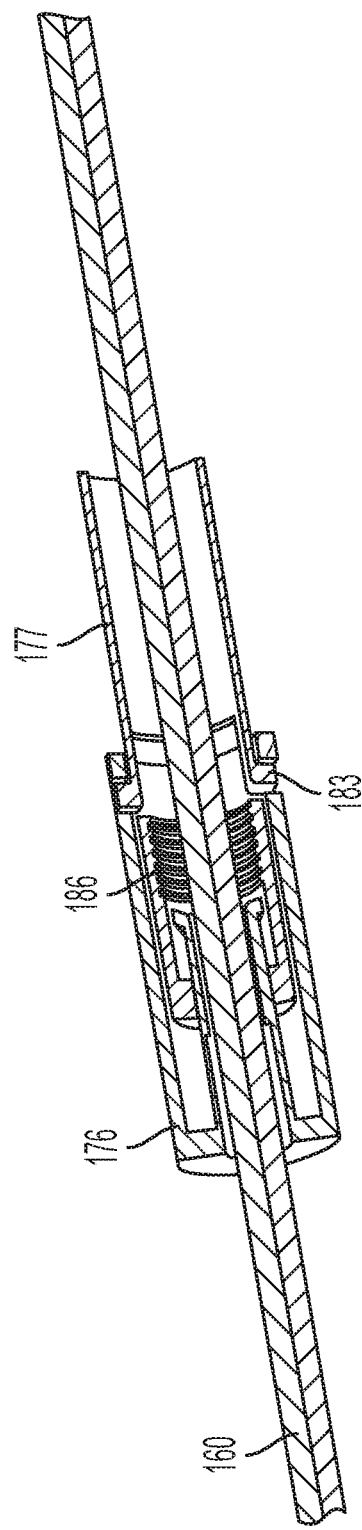
FIG. 31B is a cross-sectional perspective view of the collet locking system in the locked position.

Referring to FIGS. 30, 31A-B, an inner surface of lock 176 defines a first mating surface 186 which is shown as a threaded area. A distal end of the second hypotube 178 defines a second mating surface 187 configured to cooperate with the first mating surface 186. Accordingly, the second retracting hypotube 178 may be rotated so as to disengage the cooperating threaded areas 186 and 187. The second hypotube 178 is then retracted. This is illustrated in FIG. 31B. As the second hypotube (i.e. is withdrawn past) the tabs 183 of the first hypotube 177, the tabs 183 are biased inwardly to release the first hypotube 177 from the lock 176 to enable it to also be retracted. FIG. 32A illustrated the lock 176 after the first 177 and second 178 hypotubes have been retracted. Moreover, pulling of the retracting hypotube 178 causes retraction of locking clip 179, which pushes down on locking tabs 182, engaging chord 160 and anchor line 63. More specifically, the second hypotube 178 is retracted and due to its connection to locking clip 179, it also retracts the locking clip 179. The locking clip 179, upon retraction, contacts the tabs 183 of the first gateway hypotube 177, disconnecting the clip 179 permitting the second hypotube 178 to be removed. Once retracting hypotube 178 is pulled, the inner arms of gateway hypotube 177 spring inward. The first gateway hypotube 177, beneficially enables the chord 160 to be locked while the second hypotube 178 is being retracted. Once the gateway hypotube 177 is removed, the clip 179 remains within conduit 174. FIG. 32A shows a cross-sectional view of a lock fully engaged. According to one aspect, the lock positioning rod 170 may be integrated with the gateway hypotube or removably connected thereto. FIG. 14B shows an intact view of a fully engaged lock.

Method of Implanting Reversible Locks (Collet Mechanism) and Tensioning Chords

Figure 33B:
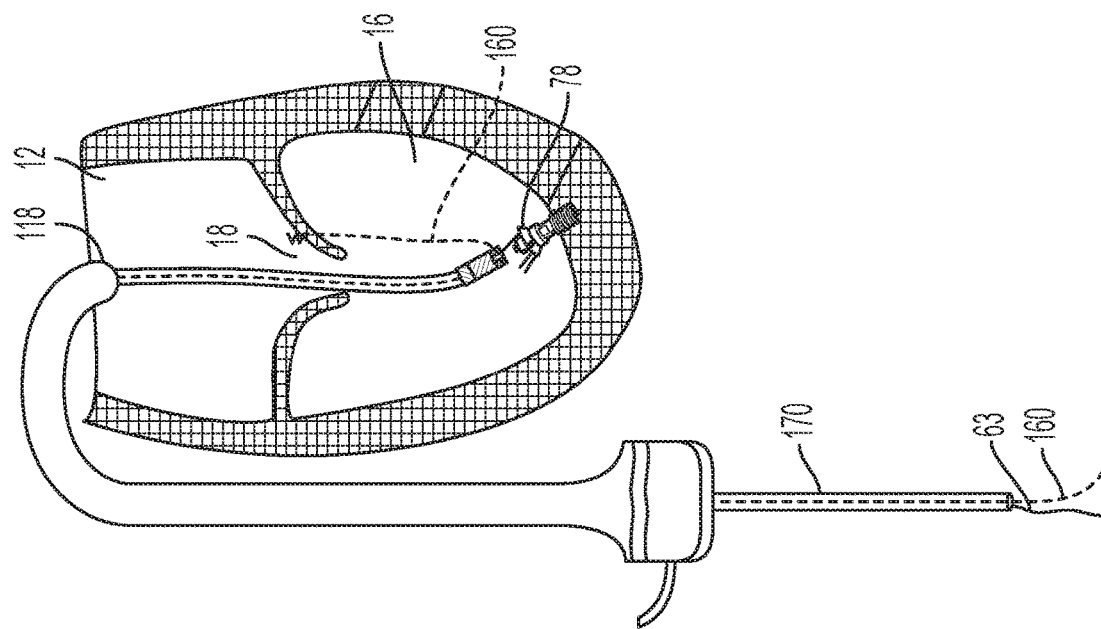
FIG. 33B is a cross-sectional perspective view of the collet locking system advancing over the anchor line and chord to the anchor line rod.
Figure 33A:
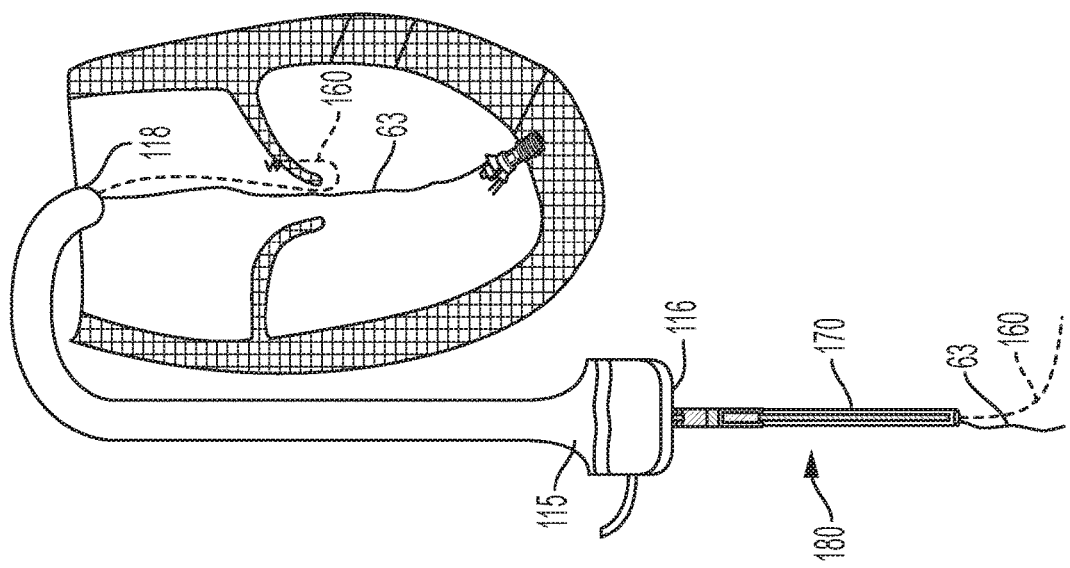
FIG. 33A is a cross-sectional perspective view of the collet locking system entering the transeptal sheath over the anchor line and chord.

Now referring to FIGS. 33A-B, a lock positioning rod 170, of locking system 180, is introduced over a chord 160 and anchor line 63 (for purposes of illustration only one chord and anchor line are illustrated) into lumen 116 of the trans-septal guide 115. The lock positioning rod 170 advances over chord 160 and anchor line 63 through the end 118 of trans-septal guide 115, moving through left atrium 12, across mitral annulus 18, into left ventricle 16, until the end of locking system 180 abuts the anchor line rod 54 or 78. The locking system 180 according to one aspect abuts the anchor line rod 54 or 78, alternatively engages therewith. At this point, chord 160 can be pulled backwards until the appropriate tension has been applied to leaflet 14.

Figure 34B:
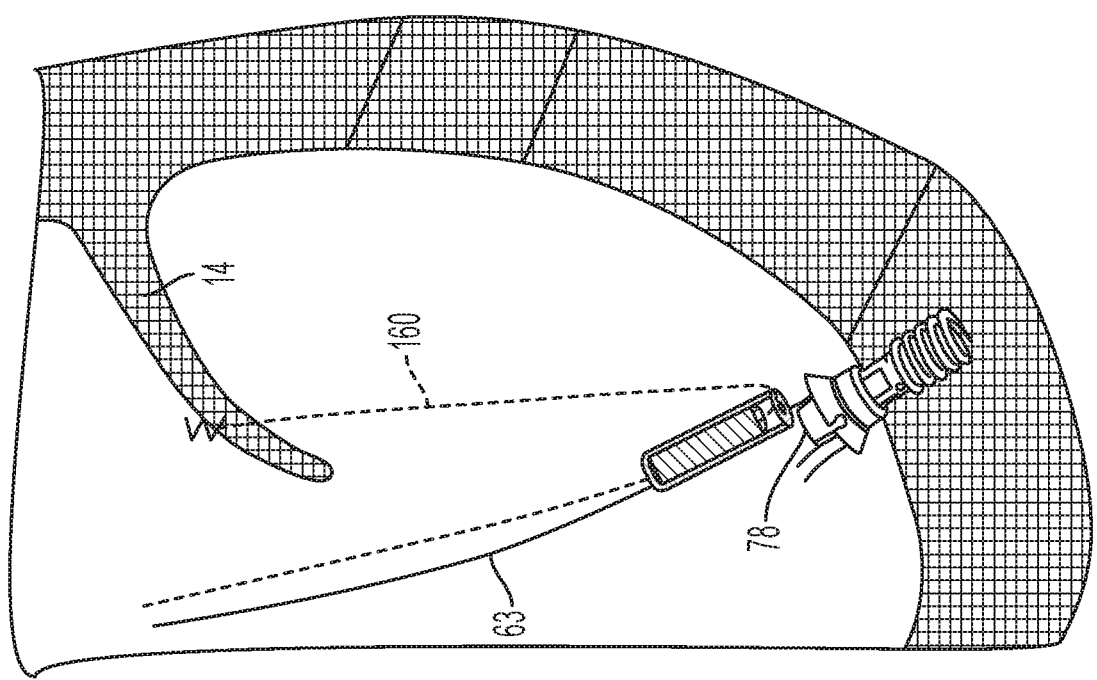
FIG. 34B is a cross-sectional perspective view of the collet locking system locked in place.
Figure 34A:
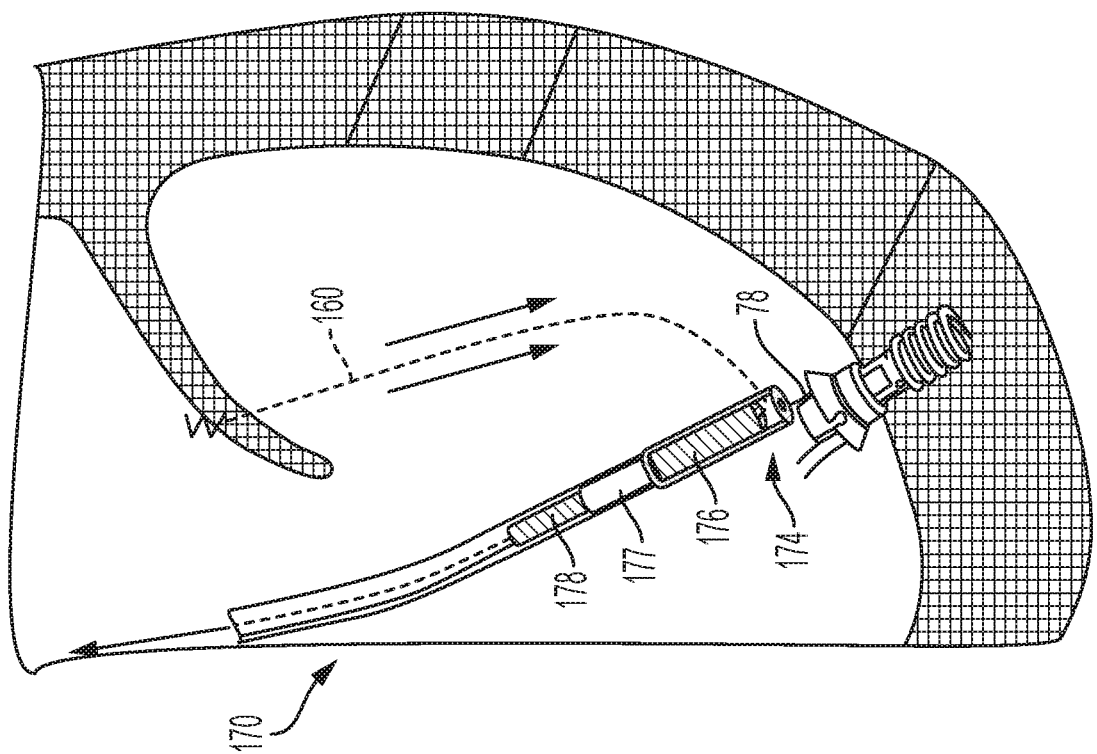
FIG. 34A is a cross-sectional perspective view of the collet locking system in place to be locked.

Now referring to FIG. 34A, chord 160 can be pulled backwards until appropriate tension has been applied to leaflet 14, followed by lock deployment as illustrated in FIG. 34B. In once aspect, if the tension on the chord needs to be adjusted further, the lock may be unlocked so that the chord may freely translate again. Specifically, when the distal end 171 of the lock positioning rod is adjacent to or in contact with the detachable lock 176, the first gateway hypotube 177 is advanced back into the lock 176, followed by the second retracting hypotube 178, whose second mating surface 187 can screw back into first mating surface 186, allowing the second retracting hypotube 178 to push the first mating surface 186 (attached to locking clip 179) down, thereby disengaging locking tabs 182 from chord 160 and anchor line 63. With chord unlocked, more or less tension can be applied to the leaflet 14 by pulling or releasing chord. This process can be repeated as many times as necessary and even after multiple locks have been implanted.

Reversible Locks (Self-Locking)

Now referring to FIGS. 35A-B, the reversible and detachable self-locking locks 190 securely fix the chord 160 to the anchor line 63 and to the anchor line 78 rod of the anchor line swivel attached to the anchor. The locks 190 may be composed of any combination of metallic alloy or plastic, and be of any dimension, shaped as any type of polyhedron or as a cylinder whose cross-section area can be a circle or ellipse. Each lock 190 has a chord lumen 191 of any caliber through which the chord runs, and an anchor line lumen 192 of any caliber through which the anchor line 63 runs. As shown in FIG. 35A, as the chord 160 is pulled through the chord lumen, a binding plate 193 allows the chord 160 to be pulled up, but does not allow the chord to move down, thereby maintaining any tension applied to chord. The binding plate 193 can be of any dimension and polygonal shape, and composed of any metallic allow, plastic, or covered in silicon. As shown in FIG. 35B, to release tension, the anchor line 63 is pulled up, bring up an unlocking element 194, composed of any metallic allow or plastic polymer, and may be shaped as a sphere, cylinder, or any polyhedron. The unlocking element 194 pushes up the binding plate 193, allowing to the chord to translate up or down in the chord lumen. Because the unlocking element is fixed to the anchor line by a spring 196, releasing tension on anchor line allows the spring 196 to bring the anchor line 63 and attached unlocking element 194 down, thereby causing the binding plate 193 within the lock 190 to re-engage with the chord 160, re-locking chord tension by preventing the chord from slipping back down, as shown in FIG. 35A. The lumens 191 and 192 in FIGS. 35A and 35B are shown as representative. The lumens 191 and 192B define channels (not shown) for receipt of the respective member.

Method of Implanting Reversible Locks (Self-Locking) and Tensioning Chords

Figure 36B:
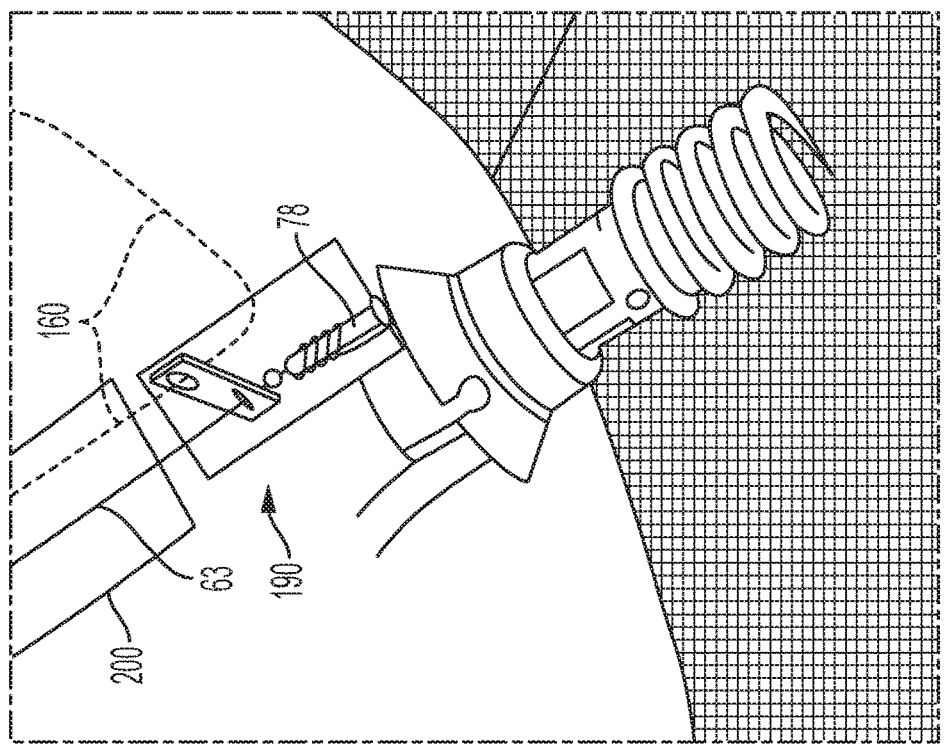
FIG. 36B is a magnified cross-sectional perspective view of the self-locking lock abutting the anchor line rod.
Figure 36A:
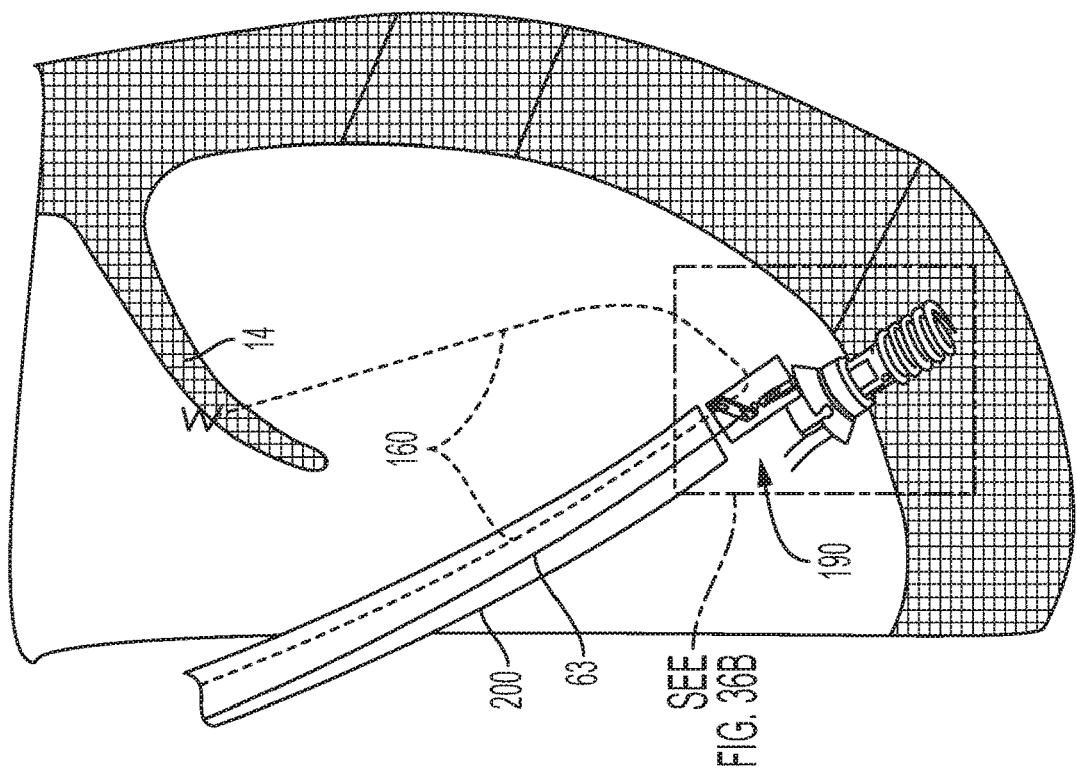
FIG. 36A is a cross-sectional perspective view of the self-locking lock abutting the anchor line rod.

Now referring to FIGS. 36A-B, a lock positioning rod 200, pushes lock 190 over a chord 160 and anchor line 63, until lock 190 docks onto anchor line rod 78 of the anchor line swivel attached to the anchor. Lock positioning rod 200 may be retracted anytime after docking, and preferentially is removed before final chord tensioning to understand efficacy of chord without the rod being across the mitral coaptation plane. Final chord tensioning, as shown in FIGS. 35A-B, occurs when chord 160 can be pulled through chord lumen 191 until appropriate tension is placed on leaflet 14 (in FIG. 36A), and this tension is automatically maintained because binding plate 193 prevents chord 160 from slipping back though chord lumen 191. As stated in [0085], if chord tension needs to lessened, pulling on anchor line 63 brings the unlocking element 194 up, thereby pushing up binding plate 193 so that chord 160 can again freely translate through chord lumen 190.

Chord Tension Regulator, Chord Tension Control Board, and Method of Chord Tensioning As shown in FIG. 37, the chord tension regulator 210 has a chord lumen 211 with chord lumen exit 212 through which the chord 160 runs. The chord tension regulator also has an anchor rod lumen 214 which snaps onto anchor rod 78, once the regulator 210 is pushed by a regulator rod (not shown) onto the base of the anchor rod 78. The top of the anchor rod 78 exits the anchor rod exit 213, and the anchor line 63 is attached to the top of the anchor rod 78.

Figure 38A:
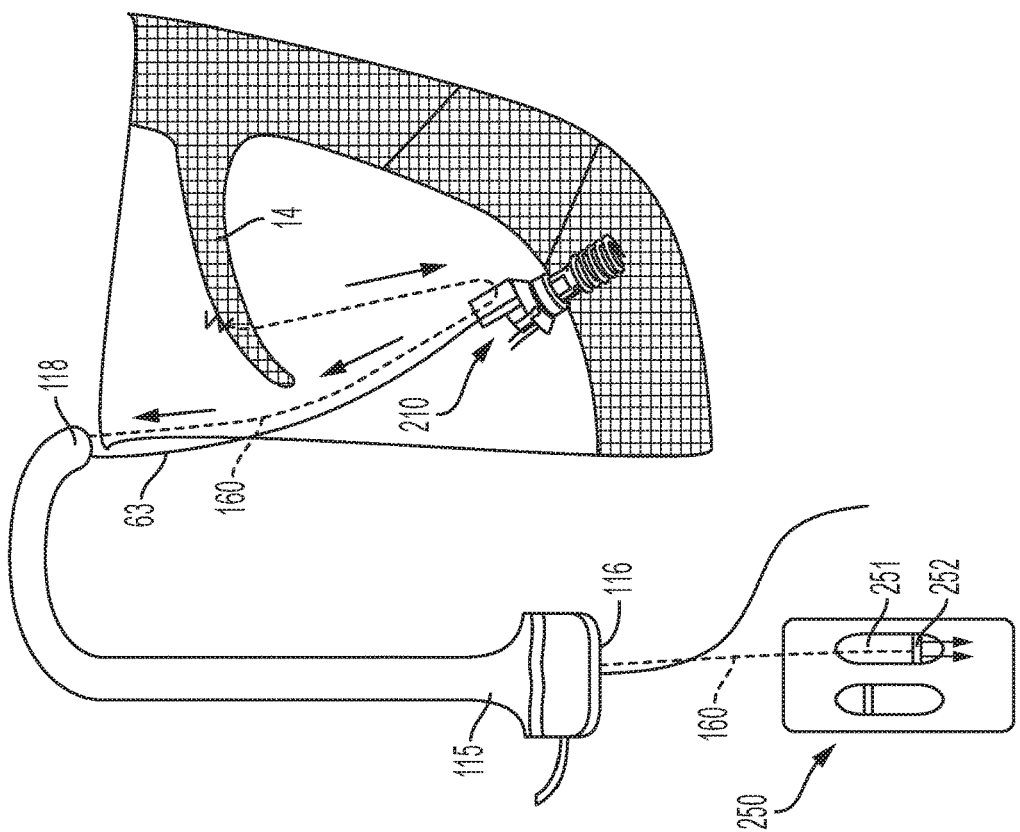
FIG. 38A is a cross-sectional perspective view of the chord tension regulator in place, and the chord attached to the chord tension control board but not tensioned yet.
Figure 38B:
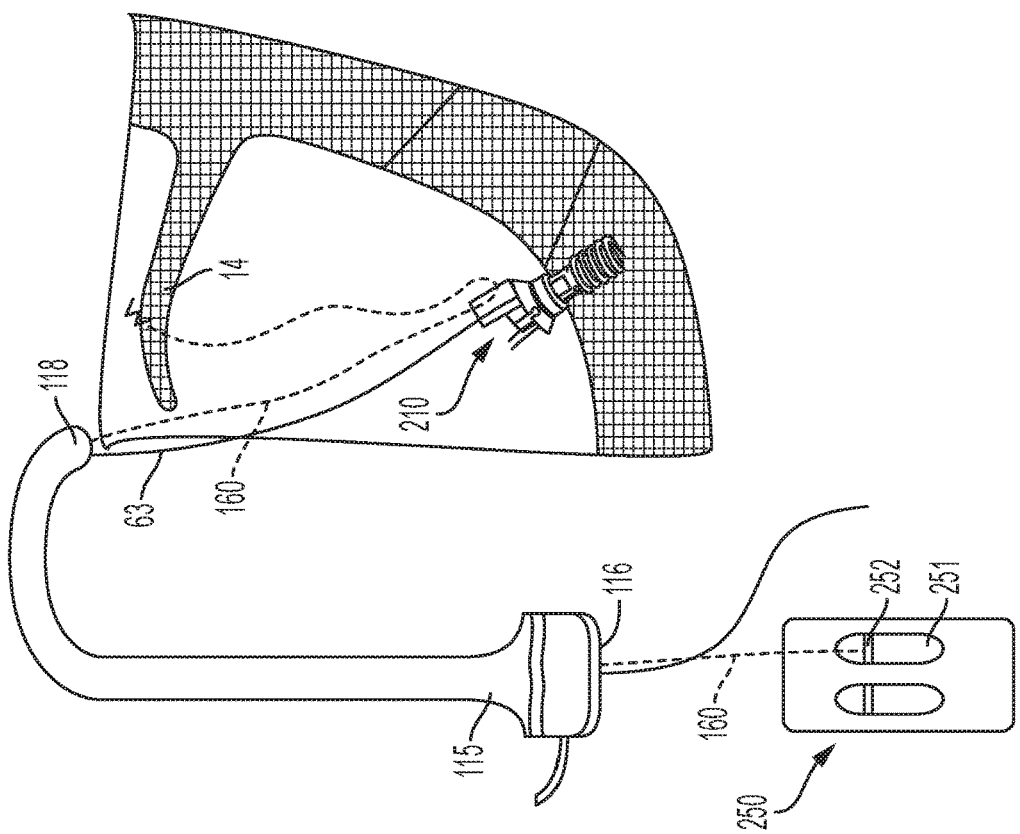
FIG. 38B is a cross-sectional perspective view of the chord tension regulator in place, and the chord attached to the chord tension control board, and the chord has been tensioned.

FIGS. 38A-B show how the chord tension regulator functions with the chord tension control board 250 to adjust tension of the chord 160. The chord tension control board 250 houses one or more chord tension controls 251, each of which contains a chord tension lever 252. As shown in FIG. 38A, the chord 160 and anchor line 63 enter the distal end 118 of the transeptal sheath 115, both exiting out the sheath through the central sheath channel 116.

The operator may attach one or more chords 160 to one or more chord tension levers 252 of the chord tension control board 250. Initially, as shown in FIG. 38A, the chord tension lever 252 has not been retracted so the chord 160 is in the relaxed position, and has not tensioned the leaflet 14. As shown in FIG. 38B, as the chord tension lever 252 is retracted, the chord 160 is pulled backward through the chord tension regulator 210, until the chord 160 has adequate tension on leaflet 14. The chord tension lever 252 maintains its position, but at anytime may be readjusted to release or increase tension on the chord 160 and attached leaflet 14.

Reversible Locks (Locking/Unlocking)

Now referring to FIGS. 39A-B, the locking/unlocking reversible locks 220 securely fix the chord 160 to the anchor line 63 and to the anchor line 78 rod of the anchor line swivel attached to the anchor. The locks 220 may be composed of any combination of metallic alloy or plastic, and be of any dimension, shaped as any type of polyhedron or as a cylinder whose cross-section area can be a circle or ellipse. Each lock 220 has a chord lumen 221 of any caliber, with chord lumen exit 222, through which the chord runs, and the anchor line 63 runs through the push button element 226 (composed of any metallic alloy or plastic polymer), then through the locking chamber 227, through the binding plate pusher 228 until the anchor line 63 exits the anchor line exit 229, which abuts the binding plate 223. As shown in FIG. 39A, when the lock 220 is unlocked, the chord 160 can translate freely through chord lumen 221 and chord lumen exit 222.

In principle, the locking chamber 227, push button element 226, and binding plate pusher 228, function just like a standard retractable ballpoint pen. Specifically, the push button element 226 can slide back and forth via internal grooves (not shown) of locking chamber 227 and is always urged backwards by internal spring (not shown). The push button element, itself, has distal slanted edges (not shown) that co-operate with a cam shaft (not shown) abutting binding plate pusher 228. As in a retractable ballpoint pen, the push button element pushes the cam shaft forward past the internal grooves; once past the internal grooves, the cam shaft cooperates further with the push button element edges, consequently rotating. When the spring pushes the cam shaft back, because the shaft has rotated it settles in a "forward" position as it sets against the internal grooves. When the push button element pushes the cam shaft forward again, the cam shaft rotates again, and as it is pushed back by internal spring, settling in its baseline "backward" position.

Thus, as shown in FIG. 39A, by retracting the anchor line 63, attached to unlocking element 224 (composed of any metallic allow or plastic polymer, and may be shaped as a sphere, cylinder, or any polyhedron), the unlocking element 224 brings the push button element 226 into locking chamber 227, which pushes binding plate pusher 228 into the anchor line exit 229, thereby causing binding plate 223 to crimp the chord 160 as it exits the chord lumen exit 222, thereby locking chord 160 in place. As shown in FIG. 39A, because push button element 226 is attached to anchor line rod 78 by spring 231, the push button element 226 is automatically retracted away from locking chamber 227 back down when anchor line 63 is released. By pulling the anchor line 63 a second time the push button element re-enters the locking chamber 227, pushing on push button element 226, which interacts with internal elements, as described above causing binding plate pusher 228 to retract back into locking chamber 227, allowing binding plate 223 to move away from chord lumen exit 222, allowing chord 160 to translate freely again.

The Anchor Line/Chord Crimper

Figure 40B:
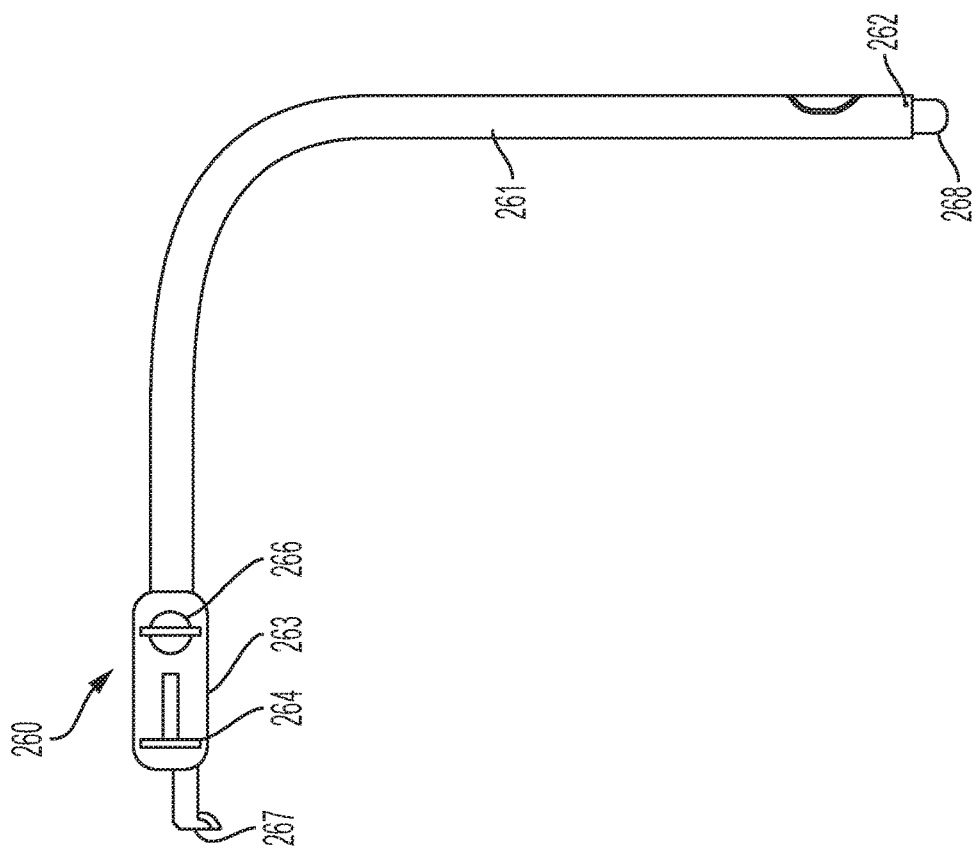
Figure 40A:
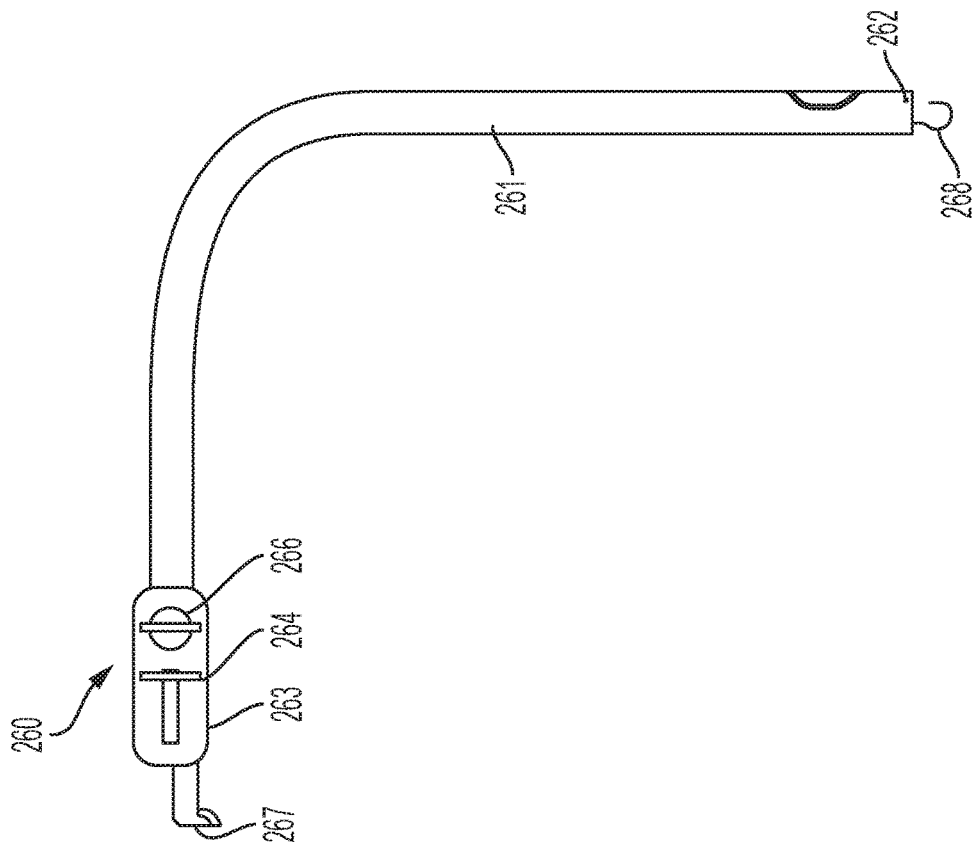
FIG. 40A is a side elevational view of the anchor line/chord crimper with grasper hook pushed out.

As shown in FIG. 40A-B, the anchor line/chord crimper 260 has a control handle 263, shaft 261, distal end 262, connected to grasping hook 268. The control handle 263 contains a grasping lever 264, lock knob 266, and cutting lever 267. FIG. 40A shows grasping lever 264 pushed forward in control handle 263, thereby pushing grasping hook 268 forward, allowing anchor line and chord to enter. FIG. 40B shows grasping lever 264 retracted back in control handle 263, thereby retracting grasping hook 268 back to distal end 262 of the shaft 261.

The Method of Crimping/Cutting Chords

FIGS. 41A-C show the process of the anchor line/chord crimper 260 grabbing the chord 160 and anchor line 63. For purpose of illustration, the anchor/line crimper 260 is shown with the chord tension regulator system, but may be used with other locking systems. In FIG. 41A, the distal end 262 of anchor line/chord crimper 260 is advanced toward chord 160 and anchor line 63. Because the grasping hook 268 is in the open position, the chord 160 and anchor line 63 may be inserted into the grasping hook 268. As illustrated in FIGS. 41B-C, the grasping hook 268 is retracted to the closed position, so that the anchor line/chord crimper 260 may be advanced over the chord 160 and anchor line 63 into trans-septal sheath 115.

Chord 160 vs Anchor Line 63

Figure 42B:
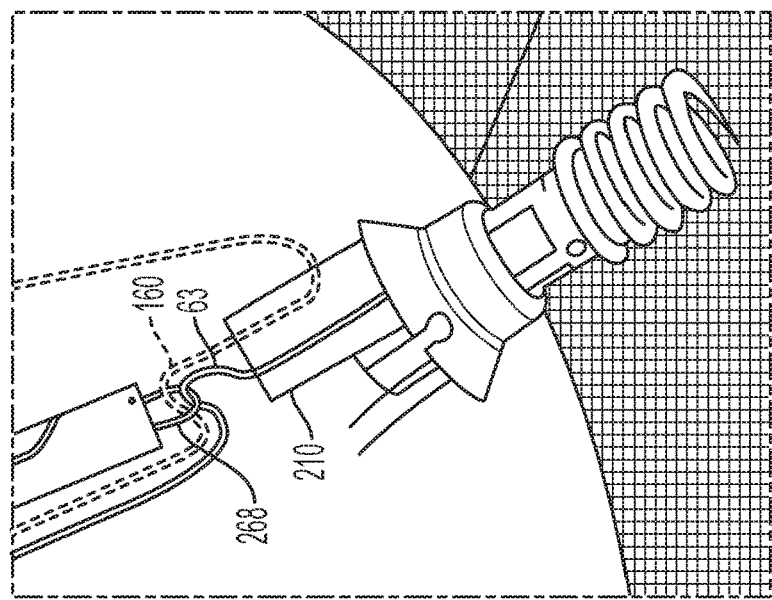
FIG. 42B is a magnified cross-sectional perspective view of the anchor line/chord crimper advanced down to the chord tension regulator.
Figure 42A:
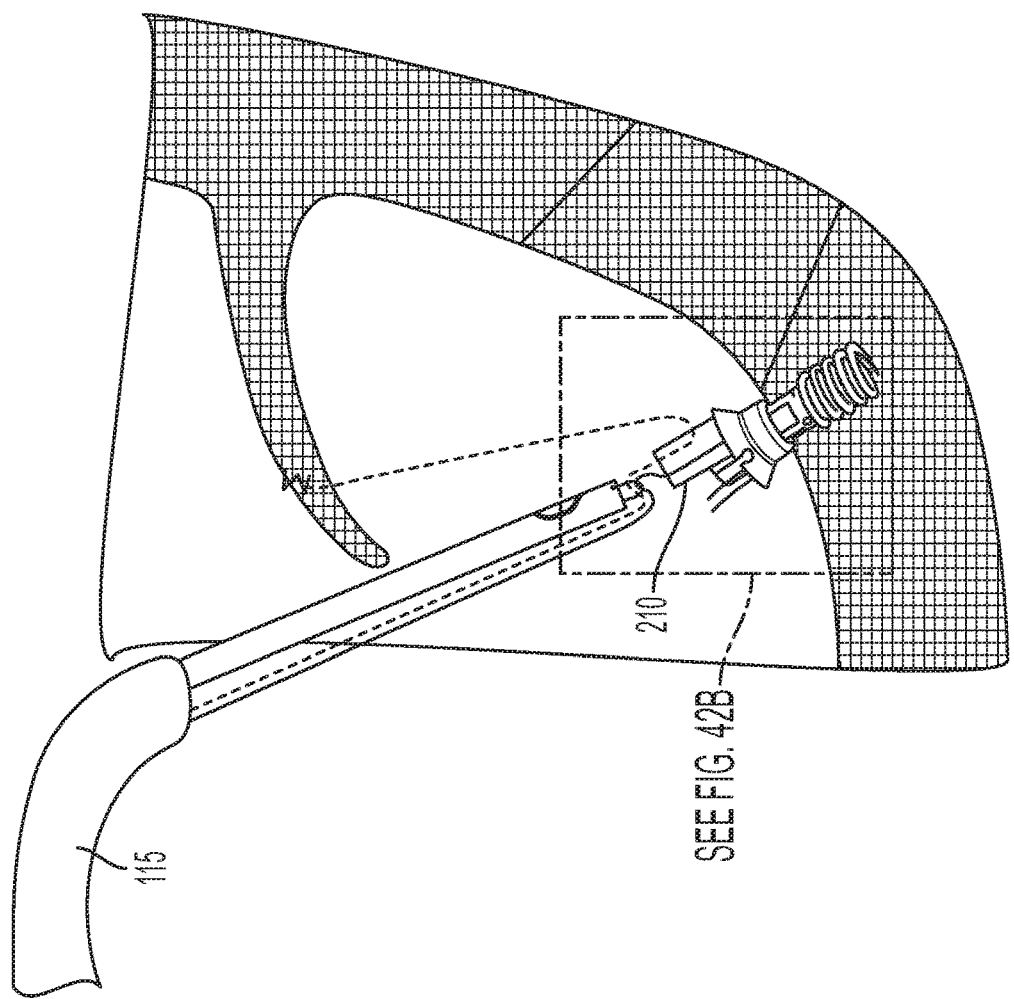
FIG. 42A is a cross-sectional perspective view of the anchor line/chord crimper advanced down to the chord tension regulator.

FIGS. 42A-B show the anchor line/chord crimper 260 that has advanced through trans-septal sheath 115 until the grasping hook 268 is next to the chord tension regulator 210. In FIGS. 43A-B, lock knob 266 (FIGS. 40A-B) has been rotated, thereby deploying lock 280 to fix chord 160 and anchor line 63 to chord tension regulator 210. At the same time, cutting lever 267 (FIGS. 40A-B) has been pushed, thereby cutting the end of chord 160 and anchor line 63 proximal to lock 280, allowing the proximal chord 160, anchor line 63, and anchor line/chord crimper 260 to be retracted back into trans-septal sheath 115.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

The invention claimed is:

1. An endovascularly implanted medical assembly for a heart and for providing chordal support to a leaflet of a heart valve comprising:
    a chord for providing chordal support to the leaflet and extending through the leaflet and between the leaflet and an intracardiac wall;
    an anchor assembly for securing said medical assembly to the intracardiac wall, said anchor assembly having a proximal end facing the leaflet and a distal end configured to cooperate with said intracardiac wall to secure said anchor assembly and said chord;
    an anchor line extending from said anchor assembly proximal end;
    an endovascularly introduced removeable leaflet grasper for introducing said chord into the heart and through the leaflet;
    a lock positioning rod defining a lumen; and
    a line gathering member for encompassing said chord and said anchor line wherein said chord extends through said leaflet and distally, in a direction toward said anchor assembly, and said chord is secured to said anchor line by said line gathering member, wherein said line gathering member is configured to lock said chord and said line gathering comprises a first hypotube and a second hypotube wherein said first hypotube is positioned within a conduit of said line-gathering member and said second hypotube is positioned within said first hypotube and wherein said chord and said anchor line extend through said lumen of said lock positioning rod and said line gathering member is adjacent to a distal end of said lock positioning rod.

2. The endovascularly implanted medical assembly according to claim 1 wherein said line gathering member is moveable between an unlocked and locked position.

3. The endovascularly implanted medical assembly according to claim 1 wherein said lock positioning rod is connected at a distal end to a proximal portion of said line gathering member.

4. The endovascularly implanted medical assembly according to claim 1 wherein said conduit defines an inner surface configured to matingly engage an outer surface of said second hypotube to engage and disengage said lock.

5. The endovascularly implanted medical assembly according to claim 4 wherein said first and second hypotubes are removeable from said conduit upon locking of said lock.

6. The endovascularly implanted medical assembly according to claim 1 wherein said line gathering member comprises a chord lumen and an anchor lumen and said chord extends along said chord lumen and said anchor line extends along said anchor lumen and said lock further comprises a binding plate for binding said anchor line and chord.

7. The endovascularly implanted medical assembly according to claim 6 further comprising an unlocking element for cooperating with said binding plate for unbinding said chord.

8. The endovascularly implanted medical assembly according to claim 1 wherein said leaflet grasper has a proximal end and a distal end and a grasper arm adjacent its distal end and a grasper shaft extending between said proximal and distal ends wherein said grasper arm is configured to grasp the leaflet between said grasper arm and said grasper shaft.

9. The endovascularly implanted medical assembly according to claim 8 wherein said anchor line extends within said grasper shaft.

10. The endovascularly implanted medical assembly according to claim 8 wherein said leaflet grasper is formed of a flexible material.

11. The endovascularly implanted medical assembly according to claim 8 wherein said grasper arm comprises a grasping plate connected to an articulating arm which is moveable from a first closed position for insertion of the said leaflet grasper to a second grasping position for securing the leaflet against said grasper shaft.

12. The endovascularly implanted medical assembly according to claim 11 wherein said leaflet grasper further comprises a trajectory knob operatively connected to said distal end of said leaflet grasper for controlling trajectory of said leaflet grasper.

13. The endovascularly implanted medical assembly according to claim 12 wherein said leaflet grasper further comprises a grasper control for moving said articulating arm and said grasping plate between said first and said second positions.

14. The endovascularly implanted medical assembly according to claim 11 wherein said leaflet grasper comprises a puncturing rod extending within said grasper shaft and a puncturing rod distal end defining a puncturing element configured to puncture the leaflet when the leaflet is retained in said grasping plate second grasping position.

15. The endovascularly implanted medical assembly according to claim 14 wherein said anchor line is connected to said puncturing element and said anchor line extends within said puncturing rod.

16. The endovascularly implanted medical assembly according to claim 14 wherein said leaflet grasper comprises a receiving cap defining a lumen wherein said receiving cap is positioned in said grasper shaft distally to said puncturing element prior to puncturing the leaflet and said lumen is configured to receive said puncturing element when the leaflet has been punctured.

17. The endovascularly implanted medical assembly according to claim 16 wherein said leaflet grasper comprises a retracting rod extending within a chord release tube of said grasper shaft and wherein said receiving cap is connected to a distal end of said retracting rod and said receiving cap is retracted from said leaflet grasper by retraction of said retracting rod.

18. The endovascularly implanted medical assembly according to claim 8 wherein said leaflet grasper distal end defines a nosecone.

19. The endovascularly implanted medical assembly according to claim 1 wherein said chord includes a pledget on a proximal end and said pledget cooperates with a proximal side of the leaflet when said puncturing element has punctured the leaflet.

20. The endovascularly implanted medical assembly according to claim 1 wherein said chord includes a knot on a proximal end and said knot cooperates with a proximal side of the leaflet when said puncturing element has punctured the leaflet.

21. The endovascularly implanted medical assembly according to claim 1 further comprising a transseptal sheath configured to receive said leaflet grasper to introduce said leaflet grasper into the heart.

22. The endovascularly implanted medical assembly according to claim 1 further comprising a crimper for grabbing said chord and said anchor line wherein said crimper includes a grasping hook configured to receive said chord and said anchor line.

23. The endovascularly implanted medical assembly according to claim 22 wherein said grasping hook is moveable between an open and closed position.

24. The endovascularly implanted medical assembly according to claim 1 wherein said anchor assembly comprises an anchor having an anchor securing member on its distal end and an anchor cap on its proximal end.

25. The endovascularly implanted medical assembly according to claim 24 wherein said anchor assembly further comprises an anchor line swivel having a docking ring rotatably connected to said anchor cap wherein said anchor line swivel rotates about said anchor cap and said chord extends proximal to said docking ring.

26. The endovascularly implanted medical assembly according to claim 25 wherein said anchor assembly further comprises an anchor line rod extending proximally from said anchor line swivel and said chord extends proximally from said anchor line rod.

27. The endovascularly implanted medical assembly according to claim 26 further comprising an endovascularly inserted anchor delivery system comprising a delivery cable having a distal end configured to cooperate with said anchor cap wherein said anchor line swivel is configured to be received over said delivery cable.

28. The endovascularly implanted medical assembly according to claim 27 wherein said delivery cable is flexible.

29. The endovascularly implanted medical assembly according to claim 27 wherein said delivery cable distal end is threaded and a proximal surface of said anchor cap defines a threaded receptable configured for removeable mating with said delivery cable distal end.

30. The endovascularly implanted medical assembly according to claim 26 wherein said anchor line swivel comprises at least two of said anchor line rods.

31. The endovascularly implanted medical assembly according to claim 25 wherein said anchor cap comprises at least one locking arm sized and configured for releasably securing said anchor line swivel and cooperating with said docking ring.

32. The endovascularly implanted medical assembly according to claim 31 wherein said at least one locking arm extends in a first extended position a first distance from an outer surface of said anchor cap and moves to a second retracted position a second distance from said anchor cap outer surface wherein said second distance is less than said first distance.

33. The endovascularly implanted medical assembly according to claim 32 wherein said at least one locking arm which is biased in said first position.

34. The endovascularly implanted medical assembly according to claim 32 wherein said anchor line swivel is configured to move said at least one locking arm from said first extended position to said second retracted position and wherein said at least one locking arm secures said anchor line swivel on said anchor cap in said first extended position.

35. The endovascularly implanted medical assembly according to claim 32 wherein said anchor cap comprises at least two of said at least one locking arms.

36. The endovascularly implanted medical assembly according to claim 26 wherein said anchor line rod defines a hook on its distal end and said docking ring defines and eyelet wherein said hook mates with said eyelet and said anchor line rod is connected to said eyelet and is rotatably moveable along said eyelet.

37. The endovascularly implanted medical assembly according to claim 26 wherein said anchor line rod has a proximal end which is coupled to said anchor line.

38. The endovascularly implanted medical assembly according to claim 37 wherein said anchor line rod defines a side channel and said anchor line extends through said channel and said anchor line extends proximally from said anchor line rod as a pair of said anchor lines.

39. The endovascularly implanted medical assembly according to claim 1 wherein said anchor assembly distal end comprises an anchor screw for implanting into the intracardiac wall.

40. A method of endovascularly implanting a medical assembly into a heart for providing chordal support to a leaflet of a heart valve comprising the steps of:
providing an endovascularly implanted medical assembly comprising a chord for providing chordal support to the leaflet and extending through the leaflet and between the leaflet and an intracardiac wall; an anchor assembly for securing said medical assembly to the intracardiac wall, said anchor assembly having a proximal end facing the leaflet and a distal end configured to cooperate with said intracardiac wall to secure said anchor assembly and said chord; an endovascularly introduced removeable leaflet grasper for introducing said chord into the heart and through the leaflet wherein said leaflet grasper has a proximal end and a distal end and comprises a grasper arm adjacent its distal end and a grasper shaft extending between said proximal and distal ends wherein said grasper arm is configured to grasp the leaflet between said grasper arm and said grasper shaft; and an anchor line extending from said anchor assembly proximal end and within said grasper shaft and a line gathering member for encompassing said chord and said anchor line wherein said chord extends through said leaflet and distally, in a direction toward said anchor assembly, and said chord is secured to said anchor line by said line gathering member;
endovascularly inserting an anchor assembly and anchoring the anchor assembly to an intracardiac wall wherein the anchor assembly includes an anchor having an anchor securing member on a distal end and an anchor cap on its proximal end;
endovascularly inserting an at least one anchor line extending proximally from said anchor assembly;
endovascularly inserting n said leaflet grasper wherein the leaflet grasper distal end and grasping arm are inserted past and below the leaflet;
opening said grasping arm and closing the grasping arm to grasp the leaflet;
piercing the leaflet with said leaflet grasper and inserting a chord by providing the leaflet grasper with a puncturing rod extending within said grasper leaflet and urging said puncturing rod distally to urge a puncturing element through the leaflet and beyond the leaflet in a direction towards the anchor assembly;
removing said leaflet grasper;
inserting a line gathering member and encompassing said chord and said anchor line wherein said line gathering member is configured to lock said chord and said chord is secured to said anchor line by said line gathering member; and
providing a lock positioning rod wherein said chord extends through said lumen of said lock positioning rod and said line gathering member is adjacent to a distal end of said lock positioning rod.

41. The method according to claim 40 further comprising the step of removing said piercing element by providing the leaflet grasper with a receiving cap defining a lumen and said receiving cap is positioned distally to said puncturing element prior to puncturing the leaflet and said step of piercing the leaflet includes capturing the piercing element within the lumen and withdrawing the receiving cap from the leaflet grasper.

42. The method according to claim 40 further comprising the step of locking the tension of said chord after said step of adjusting the tension.

43. An endovascularly implanted medical assembly for a heart and for providing chordal support to a leaflet of a heart valve comprising:
a chord for providing chordal support to the leaflet and extending through the leaflet and between the leaflet and an intracardiac wall;
an anchor assembly for securing said medical assembly to the intracardiac wall, said anchor assembly having a proximal end facing the leaflet and a distal end configured to cooperate with said intracardiac wall to secure said anchor assembly and said chord;
an endovascularly introduced removeable leaflet grasper for introducing said chord into the heart and through the leaflet wherein said leaflet grasper has a proximal end and a distal end and comprises a grasper arm adjacent its distal end and a grasper shaft extending between said proximal and distal ends wherein said grasper arm is configured to grasp the leaflet between said grasper arm and said grasper shaft; and
an anchor line extending from said anchor assembly proximal end and within said grasper shaft and a line gathering member for encompassing said chord and said anchor line wherein said chord extends through said leaflet and distally, in a direction toward said anchor assembly, and said chord is secured to said anchor line by said line gathering member.

44. The endovascularly implanted medical assembly according to claim 43 wherein said line gathering member is configured for receipt of said chord and wherein said line gathering member is moveable between an unlocked and locked position, and said chord is secured to said anchor line by said line gathering member.

45. The endovascularly implanted medical assembly according to claim 43 wherein said leaflet grasper comprises a control handle on its proximal end.

46. The endovascularly implanted medical assembly according to claim 43 wherein said leaflet grasper is formed of a flexible material.

47. The endovascularly implanted medical assembly according to claim 43 wherein said grasper arm comprises a grasping plate connected to an articulating arm which is moveable from a first closed position for insertion of the said leaflet grasper to a second grasping position for securing the leaflet against said grasper shaft.

48. The endovascularly implanted medical assembly according to claim 47 wherein said leaflet grasper further comprises a trajectory knob operatively connected to said distal end of said leaflet grasper for controlling trajectory of said leaflet grasper.

49. The endovascularly implanted medical assembly according to claim 47 wherein said leaflet grasper further comprises a grasper control for moving said articulating arm and said grasping plate between said first and said second positions.

50. The endovascularly implanted medical assembly according to claim 43 wherein said leaflet grasper distal end defines a nosecone.

51. The endovascularly implanted medical assembly according to claim 43 wherein said leaflet grasper comprises a puncturing rod extending within said grasper shaft and a puncturing rod distal end defining a puncturing element configured to puncture the leaflet when the leaflet is retained by said leaflet grasper.

52. The endovascularly implanted medical assembly according to claim 51 wherein said anchor line is connected to said puncturing element and said anchor line extends within said puncturing rod.

53. The endovascularly implanted medical assembly according to claim 51 wherein said leaflet grasper comprises a receiving cap defining a lumen wherein said receiving cap is positioned in said grasper shaft distally to said puncturing element prior to puncturing the leaflet and said lumen is configured to receive said puncturing element when the leaflet has been punctured.

54. The endovascularly implanted medical assembly according to claim 53 wherein said leaflet grasper comprises a retracting rod extending within a chord release tube of said grasper shaft and wherein said receiving cap is connected to a distal end of said retracting rod and said receiving cap is retracted from said leaflet grasper by retraction of said retracting rod.

55. The endovascularly implanted medical assembly according to claim 43 wherein said chord includes a pledget on a proximal end and said pledget cooperates with a proximal side of the leaflet when said puncturing element has punctured the leaflet.

56. The endovascularly implanted medical assembly according to claim 43 wherein said chord includes a knot on a proximal end and said knot cooperates with a proximal side of the leaflet when said puncturing element has punctured the leaflet.

57. The endovascularly implanted medical assembly according to claim 43 further comprising a transseptal sheath configured to receive said leaflet grasper to introduce said leaflet grasper into the heart.

58. The endovascularly implanted medical assembly according to claim 43 further comprising a crimper for grabbing said chord and said anchor line wherein said crimper includes a grasping hook configured to receive said chord and said anchor line.

59. The endovascularly implanted medical assembly according to claim 58 wherein said grasping hook is moveable between an open and closed position.

60. The endovascularly implanted medical assembly according to claim 43 wherein said anchor assembly comprises an anchor having an anchor securing member on its distal end and an anchor cap on its proximal end.

61. The endovascularly implanted medical assembly according to claim 60 wherein said anchor assembly further comprises an anchor line swivel having a docking ring rotatably connected to said anchor cap wherein said anchor line swivel rotates about said anchor cap and said chord extends proximal to said docking ring.

62. The endovascularly implanted medical assembly according to claim 61 wherein said anchor assembly further comprises an anchor line rod extending proximally from said anchor line swivel and said chord extends proximally from said anchor line rod.

63. An endovascularly implanted medical assembly for a heart and for providing chordal support to a leaflet of a heart valve comprising:
   a chord for providing chordal support to the leaflet and extending through the leaflet and between the leaflet and an intracardiac wall;
   an anchor assembly for securing said medical assembly to the intracardiac wall, said anchor assembly having a proximal end facing the leaflet and a distal end configured to cooperate with said intracardiac wall to secure said anchor assembly and said chord;
   an anchor line extending from said anchor assembly proximal end;
   an endovascularly introduced removeable leaflet grasper for introducing said chord into the heart and through the leaflet;
   a line gathering member for encompassing said chord and said anchor line wherein said chord extends through said leaflet and distally, in a direction toward said anchor assembly, and said chord is secured to said anchor line by said line gathering member; and
   a crimper for grabbing said chord and said anchor line wherein said crimper includes a grasping hook configured to receive said chord and said anchor line.

64. The endovascularly implanted medical assembly according to claim 63 wherein said grasping hook is moveable between an open and closed position.

* * * * *